US010821195B2

(12) United States Patent
Lewis et al.

(10) Patent No.: US 10,821,195 B2
(45) Date of Patent: Nov. 3, 2020

(54) COMPOSITIONS FOR THERAPEUTICS, TARGETED PET IMAGING AND METHODS OF THEIR USE

(71) Applicants: Memorial Sloan Kettering Cancer Center, New York, NY (US); Research Foundation of the City University of New York, New York, NY (US)

(72) Inventors: Jason S. Lewis, New York, NY (US); Melissa Deri, Hottsville, NY (US); Lynn Francesconi, Bridgewater, NJ (US); Shashikanth Ponnala, Secaucus, NJ (US)

(73) Assignees: Memorial Sloan Kettering Cancer Center, New York, NY (US); Research Foundation of the City University of New York, New York, NY (US)

( * ) Notice: Subject to any disclaimer, the term of this patent is extended or adjusted under 35 U.S.C. 154(b) by 149 days.

(21) Appl. No.: 15/759,154

(22) PCT Filed: Sep. 9, 2016

(86) PCT No.: PCT/US2016/051116
§ 371 (c)(1),
(2) Date: Mar. 9, 2018

(87) PCT Pub. No.: WO2017/105565
PCT Pub. Date: Jun. 22, 2017

(65) Prior Publication Data
US 2019/0298864 A1 Oct. 3, 2019

Related U.S. Application Data

(60) Provisional application No. 62/216,889, filed on Sep. 10, 2015.

(51) Int. Cl.
*A61K 51/04* (2006.01)
*A61K 9/00* (2006.01)
*A61K 51/10* (2006.01)

(52) U.S. Cl.
CPC ........ *A61K 51/0482* (2013.01); *A61K 9/0019* (2013.01); *A61K 51/0478* (2013.01); *A61K 51/1051* (2013.01); *A61K 51/1093* (2013.01)

(58) Field of Classification Search
CPC combination set(s) only.
See application file for complete search history.

(56) References Cited

FOREIGN PATENT DOCUMENTS

WO    WO-2013167754 A1 * 11/2013 ......... A61K 51/1027

OTHER PUBLICATIONS

Deri et al., J. Med.Chem. 2014, 57, 4849-4860.*
Chuangyan et al., "Novel bifunctional cyclic chelator for 89 Zr lableling, radiolabeling and targeting properties of RGD conjugates," Molecular Pharmaceutics, vol. 12, No. 6, pp. 2142-2150 (Jun. 1, 2015).
D'Aleo et al., "Optimization of the Sensitization Process and Stability of Octadentate Eu(III) 1,2-HOPO Complexes," Inorganic Chemistry, vol. 54, No. 14, pp. 6807-6820 (Jul. 20, 2015).
Daumann et al., "New insights into structure and luminescence of Eu III and Sm III complexes of the 3,4,3-LI (1,2-HOPO) ligand," Journal of the American Chemical Society, vol. 137, No. 8, pp. 2816-2819 (Mar. 4, 2015).
Deri et al., "Alternative chelator for 89 Zr Radiopharmaceuticals: radiolabeling and evaluation of 3,4,3-(LI-1, 2-HOPO)," Journal of Medicinal Chemistry, vol. 57, No. 11, pp. 4849-4860 (Jun. 12, 2014).
Deri et al., "p-SCN-Bn-HOPO: A New Bifunctional Chelator for Zr-89 Radiopharmaceuticals," vol. 58, No. 1, p. S7 (May 31, 2015).
Deri et al., "p-SCN-Bn-HOPO: A superior bifunctional chelator for 89 Zr ImmunoPET," Bioconjugate Chemistry, vol. 26, No. 12, pp. 2579-2591 (Dec. 16, 2015).
International Search Report and Written Opinion, PCT/US2016/051116, Memorial Sloan Kettering Cancer Center et al., 12 pages (Jul. 12, 2017).
Ma et al., "Tripodal tris(hydroxypyridinone) ligands for immunoconjugate PET imaging with 89 Zr 4 : comparison with desferrioxamine-B," Dalton Transactions: The International Journal for Inorganic, Organometallic and Bioinorganic Chemistry, vol. 44, No. 11, pp. 4884-4900 (Jan. 1, 2015).
Malay et al., "An octadentate bifunctional chelating agent for the development of stable zirconium-89 based molecular imaging probes," Chemical Communications, vol. 50, No. 78, pp. 11523-11525 (Aug. 13, 2014).
Price et al., "p-NO2-Bn-bisDFO: A new high denticity chelator for Zr-89 radiochemistry," Journal of Labelled Compounds and Radiopharmaceuticals, vol. 58, No. 1, p. S101 (May 31, 2015).
Sturzbecher-Hoehne et al., "3,4,3-LI (1,2-HOPO): In vitro formation of highly stable lanthanide complexes translates into efficacious in vivo europium decorporation," Dalton Transactions: The International Journal for Inorganic, Organometallic and Bioinorganic Chemistry, vol. 40, No. 33, pp. 8340 (Jan. 1, 2011).
Tedeschi et al., "A solid-state study of the eight-coordinate lanthanide(iii) complexes (Ln = Eu, Gd, Tb, Dy) with 1-hydroxy-2-phridinone," Dalton Transactions: The International Journal for Inorganic, Organometallic and Bioinorganic Chemistry, No. 9, pp. 1738-1745 (Apr. 17, 2003).

* cited by examiner

Primary Examiner — Robert S Cabral
(74) Attorney, Agent, or Firm — Foley & Lardner LLP

(57) ABSTRACT

Described herein is a chelator for radiolabels (e.g., $^{89}$Zr) for targeted PET imaging that is an alternative to DFO. In certain embodiments, the chelator for $^{89}$Zr is the ligand, 3,4,3-(LI-1,2-HOPO) ("HOPO"), which exhibits equal or superior stability compared to DFO in chemical and biological assays across a period of several days in vivo. As shown in FIG. 1, the HOPO is an octadentate chelator that stabilizes chelation of radiolabels (e.g., $^{89}$Zr). A bifunctional ligand comprising p-SCN-Bn-HOPO is shown in FIG. 4 and FIG. 5. Such a bifunctional ligand can eliminate (e.g., $^{89}$Zr) loss from the chelate in vivo and reduce uptake in bone and non-target tissue. Therefore, the bifunctional HOPO ligand can facilitate safer and improved PET imaging with radiolabeled antibodies.

22 Claims, 38 Drawing Sheets

Zr HOPO    Zr DFO

| COMPETING METAL CATION | % INTACT STARTING SPECIES BY INCUBATION TIME | | | | | | | |
|---|---|---|---|---|---|---|---|---|
| | 1 h | | 1 d | | 5 d | | 7 d | |
| | 89Zr-HOPO | 89Zr-DFO | 89Zr-HOPO | 89Zr-DFO | 89Zr-HOPO | 89Zr-DFO | 89Zr-HOPO | 89Zr-DFO |
| $Co^{2+}$ | 98.5 ± 2.2 | 92.5 ± 0.4 | 98.2 ± 2.6 | 93.4 ± 3.1 | 98.6 ± 2.0 | 96.2 ± 0.5 | 98.9 ± 1.6 | 95.8 ± 1.1 |
| $Cu^{2+}$ | 98.2 ± 2.5 | 95.8 ± 4.0 | 98.1 ± 2.7 | 98.2 ± 2.6 | 98.3 ± 2.4 | 96.8 ± 1.5 | 98.4 ± 2.3 | 95.3 ± 0.2 |
| $Fe^{3+}$ | 97.0 ± 4.2 | 90.6 ± 4.5 | 89.8 ± 5.4 | 48.2 ± 27.0 | 90.5 ± 3.8 | 51.9 ± 11.2 | 83.0 ± 4.2 | 39.1 ± 9.9 |
| $Ga^{3+}$ | 98.4 ± 2.3 | 94.2 ± 5.6 | 97.9 ± 3.0 | 94.9 ± 4.3 | 97.3 ± 1.9 | 93.0 ± 4.4 | 96.4 ± 0.6 | 91.1 ± 2.2 |
| $Gd^{3+}$ | 98.2 ± 2.6 | 94.3 ± 1.4 | 97.8 ± 3.1 | 95.0 ± 2.7 | 96.5 ± 2.9 | 98.4 ± 2.2 | 94.5 ± 4.1 | 97.0 ± 0.7 |
| $K^+$ | 99.0 ± 1.5 | 97.2 ± 4.0 | 98.7 ± 1.9 | 94.8 ± 3.5 | 98.5 ± 2.2 | 97.6 ± 0.7 | 98.1 ± 0.7 | 97.0 ± 1.6 |
| $Mg^{2+}$ | 98.3 ± 2.5 | 94.4 ± 0.02 | 98.3 ± 2.5 | 95.6 ± 2.5 | 98.6 ± 2.0 | 98.1 ± 0.8 | 98.7 ± 1.8 | 96.5 ± 0.1 |
| $Ni^{2+}$ | 98.4 ± 2.3 | 97.2 ± 4.0 | 98.4 ± 2.2 | 94.9 ± 3.2 | 98.7 ± 1.9 | 97.0 ± 1.2 | 97.4 ± 0.1 | 97.8 ± 1.1 |
| $Zn^{2+}$ | 98.6 ± 2.0 | 92.9 ± 2.2 | 98.7 ± 1.9 | 97.9 ± 3.0 | 97.7 ± 3.3 | 97.6 ± 3.4 | 98.3 ± 2.4 | 96.4 ± 1.3 |

FIG. 7

| STARTING COMPLEX | pH | 1H | 1D | 3D | 6D |
|---|---|---|---|---|---|
| 177Lu-HOPO | 8.0 | 98.59 ± 0.03 | 99.39 ± 0.10 | 97.5 ± 0.9 | 91 ± 4 |
| | 7.0 | 98.97 ± 0.15 | 99.39 ± 0.17 | 99.28 ± 0.18 | 96.2 ± 1.9 |
| | 6.0 | 98.7 ± 0.3 | 99.29 ± 0.10 | 98.3 ± 0.9 | 94 ± 2 |
| | 5.0 | 98.7 ± 0.5 | 99.2 ± 0.4 | 95 ± 4 | 86 ± 10 |
| 177Lu-DOTA | 8.0 | 98.35 ± 0.19 | 99.10 ± 0.11 | 98.8 ± 0.3 | 98.3 ± 0.8 |
| | 7.0 | 99.1 ± 0.2 | 98.8 ± 0.3 | 99.2 ± 0.3 | 98.49 ± 0.07 |
| | 6.0 | 99.22 ± 0.17 | 99.03 ± 0.03 | 99.12 ± 0.18 | 98.73 ± 0.04 |
| | 5.0 | 99.1 ± 0.3 | 98.95 ± 0.16 | 99.15 ± 0.19 | 97.8 ± 1.2 |

| STARTING COMPLEX | COMPETING METAL CATION | 1D | 3D | 6D |
|---|---|---|---|---|
| 177Lu-HOPO | $Cu^{2+}$ | 95.5 ± 1.1 | 92 ± 5 | 88 ± 7 |
| | $Fe^{3+}$ | 96.44 ± 0.07 | 97.4 ± 0.9 | 96.4 ± 0.3 |
| | $Ga^{3+}$ | 96.5 ± 1.4 | 97.24 ± 0.17 | 96.3 ± 0.6 |
| | $Gd^{3+}$ | 97.2 ± 0.8 | 97.0 ± 0.3 | 84 ± 8 |
| 177Lu-DOTA | $Cu^{2+}$ | 99.0 ± 0.6 | 99.2 ± 0.3 | 99.4 ± 0.2 |
| | $Fe^{3+}$ | 98.9 ± 0.3 | 98.7 ± 0.5 | 98.7 ± 1.1 |
| | $Ga^{3+}$ | 99.3 ± 0.3 | 99.2 ± 0.3 | 99.2 ± 0.2 |
| | $Gd^{3+}$ | 99.1 ± 0.4 | 98.47 ± 0.06 | 99.0 ± 0.5 |

FIG. 19

|  |  | TERMINAL LIGANDS | | CENTRAL LIGANDS | |
|---|---|---|---|---|---|
| Zr-HOPO { I | CO-Zr | 2.215 | 2.158 | 2.205 | 2.283 |
|  | NO-Zr | 2.269 | 2.326 | 2.270 | 2.223 |
| II | CO-Zr | 2.220 | 2.167 | 2.205 | 2.291 |
|  | NO-Zr | 2.266 | 2.298 | 2.263 | 2.218 |
| Zr-DFO { III(REF[13]) | CO-Zr | 2.261 | 2.254 | 2.199 | n/a |
|  | NO-Zr | 2.121 | 2.220 | 2.111 | n/a |
| III | CO-Zr | 2.277 | 2.284 | 2.211 | n/a |
|  | NO-Zr | 2.142 | 2.249 | 2.144 | n/a |
| IIIA | CO-Zr | 2.262 | 2.281 | 2.237 | n/a |
|  | NO-Zr | 2.197 | 2.142 | 2.188 | n/a |
| IV | CO-Zr | 2.347 | 2.362 | 2.442 | n/a |
|  | NO-Zr | 2.367 | 2.229 | 2.417 | n/a |
| $Zr(1,2\text{-HOPO})_4$ | CO-Zr | 2.222 | 2.222 | 2.212 | 2.212 |
|  | NO-Zr | 2.252 | 2.252 | 2.242 | 2.242 |
| $Zr(HYDROXAMATE)_4$ | CO-Zr | 2.172 | 2.196 | 2.163 | 2.199 |
| CRYSTAL (REF[35]) | NO-Zr | 2.215 | 2.233 | 2.189 | 2.178 |

FIG. 34

|  |  | TERMINAL LIGANDS | | CENTRAL LIGANDS | |
|---|---|---|---|---|---|
| Zr-HOPO DFT | CO-Zr | 2.215 | 2.158 | 2.205 | 2.283 |
|  | NO-Zr | 2.269 | 2.326 | 2.270 | 2.223 |
| Zr-DFO$^{2+}$ DFT (HOLLAND) | CO-Zr | 2.261 | 2.254 | 2.199 | n/a |
|  | NO-Zr | 2.121 | 2.220 | 2.111 | n/a |
| Zr-DFO DFT | CO-Zr | 2.347 | 2.362 | 2.442 | n/a |
|  | NO-Zr | 2.367 | 2.229 | 2.417 | n/a |
| Zr(1,2-HOPO)$_4$ DFT | CO-Zr | 2.222 | 2.222 | 2.212 | 2.212 |
|  | NO-Zr | 2.252 | 2.252 | 2.242 | 2.242 |
| Zr(HYDROXAMATE)$_4$ CRYSTAL (GUERARD) | CO-Zr | 2.172 | 2.196 | 2.163 | 2.199 |
|  | NO-Zr | 2.215 | 2.233 | 2.189 | 2.178 |
| Zr-HOPO CRYSTAL | CO-Zr | 2.1925 | 2.2435 | 2.1816 | 2.2030 |
|  | NO-Zr | 2.1722 | 2.1957 | 2.1816 | 2.1971 |

FIG. 35

COMPOSITIONS FOR THERAPEUTICS, TARGETED PET IMAGING AND METHODS OF THEIR USE

CROSS REFERENCE TO RELATED APPLICATION

This application is a National Stage Application of PCT/US2016/051116, filed Sep. 9, 2016, which claims the benefit of and priority to U.S. Provisional Application No. 62/216,889, filed Sep. 10, 2015, the content of which is hereby incorporated by reference herein in its entirety.

GOVERNMENT SUPPORT

This invention was made with government support under CA180360, TR000457 and CA201999 awarded by the National Institutes of Health, DE-FG02-09ER16097 and DE-SC0002456 awarded by the Department of Energy, and 0965983 awarded by National Science Foundation. The government has certain rights in the invention.

FIELD

This invention relates generally to radioligands for positron emission tomography (PET) imaging. In particular embodiments, the invention relates to octadentate oxygen-bearing-chelators of $^{89}Zr$ for targeted PET imaging.

BACKGROUND

Antibodies possess high specificity and affinity for their antigens. Thus, Positron Emission Tomography (PET) using antibodies for targeting has become an important molecular imaging technique for cancer diagnosis and treatment management.

Zirconium-89 ($^{89}Zr$), a positron-emitting radionuclide, possesses good physical properties for PET imaging when paired with antibodies. For example, the 78.41 hours (hrs) or 3.3 days half-life of $^{89}Zr$ matches with the localization time of long circulating IgG antibodies. $^{89}Zr$ can be imaged for up to 7 days post injection. This time frame allows for clearance of unbound antibodies from the blood stream for improved tumor to background contrast. Further, the low energy positron of $^{89}Zr$ affords high intrinsic resolution, and $^{89}Zr$ residualizes in tumors. $^{89}Zr$ is inexpensively produced on small hospital-based cyclotrons using a commercially available $^{89}Y$ foil target. For at least these reasons, there has been increased interest and use of $^{89}Zr$ as a PET radiometal paired with antibodies over the past ten years.

Conventional clinical and pre-clinical studies use Desferrioxamine B (DFO) as a standard bifunctional ligand (also called a bifunctional chelator) for $^{89}Zr$ where one functionality allows for complexing to a radiolabel and the other allows for complexing to an antibody. Desferrioxamine B (DFO) is a siderophore that binds Fe(III) very tightly. DFO was first coupled to antibodies in the mid-1990s and complexed to $^{89}Zr$ and is now the "gold standard" for complexation of $^{89}Zr$ to antibodies. $Zr^{4+}$ is oxophilic and requires eight oxygen donor atoms to complete its coordination sphere for full stability. In certain embodiments, the chelator for $Zr^{4+}$ has one or more of the following features: (1) it is octadentate, that is, it has eight available coordinating moieties, to fully saturate the coordination sphere of $Zr^{4+}$; (2) it has hard oxygen donors to complement the hard, oxophilic $Zr^{4+}$ cation; and/or (3) it offers an appropriate sized cavity for the 0.84 Å effective ionic radius of $Zr^{4+}$. However, DFO only provides six oxygen donor atoms; the other two coordination sites are occupied by water molecules based on density functional theory (DFT) calculations (FIG. 1). Thus, the six donor oxygen atoms are not suitable to fully stabilize $^{89}Zr$ when imaging out to 7 or more days. Moreover, the water molecules can be displaced by endogenous ions in the body leading to decomposition of the $^{89}Zr$-DFO chelate. Traditional ligands such as DOTA and DTPA that provide eight donor atoms do not form stable complexes with Zr as nitrogen atoms are involved in the chelation. Thus, it has been thought that a ligand comprising eight oxygen donor binding sites would provide increased stability compared to DFO when complexed with $^{89}Zr^{4+}$.

DFO also lacks optimal biodistribution properties. For example, bone and non-target uptake of the radioisotope occurs due to release of osteophilic $^{89}Zr$ from DFO. Furthermore, the development of a selection of bifunctional ligands with different properties can expand the utility of $^{89}Zr$ into a number of different applications.

Other work has attempted to develop octadentate oxygen-bearing ligands possessing hydroxamate and terephthalamide groups. These ligands demonstrate efficient radiolabeling and improved stability compared to DFO when complexed to $^{89}Zr$ in in vitro assays. However, there has been no reporting of a ligand for $^{89}Zr^{4+}$ that has demonstrated viability in vivo for a sufficient length of time for antibody imaging. Several of these ligands require additional development and evaluation.

Therefore, there is a need to develop an improved bifunctional ligand for $^{89}Zr$ for $^{89}Zr$-antibody PET imaging by providing an improved alternative to DFO and reducing absorbed doses to healthy tissues to increase safer PET imaging and enhanced image quality. To this end, there is a need for a bifunctional ligand that is octadentate to improve the stability of the ligand-$^{89}Zr$ complex.

SUMMARY

Described herein is a chelator for $^{89}Zr$ for targeted PET imaging that is an alternative to DFO. In certain embodiments, the alternative chelator for $^{89}Zr$ is the ligand, 3,4,3-(LI-1,2-HOPO) ("HOPO"), which exhibits equal or superior stability compared to DFO in chemical and biological assays across a period of several days in vivo. As shown in FIG. 1, the ligand comprises HOPO, an octadentate chelator that stabilizes chelation of $^{89}Zr$. Such a ligand can eliminate $^{89}Zr$ loss from the chelate in vivo and reduce uptake in bone and non-target tissue.

As described herein, a combination of density functional theory (DFT) calculations, in vitro and in vivo stability studies, competition studies with EDTA and metal challenges, and X-ray crystal structure analysis demonstrate the advantages of an octa-coordinate zirconium complex. $Zr^{4+}$ is shown to preferentially form complexes with eight oxygen donors contained within four hydroxypyridinone groups. In certain embodiments, the ligand includes secondary functionality that comprises a functional moiety capable of complexing with an antibody. In certain embodiments, such a bifunctional HOPO ligand has decreased release and accumulation in bone and improved PET imaging with $^{89}Zr$-labeled antibodies. Moreover, as discussed herein, challenges in the synthesis of an octadentate chelator are overcome.

In one aspect, the invention is directed to a composition, the composition comprising: an oxygen-bearing ligand comprising at least 8 coordination oxygens; and a radiolabel associated with the oxygen-bearing ligand, the radiolabel selected from the group consisting of $^{89}$Zr, $^{44}$Sc, $^{47}$Sc, $^{68}$Ga, $^{177}$Lu, $^{227}$Th, $^{166}$Ho, $^{90}$Y, $^{153}$Sm, $^{149}$Pm, $^{161}$Tb, $^{169}$Er, $^{175}$Yb, $^{161}$Ho $^{167}$Tm, $^{142}$Pr, $^{143}$Pr, $^{145}$Pr, $^{149}$Pr, $^{150}$Eu, $^{159}$Gd, $^{165}$Dy, $^{176m}$Lu, $^{179}$Lu, $^{142}$La, $^{150}$Pm, $^{156}$Eu, $^{157}$Eu, and $^{225}$Ac. In certain embodiments, the composition comprises, a plurality of radiolabels (e.g., two or more members selected from the group consisting of $^{89}$Zr, $^{44}$Sc, $^{68}$Ga, $^{177}$Lu, $^{227}$Th, $^{225}$Ac, $^{166}$Ho, $^{90}$Y, $^{153}$Sm, $^{149}$Pm, $^{161}$Tb, $^{169}$Er, $^{175}$Yb $^{161}$Ho, $^{167}$Tm, $^{142}$Pr, $^{143}$Pr, $^{145}$Pr, $^{149}$Pr, $^{150}$Eu, $^{159}$Gd, $^{165}$Dy, $^{176m}$Lu, $^{179}$Lu, $^{142}$La, $^{150}$Pm, $^{156}$Eu, $^{157}$Eu, and $^{47}$Sc).

In certain embodiments, the oxygen-bearing ligand comprises a member selected from the group consisting of an octadentate oxygen-bearing ligand, a nonadentate oxygen-bearing ligand, and a decadentate oxygen-bearing ligand. In certain embodiments, the oxygen-bearing ligand comprises a hydroxypyridinone (HOPO) group. In certain embodiments, the oxygen-bearing ligand comprises a catechol group. In certain embodiments, the oxygen-bearing ligand is 3,4,3-(linear(LI)-1,2-HOPO).

In certain embodiments, the composition has a pKa value less than 14. In certain embodiments, the composition has a pKa value less than 13.

In certain embodiments, the composition comprises:

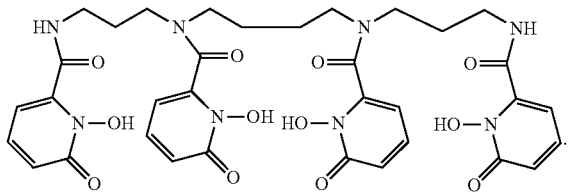 [SMILES: O=C(NCCCN(CCCCN(CCCNC(=O)c1cccc(=O)n1O)C(=O)c1cccc(=O)n1O)C(=O)c1cccc(=O)n1O)c1cccc(=O)n1O]

In certain embodiments, the composition comprises:

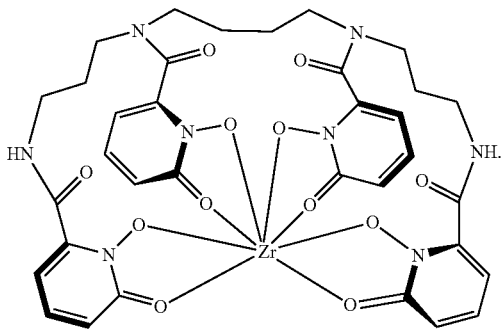

In another aspect, the invention is directed to a composition, comprising: an oxygen-bearing ligand comprising at least 8 coordination oxygens; a radiolabel associated with the oxygen-bearing ligand; a spacer between the oxygen-bearing ligand and a conjugation functionality; and the conjugation functionality, wherein the conjugation functionality comprises a moiety for association of the oxygen-bearing ligand with a targeting agent.

In certain embodiments, the oxygen-bearing ligand is any one of the ligands described herein.

In certain embodiments, the spacer comprises a member selected from the group consisting of an alkyl chain, a polylysine, a poly(amino acid) chain, and a polyethylene glycol chain. In certain embodiments, the spacer is attached at a location of the bifunctional ligand selected from the group consisting of position N1, C2, C3, C4, N5, C6, and C7 of the composition. In certain embodiments, the spacer is from 1 carbon to 50 carbons in length. In certain embodiments, the spacer is from 1 carbon to 30 carbons in length.

In certain embodiments, the conjugation functionality comprises a member selected from the group consisting of maleimide, benzyl-isothiocyanate and N-hydroxysuccinimide activated ester.

In certain embodiments, the the targeting agent is an antibody. In certain embodiments, the antibody is a member selected from the group consisting of trastuzumab, rituximab, gemtuzumab ozogamicin, alemtuzumab, ibritumomab tiuxetan, tositumomab, cetuximab, bevacizumab, panitumomab, J591, B43.13, AR9.6, 3F8, 8H9, huA33, and 5B1.

In certain embodiments, the composition has a specific activity of at least 2 mCi/mg.

In certain embodiments, the composition is at least 80% stable in serum for at least 7 days. In certain embodiments, the composition is at least 90% stable in serum for at least 7 days.

In certain embodiments, a precursor moiety used in the synthesis of the bifunctional ligand comprises the conjugation functionality.

In certain embodiments, the ligand comprises:

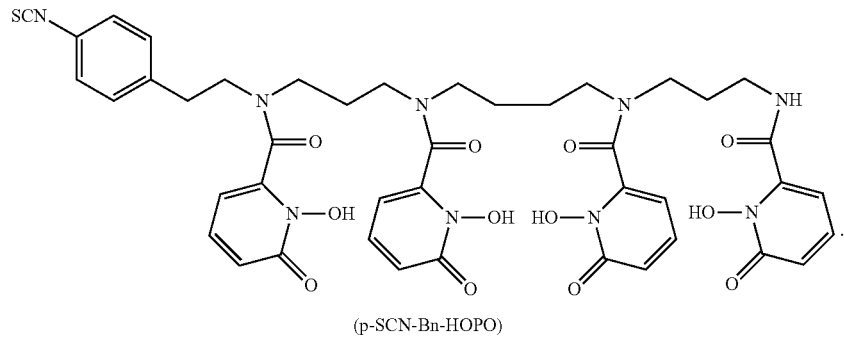

(p-SCN-Bn-HOPO)

In certain embodiments, the targeting agent is an antibody and the antibody is associated with the composition (e.g., the composition is useful for targeted PET imaging and/or radioimmunotherapy). In certain embodiments, the antibody is a member selected from the group consisting of trastuzumab, rituximab, gemtuzumab ozogamicin, alemtuzumab, ibritumomab tiuxetan, tositumomab, cetuximab, bevacizumab, panitumomab, J591, B43.13, AR9.6, 3F8, 8H9, huA33, and 5B1. In certain embodiments, the antibody is associated with any of the bifunctional ligands described herein via the conjugation functionality and the spacer.

In certain embodiments, the composition comprising a bifunctional ligand further comprises $^{177}$Lu and/or $^{89}$Zr.

In certain embodiments, the spacer is attached at a location selected from the group consisting of position N1, C2, C3, C4, N5, C6, and C7 of the composition.

In another aspect, the invention is directed to a method for detecting tumor cells, the method comprising: administering a quantity of any of the compositions described herein to a subject, wherein a portion of the quantity localizes at the tumor cells and a sufficient portion of unbound composition is cleared after a time interval (e.g., sufficient to permit imaging without interference from unbound composition); and imaging the composition accumulated in a region of the subject within a time period no longer than 336 hours from the administering of the quantity of the composition.

In certain embodiments, the tumor cells are cells that express at least one marker of at least one of prostate cancer, lung cancer, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, Wilm's tumor, or combinations thereof.

In certain embodiments, the composition comprises p-SCN-Bn-HOPO and trastuzumab. In certain embodiments, the bifunctional ligand comprises p-SCN-Bn-HOPO.

In certain embodiments, the method comprises administering the quantity of the composition to the subject by injection.

In certain embodiments, the composition is cleared from a member selected from the group consisting of a renal system, a fecal system, and from the subject.

In certain embodiments, the time interval is no longer than 336 hours.

In certain embodiments, the method comprises imaging performed via positron emission tomography (PET) imaging. In certain embodiments, the imaging of the composition accumulated in a region of the subject is within a time period not longer than 336 hours from the administering of the quantity of composition.

In certain embodiments, the bifunctional ligand prevents more than minimal accumulation of the composition or any portion of the composition in bone of the subject.

In certain embodiments, accumulation of the complex is less than 5% ID/g.

In certain embodiments, the composition comprises p-SCN-Bn-HOPO and trastuzumab.

In certain embodiments, the bifunctional ligand comprises:

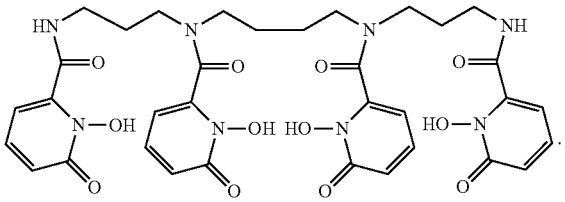 [SMILES: O=C(NCCCN(CCCCN(CCCNC(=O)c1cccc(=O)n1O)C(=O)c1cccc(=O)n1O)C(=O)c1cccc(=O)n1O)c1cccc(=O)n1O]

In certain embodiments, the composition comprises at least one europium(III) and/or other lanthanide ion.

In certain embodiments, the method comprises: directing light to excite at least one group in the oxygen-bearing ligand of the composition; detecting light emitted from the at least one europium(III) and/or other lanthanide ion.

In certain embodiments, the directed light has a wavelength from 300 nm to 400 nm.

In certain embodiments, the at least one group comprises at least one hydroxypyridinone group.

In certain embodiments, the detected light comprises light in the visible and/or near infrared range.

In another aspect, the invention is directed to a method for imaging comprising: administering a quantity of a composition comprising any of the compositions described herein and at least one fluorescent lanthanide ion to a subject, wherein a portion of the quantity localizes at the tumor cells and a sufficient portion of unbound composition is cleared after a time interval; directing light to excite at least one moiety in the composition; and detecting light emitted from the at least one fluorescent lanthanide ion.

In certain embodiments, the fluorescent lanthanide ion comprises europium(III).

In certain embodiments, the directed light has a wavelength from 300 nm to 400 nm.

In certain embodiments, the at least one group comprises at one or more hydroxypyridinone groups. In certain embodiments, the at least one group comprises at one or more catechol groups.

In certain embodiments, the bifunctional ligand comprises p-SCN-Bn-HOPO.

In certain embodiments, the method comprises the composition having accumulated in tumor cells in a subject following administration of the composition to the subject.

In certain embodiments, the directing light and detecting light are performed within a time period not longer than 336 hours. In certain embodiments, the method is performed within a time period not longer than 216 hours from the administration of the composition.

In certain embodiments, the detected light comprises light in the visible and/or near infrared range.

In another aspect, the invention is directed to a method of treatment of a subject, the method comprising the step of administering to the subject a quantity of any of the compositions described herein, wherein the composition comprises $^{177}$Lu and a portion of the quantity associates with one or more tumor cells in the subject.

In certain embodiments, the tumor cells are cells that express at least one marker of at least one of prostate cancer, lung cancer, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, Wilm's tumor, or combinations thereof.

In certain embodiments, the composition comprises p-SCN-Bn-HOPO and trastuzumab.

In certain embodiments, the administering comprises injecting the quantity of the composition to the subject.

In certain embodiments, the method comprises imaging the composition accumulated in a region of the subject within a time period no longer than 336 hours from the administering of the quantity of the composition.

In certain embodiments, the imaging is performed via positron emission tomography (PET) imaging.

In certain embodiments, a sufficient portion of the composition that did not associate with one more tumor cells is cleared after a time interval and the sufficient portion is cleared from a member selected from the group consisting of a renal system, a fecal system, and from the subject.

In certain embodiments, the time interval is no longer than 336 hours.

In another aspect, the invention is directed to a method comprising step (f) as follows: coupling a compound of formula 6A:

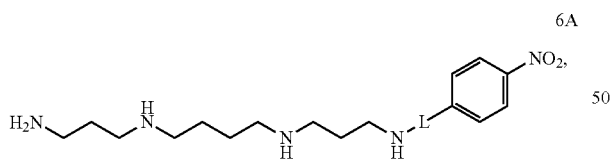

6A or a salt thereof, with a compound of formula 6B:

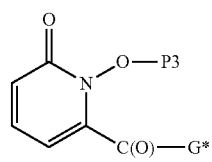

6B wherein —C(O)-G* is a moiety suitable for coupling to an amine, to form a compound of formula 7A:

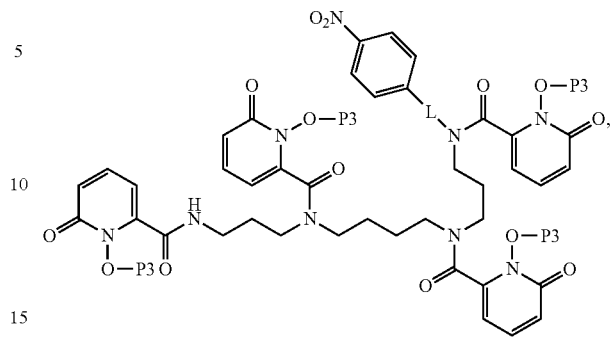

7A wherein L is a linker (e.g., an alkyl chain, a polylysine chain, a poly(amino acid) chain, a polyethylene glycol chain), and P3 is an oxygen-protecting group.

In certain embodiments, the method further comprises: step (g) as follows: reducing the compound of formula 7A to a compound of formula 8A:

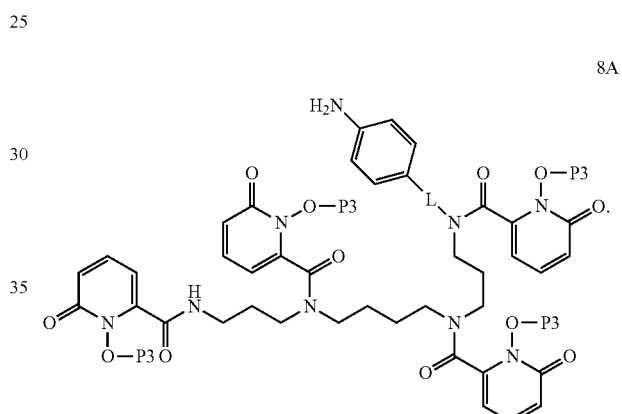

8A

In certain embodiments, the method further comprises step (h) as follows: deprotecting the compound of formula 8A to form a compound of formula 9A:

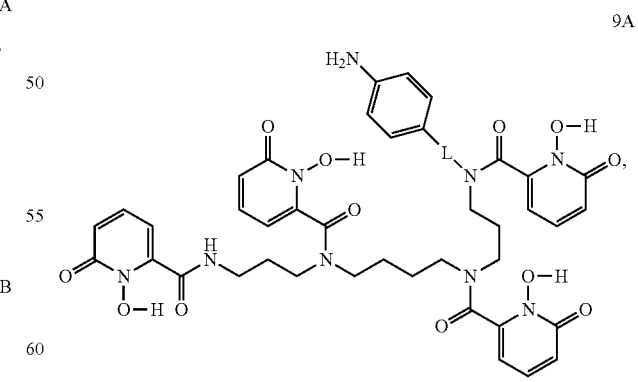

9A or a salt thereof.

In certain embodiments, the method further comprises step (i) as follows: converting the compound of formula 9A to a compound of formula 10A:

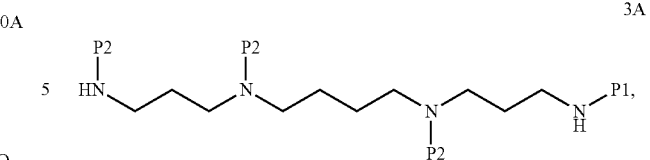

wherein P1 is an amine-protecting group, to form the compound of formula 4A.

In certain embodiments, the method further comprises, prior to step (c), step (b) as follows: protecting a compound of formula 2A:

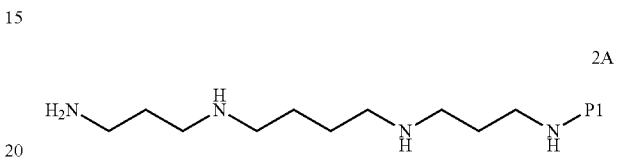

to form the compound of formula 3A.

In certain embodiments, the method further comprises, prior to step (b), step (a) as follows: protecting a compound of formula 1A:

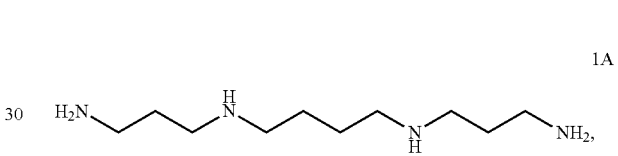

to form the compound of formula 2A.

In certain embodiments, L is —$(CH_2)_{1-8}$—.

In certain embodiments, L is —$(CH_2CH_2)$—. In certain embodiments, P3 is benzyl. In certain embodiments, —C(O)-G* is —C(O)—Cl. In certain embodiments, —OC(O)—$C(CH_3)_3$. In certain embodiments, L* is —$(CH_2)_{1-8}$—Br. In certain embodiments, L* is —$(CH_2CH_2)$—Br. In certain embodiments, P1 is —C(O)—$CF_3$.

Elements of embodiments involving one aspect of the invention (e.g., methods) can be applied in embodiments involving other aspects of the invention, and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

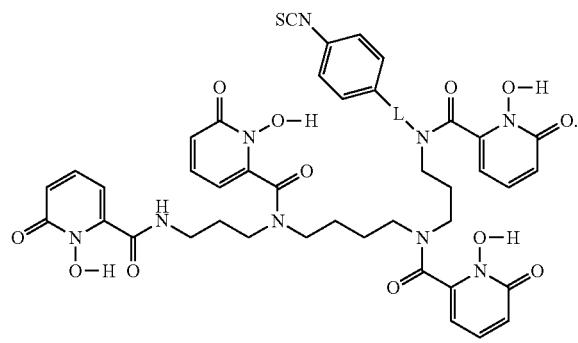

In certain embodiments, the method further comprises, prior to step (f), step (e) as follows: deprotecting a compound of formula 5A:

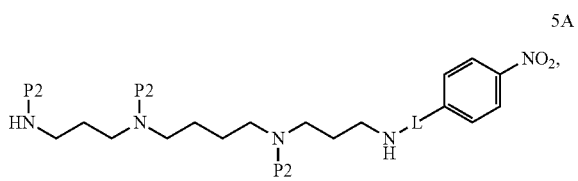

wherein P2 is an amine-protecting group, to form the compound of formula 6A, or a salt thereof.

In certain embodiments, the method further comprises prior to step (e), step (d) as follows:

coupling a compound of formula 4A

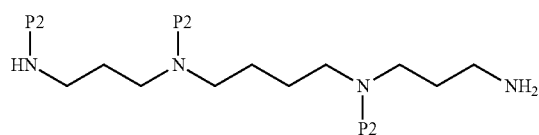

with a compound of formula 4B:

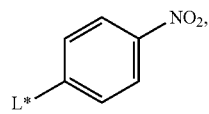

wherein L* is a moiety suitable for coupling to an amine, to form the compound of formula 5A.

In certain embodiments, the method further comprises, prior to step (d), step (c) as follows: deprotecting a compound of formula 3A:

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

"Associated": Two or more entities are "associated" with one another if they interact, directly or indirectly, so that they are and/or remain in physical proximity with one another. In some embodiments, two or more entities that are associated with one another are covalently linked to one another; in some embodiments, two or more entities that are associated with one another are not covalently linked to one another but are non-covalently associated, for example, by means of hydrogen bonds, van der Waals interaction, hydrophilic/hydrophobic interactions, magnetism, and combinations thereof.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects.

"Radiolabel": As used herein, "radiolabel" refers to a moiety comprising a radioactive isotope of at least one element. Exemplary suitable radiolabels include but are not limited to those described herein. In some embodiments, a radiolabel is one used in positron emission tomography (PET). In some embodiments, a radiolabel is one used in single-photon emission computed tomography (SPECT). In some embodiments, a radiolabel is one used for radioimmunotherapy. In some embodiments, radioisotopes comprise one or more members selected from the group consisting of $^{99m}Tc$, $^{111}In$, $^{64}Cu$, $^{67}Ga$, $^{68}Ga$, $^{186}Re$, $^{188}Re$, $^{153}Sm$, $^{176m}Lu$, $^{177}Lu$, $^{67}CU$, $^{123}I$, $^{124}I$, $^{125}I$, $^{11}C$, $^{13}N$, $^{15}O$, $^{18}F$, $^{186}Re$, $^{188}Re$, $^{47}Sc$, $^{44}Sc$, $^{161}Ho$, $^{166}Ho$, $^{90}Y$, $^{149}Pm$, $^{90}Y$, $^{213}Bi$, $^{103}Pd$, $^{109}Pd$, $^{159}Gd$, $^{140}La$, $^{142}La$, $^{198}Au$, $^{199}Au$, $^{169}Yb$, $^{175}Yb$, $^{165}Dy$, $^{166}Dy$, $^{161}Tb$, $^{105}Rh$, $^{111}Ag$, $^{89}Zr$, $^{225}Ac$, $^{169}Er$, $^{167}Tm$, $^{142}Pr$, $^{143}Pr$, $^{145}Pr$, $^{149}Pr$, $^{150}Eu$, $^{150}Pm$, $^{156}Eu$, $^{157}Eu$, $^{134}Ce$, $^{140}Nd$, $^{140}Pr$, $^{134}La$ and $^{192}Ir$.

"Subject": As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals can be, for example, rodents (e.g., mice, rats, hamsters), rabbits, primates, or swine such as inbred pigs and the like. In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

"Therapeutic agent": As used herein, the phrase "therapeutic agent" refers to any agent that has a therapeutic effect and/or elicits a desired biological and/or pharmacological effect, when administered to a subject. In some embodiments, a therapeutic agent comprises a radiolabel for radiation-based therapy (e.g., radiotherapy).

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

BRIEF DESCRIPTION OF DRAWINGS

Drawings are presented herein for illustration purposes, not for limitation. The foregoing and other objects, aspects, features, and advantages of the present disclosure can become more apparent and better understood by referring to the following description taken in conduction with the accompanying drawings, in which:

FIG. 7 shows the stability of $^{89}Zr$-HOPO and $^{89}Zr$-DFO against competition by other metals. The radiolabeled complexes were incubated in an excess of other metal salts at 37° C. over 7 days. The only metal that destabilized the Zr out of the chelator was $Fe^{3+}$. Both hydroxamates and hydroxypyridinones have an affinity for iron and DFO is a natural siderophore. Still, in the case of $Fe^{3+}$, the $^{89}$Zr-HOPO complex stays more intact compared to the $^{89}$Zr-DFO complex by a factor of 2.

FIG. 19 shows DOTA and HOPO radiolabeled with $^{177}$Lu and then incubated in a 10-fold excess of various metal salts at 35° C. at a pH of 7.4 in order to test for metal ion replacement.

FIG. 34 shows DFT bond distances. Zr—O bond distances are shorter in the $^{89}$Zr-HOPO complexes than in the $^{89}$Zr-DFO complexes. All lengths are reported in Angstroms.

FIG. 35 shows bond distance comparison between $^{89}$Zr-HOPO complexes and the $^{89}$Zr-DFO complexes. All lengths are reported in Angstroms.

DETAILED DESCRIPTION

Throughout the description, where compositions are described as having, including, or comprising specific components, or where methods are described as having, including, or comprising specific steps, it is contemplated that, additionally, there are compositions of the present disclosure that consist essentially of, or consist of, the recited components, and that there are methods according to the present disclosure that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Figure 1:
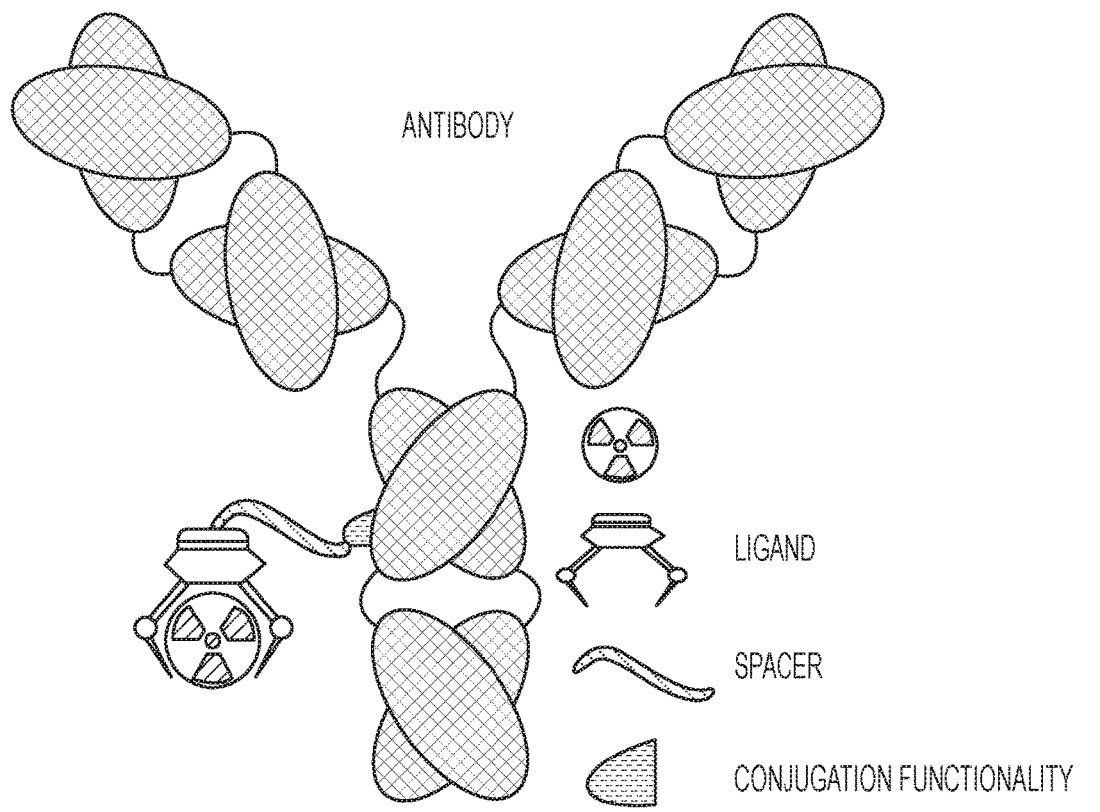
FIG. 1 shows components of a bifunctional ligand (e.g., a ligand or chelator that binds the radiometal, a spacer to separate the ligand from the antibody and the chemical functionality to link the spacer to the antibody) and structures of $^{89}Zr$-HOPO and $^{89}Zr$-DFO that depict the 8-coordination compared to 6-coordination with 2 water molecules, respectively.
Figure 1:
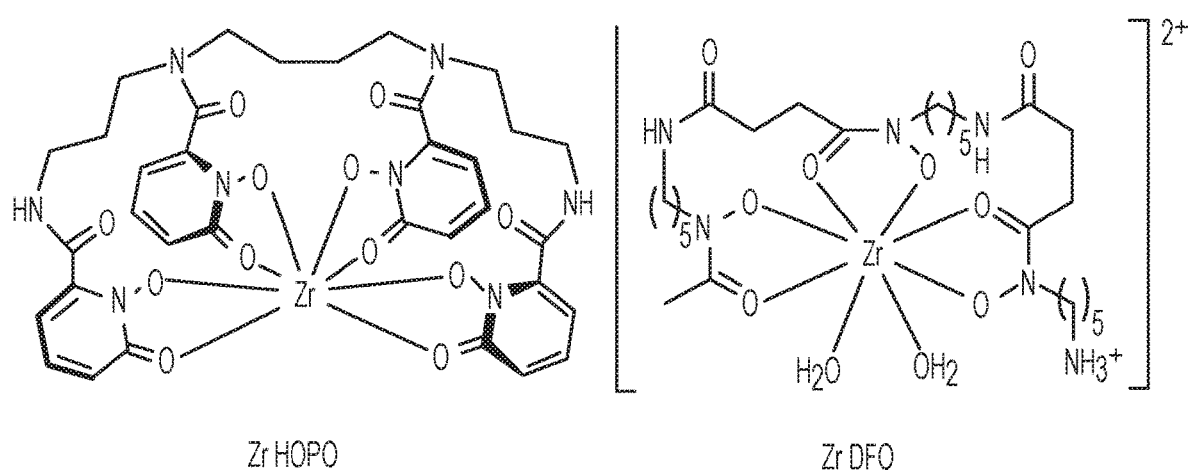

Described herein is a chelator for a radiometal (e.g., $^{89}$Zr) for targeted PET imaging that is an alternative to DFO. In certain embodiments, the alternative chelator for $^{89}$Zr is the ligand, 3,4,3-(LI-1,2-HOPO) ("HOPO"), which exhibits equal or superior stability compared to DFO in chemical and biological assays across a period of several days in vivo. As shown in FIG. 1, the ligand comprises HOPO, an octadentate chelator that stabilizes chelation of $^{89}$Zr. Such a ligand can eliminate $^{89}$Zr loss from the chelate in vivo. In certain embodiments, the ligand includes secondary functionality that is or comprises a functional moiety capable of complexing with a targeting agent (e.g., an antibody) for specific binding of the ligand-radiolabel complex to a desired site in a subject. Such a bifunctional ligand could reduce uptake in bone and non-target tissue by using selective targeting agents that target cells expressing certain moieties (e.g., proteins). The chelators described herein are biocompatible and can be used, for example, in in vivo imaging of a subject.

As described herein, a combination of density functional theory (DFT) calculations, in vitro and in vivo stability studies, competition studies with EDTA and metal challenges, and X-ray crystal structure analysis demonstrate the advantage of an octa-coordinate zirconium complex. $Zr^{4+}$ is shown to preferentially form complexes with eight oxygen donors contained within four hydroxypyridinone groups. The HOPO ligand has decreased release of $^{89}$Zr and, in certain embodiments, decreased accumulation in bone and improved PET imaging with $^{89}$Zr-labeled antibodies.

Zr(IV) chemistry is similar to plutonium (IV) ($Pu^{4+}$) chemistry. Therefore, as described herein, ligands designed for in vivo Pu(IV) chelation therapy were developed for use with $^{89}$Zr. Ligands with low pKa values resulting from the hydroxypyridinone functionalities in HOPO were selected as they facilitate binding at physiological pH, and their linear structure resulted in fast kinetics of $^{89}$Zr$^{4+}$ labeling at room temperature (RT).

Although HOPO is superior to DFO in Zr chemistries due to at least the reasons stated above, there are other considerations in creating an optimized bifunctional ligand as shown in FIG. 1. For example, the ligand portion has been optimized for stability of $^{89}$Zr with the HOPO ligand and is described below. Parameters that can be optimized include: the position on the HOPO chain for attachment of a spacer; the spacer that should provide sufficient space between the ligand and a site of attachment to an antibody so that the radiometal can approach the ligand without interference of the antibody. Third, a conjugation functionality influences the stability, solubility, and reactivity of the bifunctional ligand as well as the stability of the resulting ligand-antibody complex.

As described herein, the HOPO ligand labeled $^{89}$Zr efficiently and with specific activity comparable to DFO. $^{89}$Zr-HOPO exhibited equal or superior stability compared to DFO in all chemical and biological assays. Collectively, octadentate oxygen-bearing ligands provide stable $^{89}$Zr complexes for the development of bifunctional ligands.

Development of an Improved Bifunctional Chelate Based on Chemistry of Zr

The complexity of aqueous Zr chemistry presents challenges to isolate and assess comparative stabilities of macroscopic Zr-HOPO complexes with the linker attached. Therefore, DFT calculations were performed to identify the impact of the position of the spacer in the HOPO chain on the stability and coordination of the overall Zr complexes was added. Inclusion of molecular dynamics simulations of the bifunctional ligand conjugated to the antibody can interrogate the availability of the ligand for radiometal complexation. Aspects of the present disclosure (e.g., synthesis, theory, radiolabeling, stability assays, biodistribution and imaging) provide a blueprint for ligand development for chelation of radiometals.

Density functional theory (DFT) calculations were performed to predict the most stable configurations of the Zr-ligand binding and provide strategies for alternative ligand design. The optimized $^{89}$Zr-HOPO structure was found to be 31.8 kcal/mol more stable than $^{89}$Zr-DFO.

The bifunctional ligands described herein possess linkers of different sizes and solubilities and two different conjugation chemistries. In certain embodiments, selected bifunctional ligands provide optimized pharmacokinetics when conjugated to nanoparticles (e.g., cross-linked, short chain dextran nanoparticles or gold nanoparticles that are subsequently radiolabeled with $^{89}$Zr for PET imaging).

Figure 2:
FIG. 2 shows DFO and HOPO radiolabeled with $^{89}Zr$ and then incubated in a 50-fold excess of EDTA at 37° C. and various pHs in order to test for transchelation, or if excess EDTA can strip the $^{89}Zr$ out of the ligands over time.

A chelator for $^{89}$Zr: 3,4,3-(LI-1,2-HOPO) or HOPO is described in Deri et al. "Alternative chelator for $^{89}$Zr radiopharmaceuticals: radiolabeling and evaluation of 3,4,3-(LI-1,2-HOPO). J Med Chem. 2014; 57(11):4849-60.", the contents of which are hereby incorporated by reference in its entirety. As described therein, an octadentate, oxygen-rich ligand for better chelation of zirconium was compared to hexadentate DFO. In order to initially test the HOPO ligand, the ligand itself, without any bifunctional linker, was synthesized. The HOPO ligand outperformed or matched DFO, with the most extreme difference being the markedly improved stability of $^{89}$Zr-HOPO to transchelation by EDTA, especially at lower pH (FIG. 2).

In certain embodiments, libraries of bifunctional ligands with differing properties can expand the utility of $^{89}$Zr into a number of different applications. For example, a library of bifunctional HOPO ligands varying the position where the linker is attached to the HOPO backbone, the length and composition of the spacer between the ligand and point of conjugation to the antibody, and the chemical functionality for conjugation to an antibody can be synthesized. The synthetic effort can be paired with DFT calculations and molecular dynamics simulations to investigate the solution phase behavior of the unmetallated bifunctional chelator, model the Zr(IV) coordination environment and compare the relative stabilities of the complexes in silico.

Figure 3:
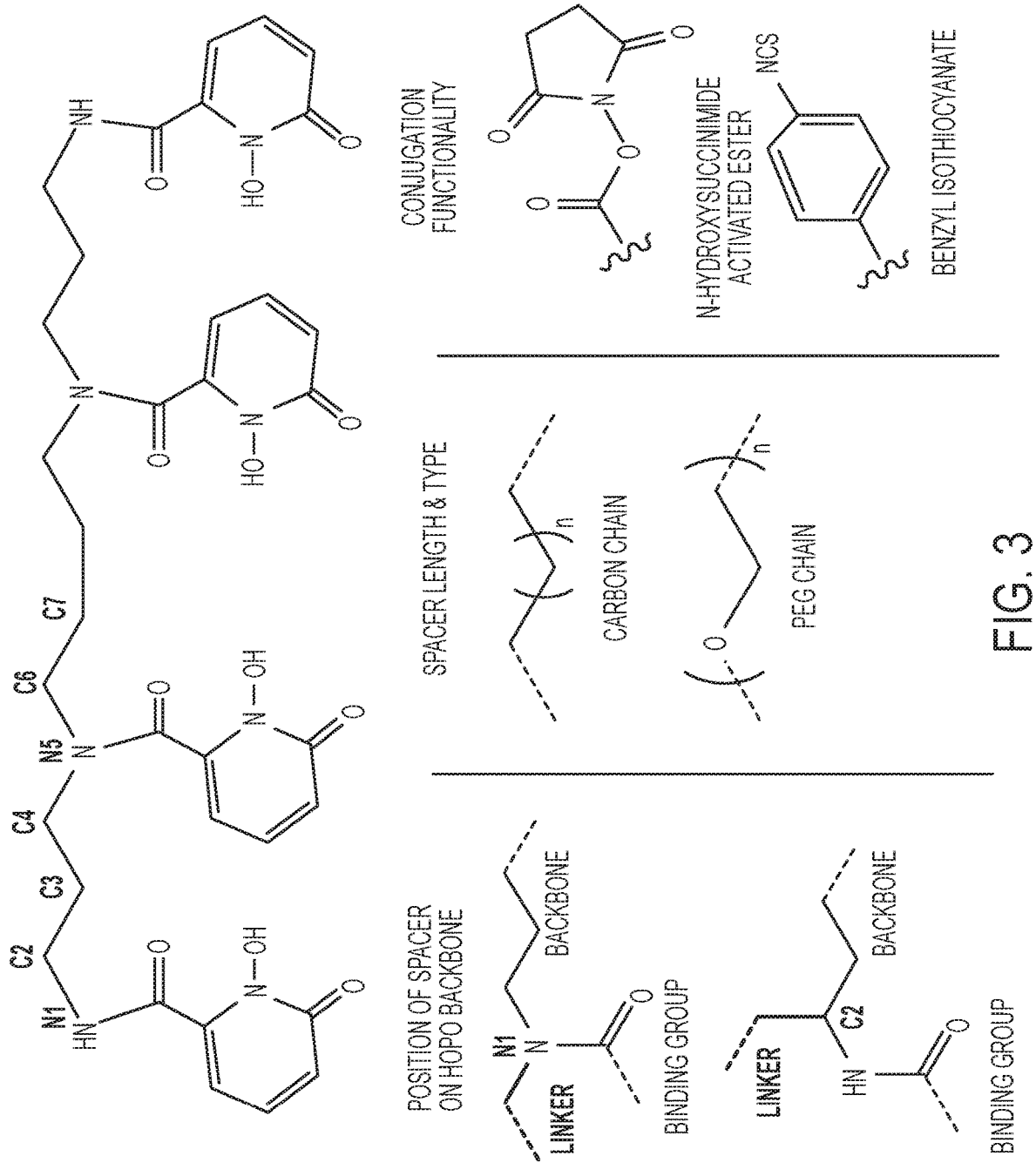
FIG. 3 shows exemplary varied components for a library of bifunctional 3,4,3-(LI-1,2-HOPO) ligands.

Due to the results from 3,4,3-(LI-1,2-HOPO) ligand alone, it was expected that the initial bifunctional derivative p-SCN-Bn-HOPO conjugated to trastuzumab (p-SCN-Bn-HOPO-Tz) would exhibit efficient radiolabeling and high specific activity. In certain embodiments, trastuzumab is chosen as an antibody for its usefulness in associating with breast cancer cells. However, it was observed that p-SCN-Bn-HOPO-Tz does not label as effectively as p-SCN-Bn-DFO-Tz and the specific activity was slightly lower. Without wishing to be bound to any theory, it was hypothesized that the difference in performance was due to the choice of linker used to attach the ligand to an antibody. Therefore, in certain embodiments of the present disclosure, a library of bifunctional variants of 3,4,3-(LI-1,2-HOPO) can be created by using different linker chemistries in order to discover the optimal bifunctional ligand. The library can vary the position where the linker is attached to the ligand, the length and composition of the spacer between the ligand and the point of conjugation, and the chemical functionality included for conjugation to an antibody (FIG. 3). By systematically varying these components of the bifunctional ligand, the properties of the ligand can be fine-tuned and thus provide a selection of optimized ligands for specific applications. The synthetic procedure developed for p-SCN-Bn-HOPO (FIG. 4) can serve as the framework for the synthesis of all of the proposed ligand variants.

There are seven unique positions along the backbone of the HOPO ligand (marked N1-C7 in FIG. 3). Through various chemistries, it is possible to introduce the linker into several of these positions. Of foremost interest are positions N1 and C2 as shown in FIG. 3 due to commercial availability of reagents and synthetic convenience. The point of attachment of the linker to the ligand may have downstream effects on the metal binding regions of the ligand by altering electron densities or more likely by causing steric or conformational hindrances near the binding site. In combination with synthetic efforts, DFT calculations can allow determination of comparative stabilities of the bifunctional ligands in silico.

The spacer connects the ligand to the functional group which conjugates to the antibody. Both its length and its chemical makeup can be altered to vary bifunctional ligand performance. The length of the spacer largely controls the proximity of the metal binding region of the ligand from the antibody. Too short of a spacer may not leave room for a metal to approach the ligand while too long of a spacer may introduce instability or an opportunity for cleavage. The chemical makeup of the linker can have an effect on the solubility of the chelator. A ligand that precipitates out of solution is not likely to achieve high levels of conjugation to the antibody, while one that has the steric bulk of the ligand attached very closely to the conjugating functionality may not have the space or flexibility to access the appropriate side chains of the antibody.

The choice of functionality appended to the ligand for conjugation plays a role in determining the stability, solubility, and reactivity of the bifunctional ligand as well as the stability of the resulting ligand-antibody complex. As described herein, without exclusion of other possible functional moieties, the initial focus of functionality for conjugation to an antibody has been a benzyl isothiocyanate. This is due to its ease of use and so that the completed bifunctional ligand can be directly compared to the most commonly used DFO derivative: p-SCN-Bn-DFO. In addition to benzyl isothiocyanate, N-hydroxysuccinimide activated esters as an additional conjugation route can also be considered (FIG. 3).

To this end, altering the two different points of attachment (N1 and C2), three different types of spacers (e.g., a carbon chain, a polylysine chain, and a PEG chain), two different spacer lengths (e.g., short and long), and two different conjugation chemistries, the library, in this example, can comprise 16 different bifunctional chelators. In certain embodiments, variants of the isothiocyanate based bifunctional ligand can be made and improvements of the system can be evaluated. DFT calculations and molecular dynamics simulations can be pursued along with ligand synthesis and evaluation to provide comparative stabilities of the $^{89}$Zr chelates and to understand the impact of spacer on radiolabeling, respectively.

Synthesis and Characterization of p-SCN-Bn-HOPO

Figure 4:
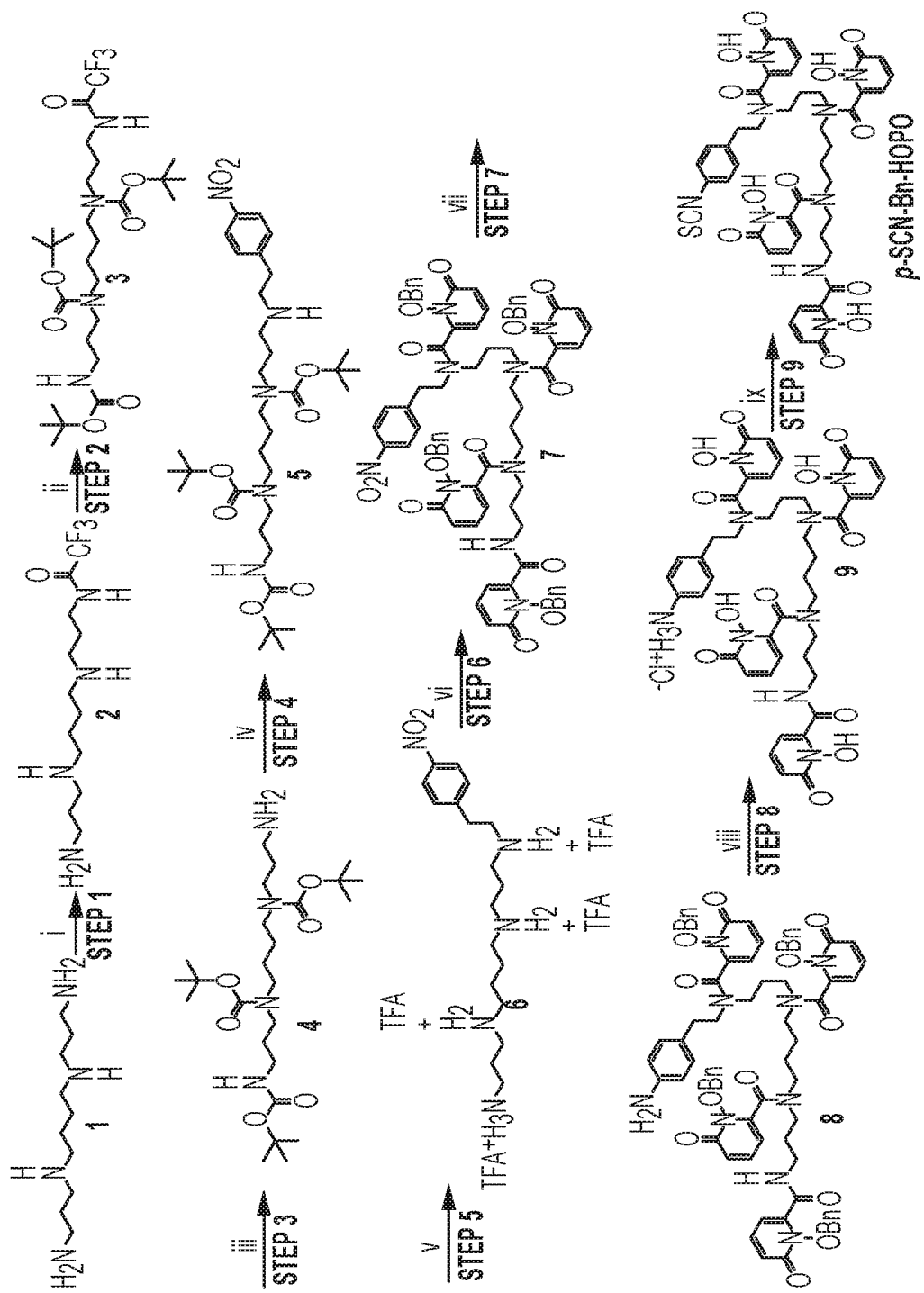
FIG. 4 shows synthesis of p-SCN-Bn-HOPO (i) Ethyl trifluoroacetate, MeOH, −40° C., 3 h, 30%; (ii) (BOC)$_2$O, MeOH, r.t, 12 h, 83%; (iii) aq K$_2$CO$_3$, r.t 6 h, 42%; (iv) 4-Nitro phenylethyl bromide, K$_2$CO$_3$, DMF, 60° C., 12 h, 38%; (v) TFA:DCM (1:1), r.t, 2 h, 86%; (vi) 1-(benzyloxy)-6-oxo-1,6-dihydropyridine-2-carboxylic acid chloride, NEt$_3$, DCM, 0° C.-r.t, 12 h, 56%; (vii) SnCl$_2$.2H$_2$O, EtOH, 90° C., 2 h, 70%; (viii) 1:1 (AcOH: HCl), 50° C. ix) 2-dipyridyl thiocarbonate, NEt$_3$, CH$_3$CN, H$_2$O, r.t, 1 h).
Figure 5:
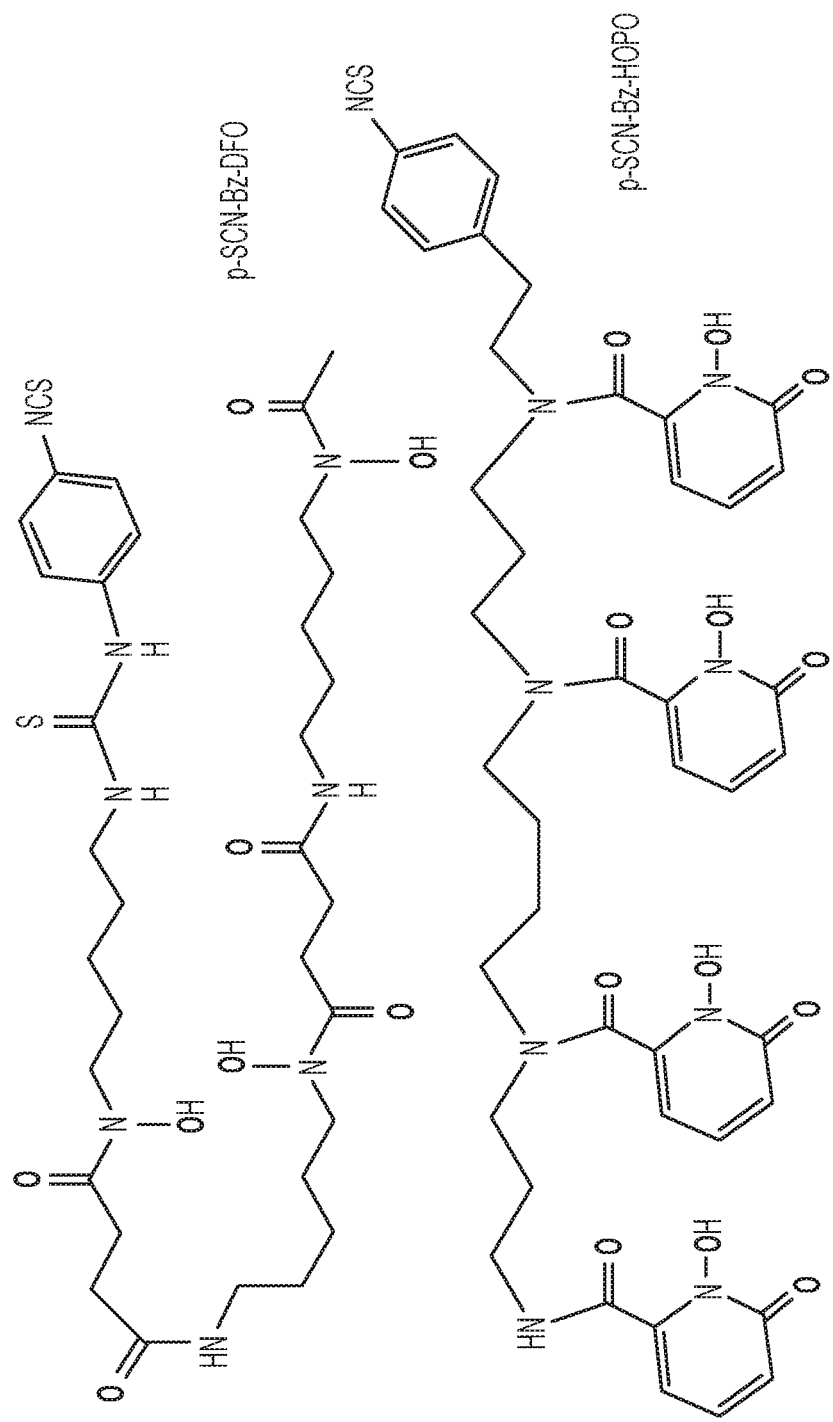
FIG. 5 shows a schematic of the chemical structures of p-SCN-Bn-DFO and p-SCN-Bn-HOPO. The metal binding oxygens are highlighted in red.

The 3,4,3-(LI-1,2-HOPO) ligand was developed into a bifunctional variant of the HOPO ligand for further evaluation and application in antibody-based PET imaging by synthesis of the related bifunctional chelator: p-SCN-Bn-HOPO (FIG. 4, FIG. 5). In certain embodiments, a composition comprising a bifunctional ligand containing at least one HOPO or catechol group such as, but not limited to, p-SCN-Bn-HOPO further comprises a radiolabel suitable for imaging is used to image one or more cancer cells by administering the composition to a subject, performing a chosen radioimaging technique and measuring the resulting signal, comparing the resulting signal with standard values (e.g., to a previous image or reference image), finding any significant deviation during the comparison (e.g., less signal, a reduced physical dimension of the one or more cancer cells (e.g., tumor)), and subsequently making a decision regarding the comparison (e.g., that a treatment is necessary, will be effective, or has been effective). The HOPO ligand comprises a para-benzyl-isothiocyanate pendant arm added to one of the secondary amines in order to be directly comparable with the currently most used bifunctional chelator: p-SCN-Bn-DFO (FIG. 5). The creation of the bifunctional version of p-SCN-Bn-HOPO was non-trivial, as the isothiocyanate pendant arm, or linker arm, was unable to be appended to the complete ligand but instead had to be incorporated into the backbone itself. While this required a modified synthetic procedure, the bifunctional ligand has been produced as described herein (FIG. 4).

For example, initial attempts were made to attach a linker arm directly to one on the secondary amines of the original 3,4,3-(LI-1,2-HOPO) ligand in order to make it bifunctional; however, efforts were initially unsuccessful. In certain embodiments, an alternative synthesis was developed to build the ligand by incorporating at least one linker arm directly into the ligand molecule (e.g., into the backbone chain of the molecule) during synthesis (FIG. 4). In certain embodiments, this new method enables the pendant arm to be built into the backbone itself before coupling the hydroxypyridinone groups onto it. The synthesis of the bifunctional chelator proved to be challenging, with a particular difficulty in the deprotection and purification steps but was ultimately achieved. The final product, p-SCN-BN-HOPO, was purified by HPLC and characterized by NMR, IR, and HRMS.

p-SCN-BN-DFO was conjugated to antibodies through the formation of a thiourea bond with the amine sidechain of a lysine residue. The p-SCN-BN-HOPO ligand was designed to be attached in an identical protocol. Both ligands were conjugated to trastuzumab at a ratio of 5:1 ligand: antibody in the reaction mixture. The number of chelates per antibody was initially investigated by MALDI-TOF mass spectrometry; however, the error was found to be too large to provide conclusive values. Subsequently, the number of chelates per antibody was determined to be 2.0±0.5 for p-SCN-BN-DFO and 2.8±0.2 for p-SCN-BN-HOPO through a simplified isotopic dilution assay.

All compounds were radiolabeled under mild conditions using a $^{89}$Zr-oxalate solution at pH 7 and room temperature. Reaction progress was monitored using radio ITLC. First, the bifunctional chelators p-SCN-Bn-HOPO and p-SCN-BN-DFO were radiolabeled on their own without being attached to any targeting vectors in order to compare each of the bifunctional chelators Zr binding ability. Both ligands labeled quantitatively within 1 h. This confirmed that the benzyl isothiocyanate linker arm did not interfere with the metal binding. Next, the chelator-modified trastuzumab complexes were radiolabeled under the same conditions. Both complexes labeled within 1-3 h at room temperature and achieved specific activities of approximately 2 mCi/mg. Radiolabeled antibody conjugates were purified via size exclusion chromatography and spin filtration.

The viability of the $^{89}$Zr-labeled trastuzumab complexes was assayed against BT474 cells to ensure that the conjugation of the chelators did not disrupt the biologically activity of the antibody. The $^{89}$Zr-DFO-trastuzumab and $^{89}$Zr-HOPO-trastuzumab conjugates were found to have immunoreactive fractions of 88.6±2.1% and 92.4±6.8%, respectively.

The $^{89}$Zr-ligand complexes alone as well as the $^{89}$Zr-ligand-antibody complexes were evaluated for stability in human serum at 37° C. Both $^{89}$Zr-ligand complexes were stable in human serum (e.g., 97.7±0.2% of the p-SCN-Bn-DFO complex and 97.5±0.5% of the p-SCN-Bn-HOPO complex intact after 7 d). When the ligands were conjugated to trastuzumab and then labeled, both complexes demonstrated slight decreases in stability. For example, the $^{89}$Zr-DFO-tratuzumab complex showed 94.7±0.7% stability and the $^{89}$Zr-HOPO-tratuzumab complex showed stability between the $^{89}$Zr-ligand complexes. The reason for the change in stability between the $^{89}$Zr-ligand complexes and $^{89}$Zr-ligand-antibody complexes is currently unknown, but, without wishing to be bound by theory, may be due to the influence of the antibody sidechains altering the chelation environment of the metal either during radiolabeling or during the serum incubation.

Figure 6:
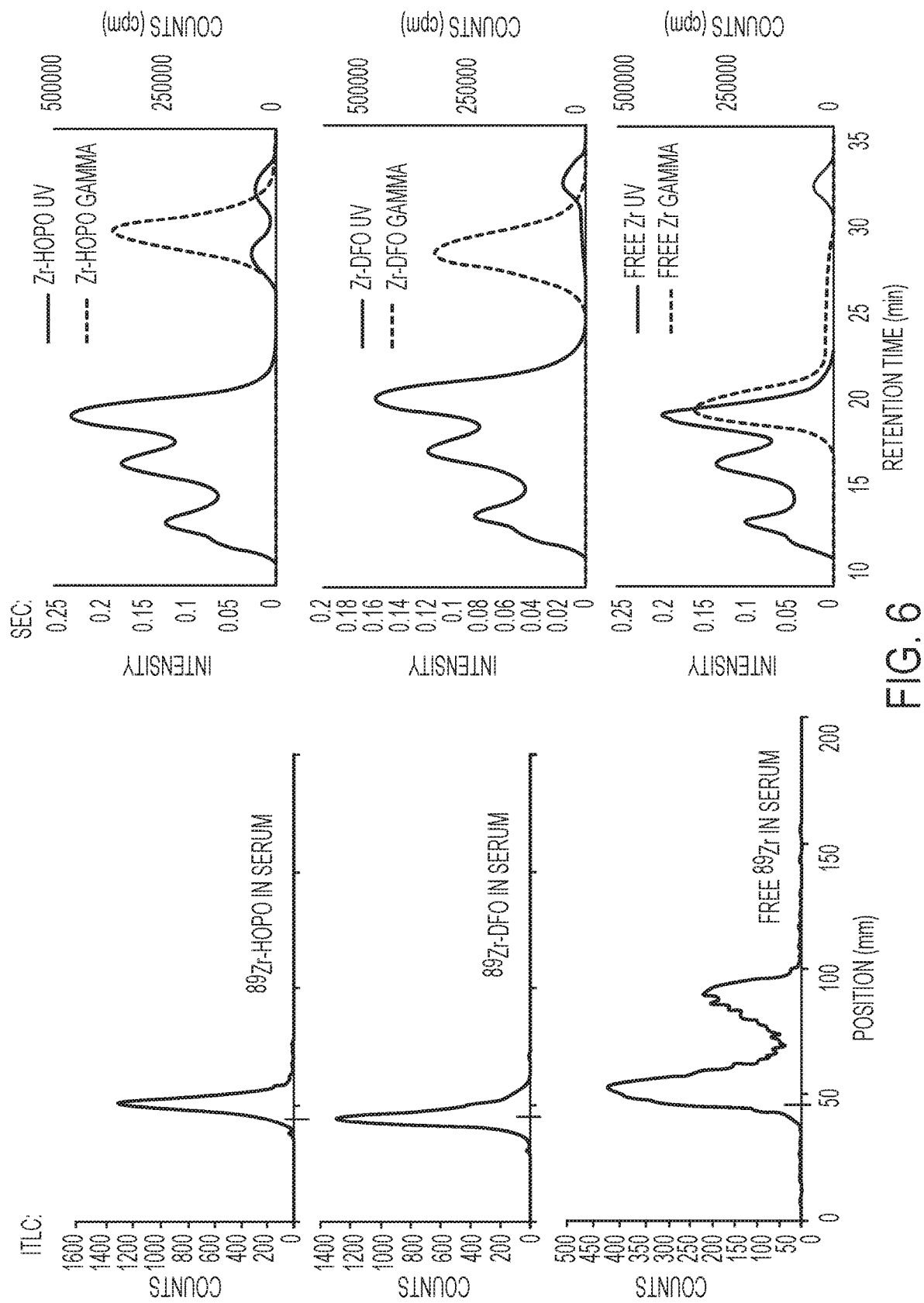
FIG. 6 shows stability of $^{89}Zr$-HOPO complex compared to $^{89}Zr$-DFO complex in serum by ITLC and SEC measurements.

As shown in FIG. 6, $^{89}$Zr-HOPO complex and the $^{89}$Zr-DFO complex were incubated in human serum at 37° C. for one week. ITLC shows that both complexes appear to remain intact over the 7 day period, which was further confirmed through size exclusion chromatography (SEC). Seven day old samples of the Zr-ligand complexes were run down a size exclusion column to differentiate protein and ligand. The solid lines correspond to the UV signal of the serum proteins as well as a small bump from the UV absorbance of the HOPO ligand itself. The dotted lines represent the radioactive signal. As shown in FIG. 6, the free $^{89}$Zr coelutes with the serum proteins whereas the Zr-ligand complexes elute about 10 minutes later corresponding to the appropriate size range for the ligand-metal complexes. This result confirms that both the $^{89}$Zr-HOPO and $^{89}$Zr-DFO complexes are stable in serum over 7 days.

FIG. 7 shows the stability of $^{89}$Zr-HOPO and $^{89}$Zr-DFO against competition by other metals. The radiolabeled complexes were incubated in an excess of other metal salts at 37° C. over 7 days. The only metal that removed Zr out of the chelator was $Fe^{3+}$. Both hydroxamates and hydroxypyridinones have an affinity for iron and DFO is a natural siderophore. Still, in the case of $Fe^{3+}$, the $^{89}$Zr-HOPO complex remained intact compared to the $^{89}$Zr-DFO complex by a factor of approximately 2.

Figure 8:
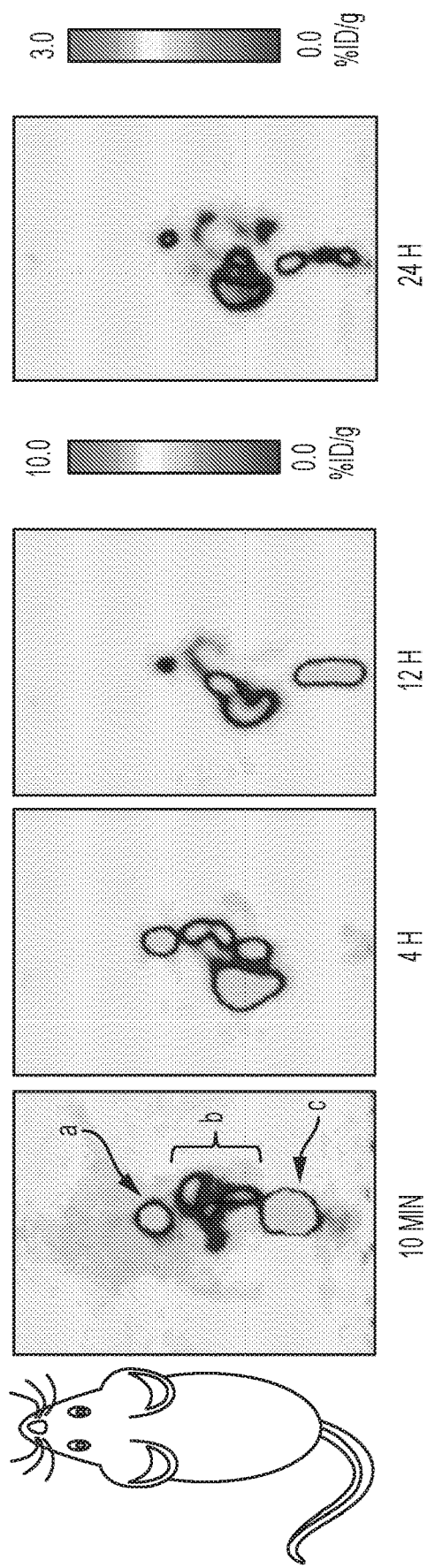
FIG. 8 shows $^{89}$Zr-HOPO PET imaging and clearance in healthy mice at 10 minutes, 4 hours, 12 hours, and 24 hours. Initially activity was seen in the bladder, gall bladder, and intestines. However, after 4 hours, activity was only seen in the gall bladder and gut as the complex is cleared from the mouse, demonstrating rapid renal clearance and slower fecal clearance.

FIG. 2 shows DFO and HOPO radiolabeled with $^{89}$Zr and then incubated in a 50-fold excess of EDTA at 37° C. and various pHs in order to test for transchelation, or if excess EDTA can strip the $^{89}$Zr out of the ligands over time. The data reveals that $^{89}$Zr-DFO is susceptible to transchelation. In contrast, $^{89}$Zr-HOPO is shown to be approximately impervious to the EDTA. At lower pHs, EDTA is able to strip the Zr out of DFO in a matter of hours whereas the $^{89}$Zr-HOPO complex remains intact for the full 7 days. This represents a significant improvement in the stability of the Zr-ligand complex at lower pH. Without having to be bound to any theory, this result suggests that the HOPO ligand can be effective in tumor microenvironments, which are known to be more acidic than most tissues. FIG. 8 shows $^{89}$Zr-HOPO PET imaging and clearance in healthy mice at 10 minutes, 4 hours, 12 hours, and 24 hours. Initially activity is seen in the bladder, gall bladder, and intestines. However, after 4 hours, activity is only seen in the gall bladder and gut as the complex is cleared from the mouse, demonstrating rapid renal clearance and slower fecal clearance.

Figure 9:
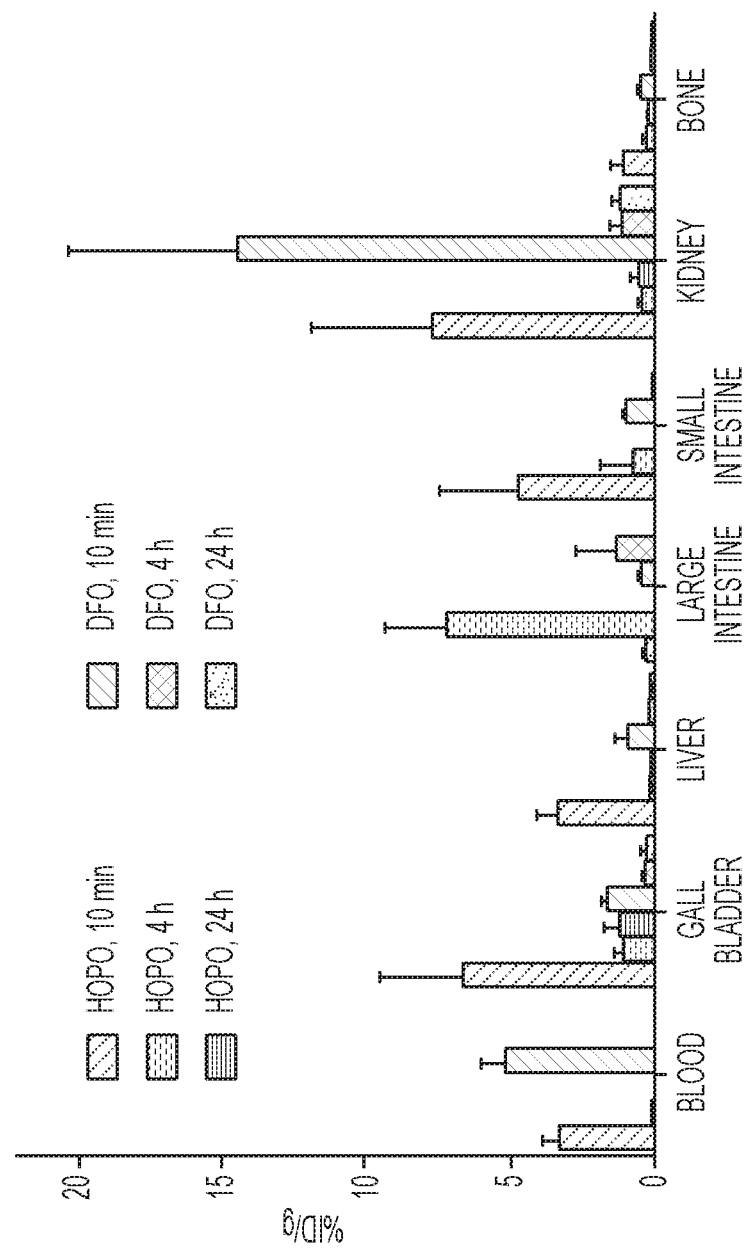
FIG. 9 shows biodistribution of $^{89}$Zr-HOPO and $^{89}$Zr-DFO. $^{89}$Zr-HOPO demonstrates good clearance without any significant accumulation. Low bone activity which decreases over time, suggests that $^{89}$Zr-HOPO is clearing and not mineralizing. $^{89}$Zr-DFO only clears through the kidneys and bladder so it clears faster than $^{89}$Zr-HOPO, but over the short circulation time of the Zr-ligand complexes, neither DFO nor HOPO show any signs of instability or bone accumulation.

FIG. 9 shows biodistribution of $^{89}$Zr-HOPO and $^{89}$Zr-DFO. $^{89}$Zr-HOPO demonstrates good clearance without any significant accumulation (values are given in Table 1).

TABLE 1

| | 24 h | | 72 h | | 120 h | | 168 h |
|---|---|---|---|---|---|---|---|
| | HOPO | DFO | HOPO | DFO | HOPO | DFO | HOPO |
| Blood | 13.6 ± 2.4 | 14.8 ± 1.4 | 12.5 ± 2.9 | 9.4 ± 1.0 | 8.9 ± 1.6 | 10.2 ± 0.8 | 6.9 ± 2.7 |
| Tumor | 29.0 ± 11.4 | 22.4 ± 14.3 | 54.7 ± 19.5 | 51.4 ± 10.4 | 68.8 ± 18.8 | 95.0 ± 16.7 | 70.4 ± 23.5 |
| Heart | 3.7 ± 0.4 | 3.9 ± 0.7 | 2.7 ± 0.5 | 3.7 ± 2.3 | 2.4 ± 0.5 | 3.0 ± 0.3 | 1.7 ± 0.6 |
| Lungs | 5.9 ± 1.0 | 7.2 ± 1.6 | 6.0 ± 1.7 | 4.3 ± 2.2 | 4.6 ± 1.2 | 5.9 ± 0.8 | 3.7 ± 1.2 |
| Liver | 5.2 ± 0.4 | 5.6 ± 1.1 | 5.8 ± 0.8 | 6.6 ± 1.9 | 9.2 ± 3.2 | 5.7 ± 0.5 | 4.5 ± 1.0 |
| Spleen | 3.6 ± 1.2 | 2.8 ± 0.7 | 2.9 ± 1.1 | 2.3 ± 0.2 | 1.9 ± 0.2 | 3.3 ± 0.3 | 1.8 ± 0.7 |
| Pancreas | 1.6 ± 0.1 | 1.5 ± 0.5 | 1.4 ± 0.4 | 1.2 ± 0.1 | 1.1 ± 0.2 | 1.4 ± 0.2 | 0.8 ± 0.4 |
| Stomach | 0.8 ± 0.4 | 1.2 ± 0.2 | 0.6 ± 0.2 | 1.3 ± 0.6 | 0.5 ± 0.4 | 1.3 ± 0.4 | 0.6 ± 0.4 |
| Sm. Int. | 1.6 ± .04 | 2.1 ± 0.6 | 1.4 ± 0.2 | 1.4 ± 0.2 | 0.8 ± 0.2 | 1.2 ± 0.4 | .07 ± 0.1 |
| Lg. Int. | 1.4 ± 0.6 | 1.2 ± 0.3 | 1.2 ± 0.1 | 1.1 ± 0.3 | 0.9 ± 0.2 | 1.0 ± 0.1 | 0.8 ± 0.2 |
| Kidneys | 4.4 ± 0.8 | 4.6 ± 0.4 | 4.4 ± 0.8 | 4.0 ± 0.3 | 3.4 ± 0.5 | 4.3 ± 0.2 | 2.7 ± 0.7 |
| Muscle | 1.3 ± 0.3 | 1.1 ± 0.2 | 1.1 ± 0.3 | 1.0 ± 0.1 | 0.8 ± 0.3 | 0.8 ± 0.1 | 0.8 ± 0.1 |
| Bone | 2.6 ± 0.6 | 2.4 ± 0.7 | 2.7 ± 0.1 | 5.5 ± 1.7 | 2.0 ± 0.2 | 6.1 ± 0.7 | 2.5 ± 0.5 |
| Tail | 2.9 ± 0.6 | 2.4 ± 0.9 | 2.2 ± 0.4 | 1.7 ± 0.3 | 1.6 ± 0.1 | 1.9 ± 0.2 | 1.6 ± 0.5 |

| | 168 h | 216 h | | 336 h | |
|---|---|---|---|---|---|
| | DFO | HOPO | DFO | HOPO | DFO |
| Blood | 7.1 ± 1.4 | 3.5 ± 2.2 | 4.8 ± 0.9 | 4.3 ± 1.8 | 4.4 ± 0.9 |
| Tumor | 99.1 ± 8.7 | 39.6 ± 21.2 | 74.9 ± 29.9 | 61.9 ± 26.4 | 138.2 ± 35.3 |
| Heart | 2.0 ± 0.3 | 1.0 ± 0.4 | 1.4 ± 0.3 | 1.0 ± 0.4 | 1.4 ± 0.2 |
| Lungs | 4.8 ± 1.0 | 1.7 ± 0.9 | 3.0 ± 0.4 | 2.1 ± 0.8 | 3.4 ± 1.0 |
| Liver | 6.6 ± 2.1 | 4.7 ± 0.9 | 4.9 ± 2.2 | 3.4 ± 1.9 | 7.2 ± 1.8 |
| Spleen | 2.6 ± 0.7 | 1.3 ± 0.3 | 2.9 ± 0.7 | 1.4 ± 0.4 | 3.0 ± 0.2 |
| Pancreas | 1.0 ± 0.2 | 0.5 ± 0.3 | 0.9 ± 0.2 | 0.5 ± 0.2 | 0.8 ± 0.1 |
| Stomach | 0.6 ± 0.2 | 0.3 ± 0.2 | 0.5 ± 0.2 | 0.3 ± 0.1 | 0.7 ± 0.2 |
| Sm. Int. | 0.9 ± 0.2 | 0.4 ± 0.2 | 0.8 ± 0.2 | 0.4 ± 0.2 | 0.9 ± 0.1 |
| Lg. Int. | 0.7 ± 0.1 | 0.5 ± 0.2 | 0.8 ± 0.1 | 0.5 ± 0.2 | 0.7 ± 0.1 |
| Kidneys | 4.0 ± 0.3 | 1.9 ± 0.6 | 2.6 ± 0.3 | 1.8 ± 0.5 | 3.1 ± 0.8 |
| Muscle | 0.8 ± 0.1 | 0.4 ± 0.1 | 0.8 ± 0.5 | 0.4 ± 0.1 | 0.6 ± .01 |
| Bone | 8.1 ± 1.4 | 2.5 ± 0.3 | 10.7 ± 1.3 | 2.4 ± 0.3 | 17.0 ± 4.1 |
| Tail | 1.8 ± 0.4 | 1.1 ± 0.4 | 1.7 ± 0.4 | 0.9 ± 0.3 | 1.5 ± 0.2 |

Figure 10:
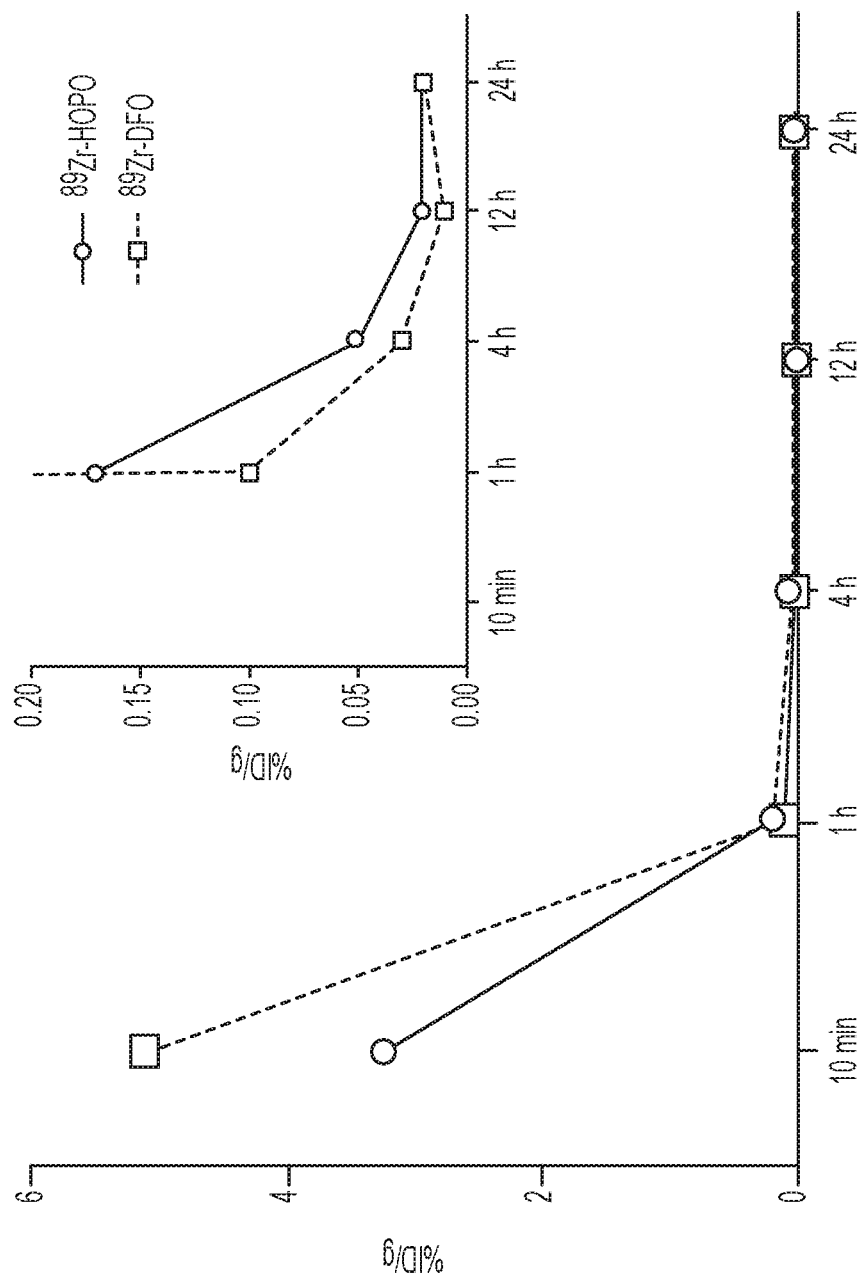
FIG. 10 shows blood clearance of $^{89}$Zr-HOPO and $^{89}$Zr-DFO in healthy athymic nude mice (n=4) over time. Inset shows a zoomed graph for further detail.

Without having to be bound to any theory, bone activity decreasing over time suggests that $^{89}$Zr-HOPO is clearing and not mineralizing. $^{89}$Zr-DFO clears exclusively through the kidneys. Significant uptake of $^{89}$Zr-HOPO occurs in the gall bladder and intestines as well as the kidney. Without wishing to be bound to any theory, this suggests that $^{89}$Zr-HOPO is cleared through both renal and hepatobiliary excretion. As $^{89}$Zr-DFO is cleared exclusively through the kidneys and not through the hepatobiliary system, it is excreted from the body faster than $^{89}$Zr-HOPO, as evidenced by the blood clearance curve (FIG. 10). While not wishing to be bound to theory, upon conjugation to an antibody, the pharmacokinetics of a $^{89}$Zr-HOPO complex comprising $^{89}$Zr-HOPO and an antibody can be superseded by those of the biomacromolecule, meaning that a difference in clearance pathways between $^{89}$Zr-HOPO and $^{89}$Zr-DFO should not be a concern. However, over the short circulation time of the Zr-ligand complexes, neither DFO nor HOPO show any signs of instability or bone accumulation.

Figure 11:
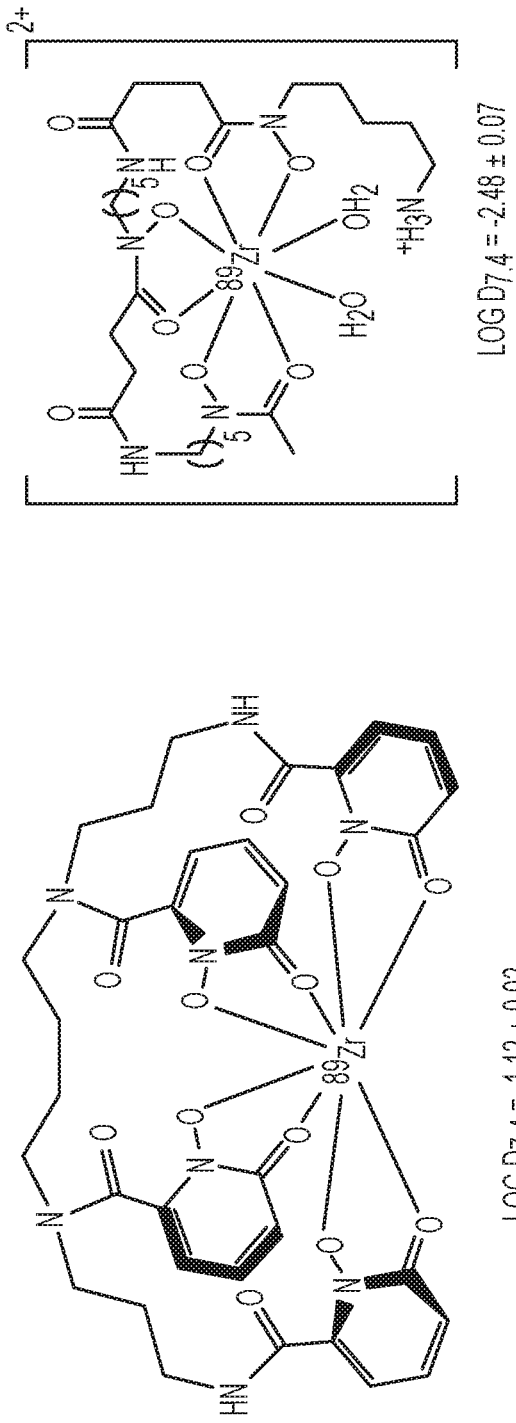
FIG. 11 shows partition coefficients of $^{89}$Zr-HOPO and $^{89}$Zr-DFO at pH 7.4.

FIG. 11 shows partition coefficients of $^{89}$Zr-HOPO and $^{89}$Zr-DFO at pH 7.4. Without having to be bound to any theory, the difference in clearance pathways between the two complexes is the difference in their partitions coefficients. The $^{89}$Zr-HOPO complex is more lipophilic than $^{89}$Zr-DFO which can cause the $^{89}$Zr-HOPO complex to be digested through the gut (e.g., instead of cleared through the kidneys like $^{89}$Zr-DFO).

Figure 12:
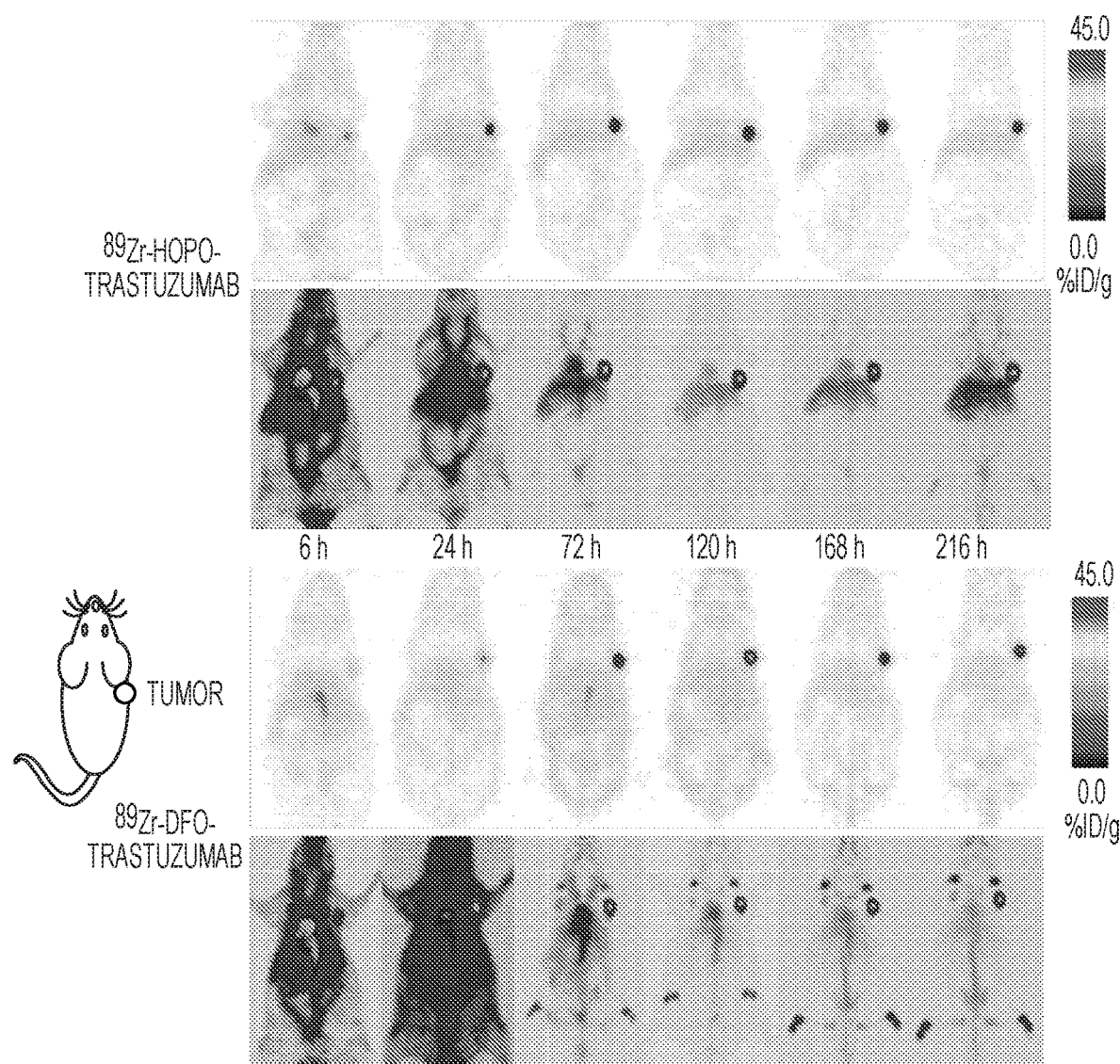
FIG. 12 shows PET images of chelator for $^{89}$Zr-HOPO-trastuzumab (top) and chelator for $^{89}$Zr-DFO-trastuzumab (bottom) in female, athymic nude mice with BT474 xenografts on their right shoulders (9.25-9.99 MBq [250-270 μCi] in 200 μL 0.9% sterile saline). Representative images are shown for each compound following a single mouse over 9 d with coronal slice images above corresponding maximum intensity projection images. Both compounds show good tumor to background contrast, but $^{89}$Zr-DFO-trastuzumab shows evidence of bone uptake suggesting in vivo release of chelator for $^{89}$Zr$^{4+}$.
Figure 13:
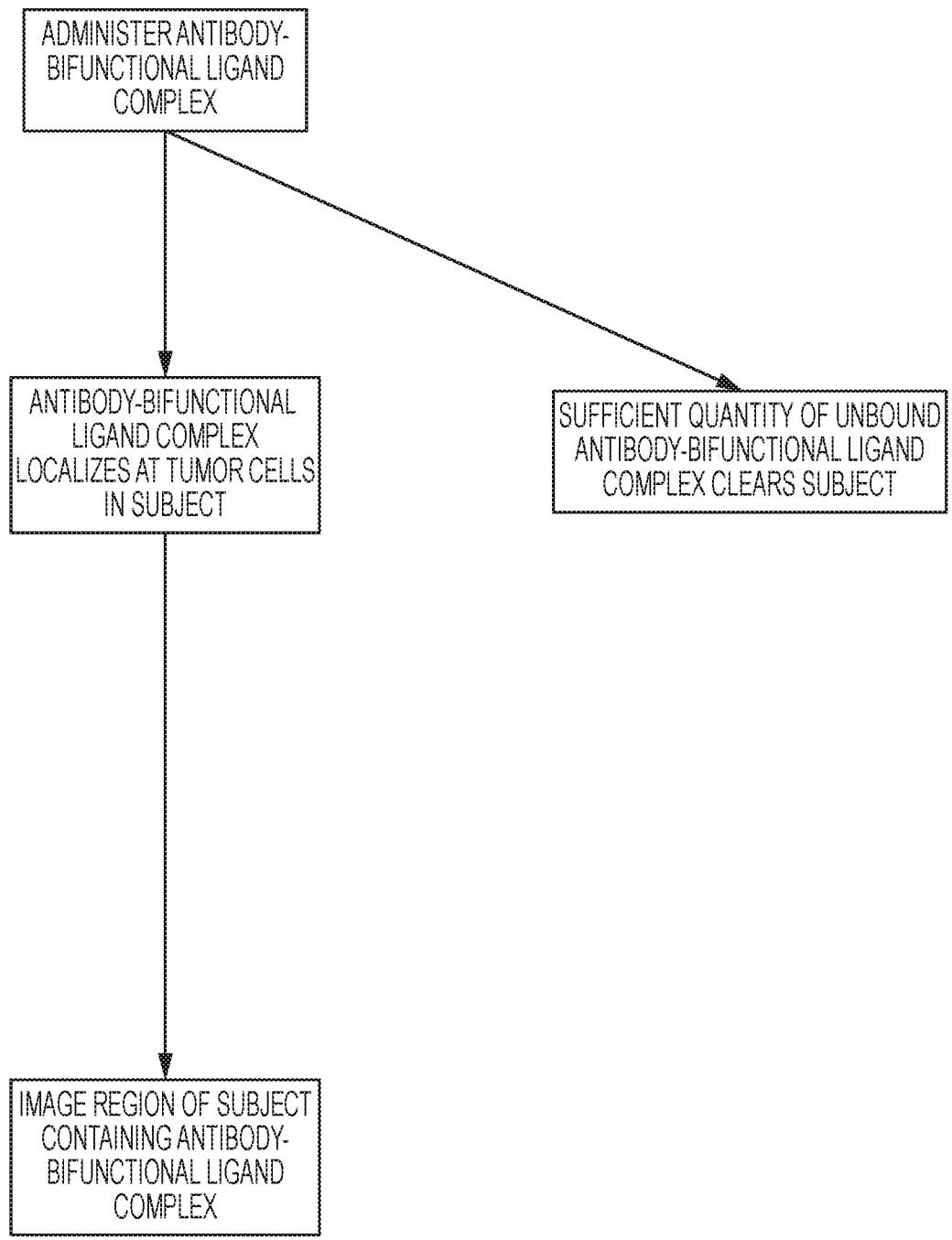
FIG. 13 shows an illustrative embodiment of a method to image certain regions of a subject that have been labeled using an antibody-bifunctional ligand complex where the antibody is chosen to selectively interact with the certain regions.

PET imaging was carried out in order to directly compare the in vivo behavior and pharmacokinetics of DFO- and HOPO-based $^{89}$Zr-trastuzumab radioimmunoconjugates. Female, athymic nude mice with subcutaneous BT474 xenografts in their right shoulders were injected with either $^{89}$Zr-DFO-trastuzumab or $^{89}$Zr-HOPO-trastuzumab (n=4 for each compound) and imaged over 9 d. The resulting images showed good tumor uptake for both compounds, but with a marked decrease in the appearance of bone uptake for the $^{89}$Zr-HOPO-trastuzumab images (FIG. 12). An illustrative embodiment of the method used for PET imaging is given in FIG. 13. One aspect of this method is that sufficient time must elapse after administration of the bifunctional ligand-antibody complex to allow for unbound bifunctional ligand-antibody complex to clear the subject (e.g., by renal or fecal clearance). At that point, the bound bifunctional ligand-antibody complex can be appropriately imaged with high contrast due to the lack of noise that can be generated by unbound bifunctional ligand-antibody complexes. The presence of significant deposition or binding of radiolabels in the subject that do not correspond to the region of interest (e.g., bone) can also serve to reduce contrast and thus produce lower quality images. The generated image of the tumor can be used for gaining quantitative information about the tumor and/or one or more tumor cells present, such as its/their dimensions (e.g., size, volume), shape, or rate of growth or shrinkage. Additional information about one or more moiety expressions (e.g., protein expressions) of the tumor can also be gained based on whether association of one or more antibodies utilized in the composition occurs with one or more tumor cells in the subject. Without having to be bound by theory, the reduced bone uptake seen with $^{89}$Zr-HOPO-trastuzumab (Tz) suggests superior stability of the $^{89}$Zr-HOPO complex. The difference in in vivo performance in contrast to the in vitro stability study highlights the inadequacy of the serum stability assay alone. These data demonstrate the successful use of $^{89}$Zr-HOPO-trastuzumab to image BT474 breast cancer with low background, good tumor to organ contrast, and, importantly, very low bone uptake compared to conventional (e.g., DFO-based) ligands.

Trastuzumab (Tz) antibody was conjugated to p-SCN-Bn-HOPO and p-SCN-Bn-DFO, and the conjugation efficiencies were compared. Although the complex comprising p-SCN-Bn-HOPO and Tz ("HOPO-Tz complex") achieved satisfactory radiolabeling yields, its conjugation efficiency was lower compared to the conjugation efficiency of the complex comprising p-SCN-Bn-DFO and Tz ("DFO-Tz complex"). Although HOPO-Tz complexes had on average more chelates per antibody than the DFO-Tz complexes, the HOPO-Tz complexes only showed specific activities up to about 2.5 mCi/mg (compared to a specific activity of 4 mCi/mg for the DFO-Tz complexes). This difference in specific activity does not necessarily hinder the application of the HOPO chelator. Moreover, the difference can be overcome through optimization of the linker portion of the bifunctional chelator. The position, length, spacer type, and conjugation functionality of the linker can be systematically altered to create a library of possible bifunctional ligands. These variants can be evaluated both in vitro for favorable radiolabeling properties and in vivo for stability and biological applicability.

Quantitative and Comparative Evaluation the In Vivo Behavior and Pharmacokinetics of Complexes Complexes can be screened with in vivo tumor models to determine their pharmacokinetics and stabilities. $^{89}$Zr-ligand-trastuzumab complexes can be evaluated (e.g., as a well-studied model system) to determine their stability, biodistribution, and overall utility as PET imaging agents compared to $^{89}$Zr-DFO-trastuzumab.

For example, the complexes can be screened in in vivo tumor HER2 positive and negative models to determine their behavior and stability using small animal PET/CT imaging. The tumor uptake and pharmacokinetics of the $^{89}$Zr-ligand-antibody complexes can be determined. The $^{89}$Zr-ligand-trastuzumab complexes can be evaluated to determine their stability, biodistribution, and overall utility as imaging agents.

FIG. 12 shows PET images of female, athymic nude mice (e.g., treated with estrogen pellets to generate HER2/neu positive BT474 breast cancer tumors) injected with either $^{89}$Zr-DFO-Trastuzumab or $^{89}$Zr-HOPO-Trastuzumab at 6 hours, 24 hours, 72 hours, 120 hours, and 216 hours. Trastuzumab targets HER2/neu receptor.

Figure 14:
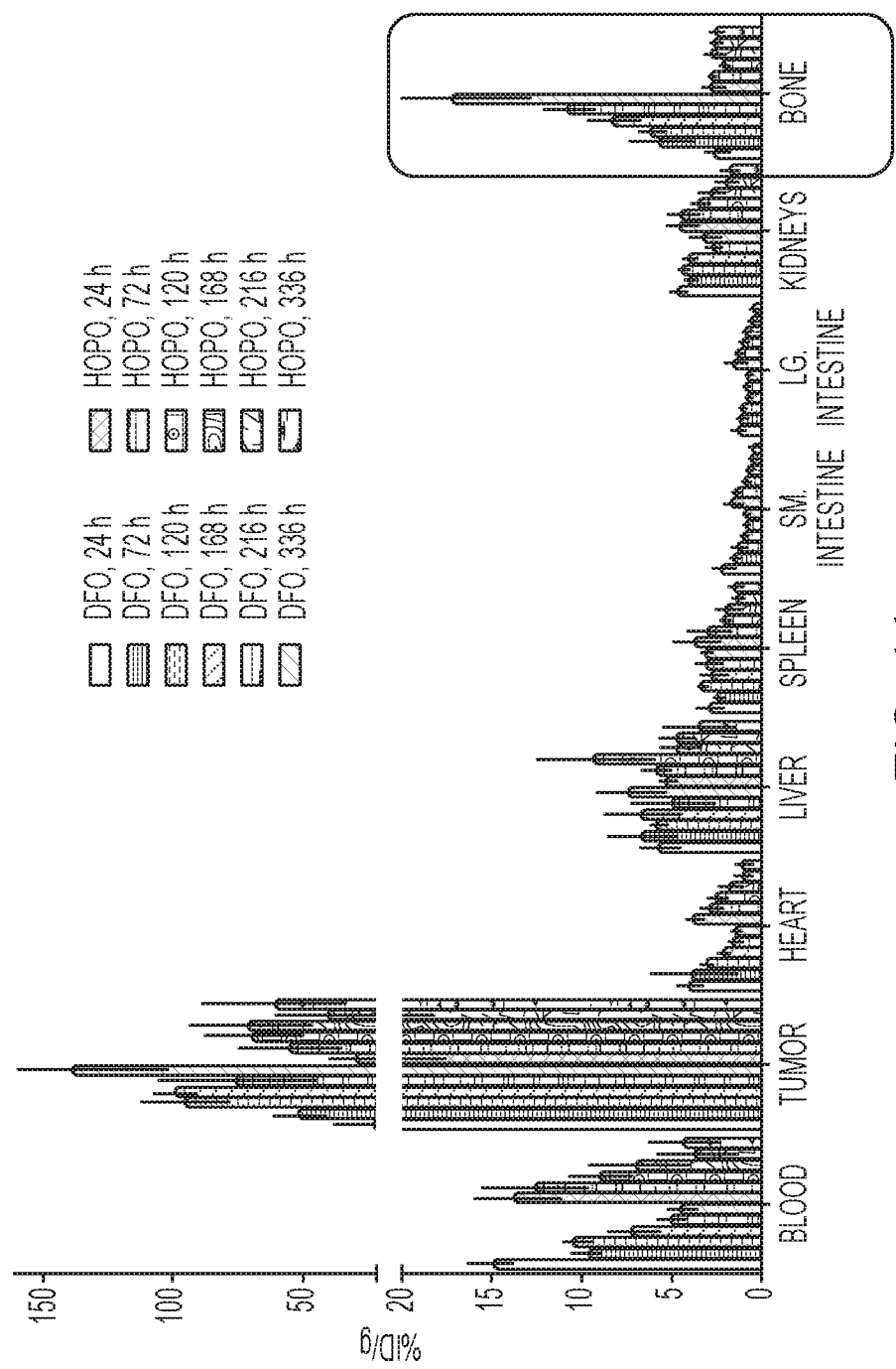
FIG. 14 shows select biodistribution data of chelator $^{89}$Zr-HOPO-trastuzumab (red) and $^{89}$Zr-DFO-trastuzumab (blue) in female, athymic nude mice with BT474 xenografts (0.59-0.74 MBq [16-20 μCi] in 200 μL 0.9% sterile saline). Both compounds successfully target and accumulate in the BT474 tumors with good tumor to background contrast, but $^{89}$Zr-DFO-trastuzumab has ~2.5 times the absolute uptake in the tumor. The distribution pattern is very similar for all non-target organs except for the bone. T. The $^{89}$Zr-DFO-trastuzumab mice show an increasing level of activity in the bone suggesting in vivo release of $^{89}$Zr$^{4+}$ and accumulation in the bone, whereas the chelator $^{89}$Zr-HOPO-trastuzumab mice show only a low level of activity in the bone which is below the level of the blood and does not increase over time.

FIG. 14 shows biodistribution of $^{89}$Zr-DFO-Trastuzumab and $^{89}$Zr-HOPO-Trastuzumab at 6 hours, 24 hours, 72 hours, 120 hours, 216 hours, and 336 hours. The results show similar biodistribution patterns as seen in FIG. 9; however, $^{89}$Zr-HOPO-Trastuzumab shows markedly less bone uptake. Acute biodistribution experiments were performed to further probe the localization and uptake of $^{89}$Zr-DFO-trastuzumab and $^{89}$Zr-HOPO-trastuzumab. These results corroborate the observations from the PET images with the activity associated with all collected tissues, except the tumors and the bone, decreasing over time (FIG. 14). Both compounds showed good uptake in the tumor with the DFO complex achieving higher uptake than the HOPO compound (138.2±35.3 vs. 61.9±26.4% ID/g, Table 2).

TABLE 2

|  | 10 min | | 1 h | | 4 h |
| --- | --- | --- | --- | --- | --- |
|  | Zr-HOPO | Zr-DFO | Zr-HOPO | Zr-DFO | Zr-HOPO |
| Blood | 3.24 ± 0.66 | 5.11 ± 0.90 | 0.17 ± 0.10 | 0.10 ± 0.04 | 0.05 ± 0.04 |
| Heart | 1.57 ± 0.22 | 2.17 ± 0.62 | 0.12 ± 0.06 | 0.06 ± 0.02 | 0.06 ± 0.01 |
| Lung | 1.07 ± 0.17 | 2.16 ± 1.08 | 0.17 ± 0.09 | 0.14 ± 0.04 | 0.08 ± 0.01 |
| Gall Bladder | 6.61 ± 2.87 | 1.57 ± 0.25 | 6.94 ± 3.38 | 0.47 ± 0.14 | 1.00 ± 0.41 |
| Liver | 3.29 ± 0.75 | 0.88 ± 0.49 | 0.22 ± 0.09 | 0.24 ± 0.07 | 0.13 ± 0.01 |
| Spleen | 0.31 ± 0.04 | 0.37 ± 0.22 | 0.09 ± 0.03 | 0.06 ± 0.02 | 0.06 ± 0.01 |
| Stomach | 1.22 ± 0.39 | 0.62 ± 0.28 | 0.30 ± 0.15 | 1.10 ± 0.51 | 0.50 ± 0.74 |
| Large Intestine | 0.26 ± 0.15 | 0.43 ± 0.13 | 0.09 ± 0.06 | 0.02 ± 0.01 | 7.17 ± 2.15 |
| Small Intestine | 5.99 ± 1.18 | 0.94 ± 0.16 | 1.11 ± 0.35 | 0.35 ± 0.17 | 0.12 ± 0.13 |
| Kidney | 9.46 ± 2.71 | 14.44 ± 5.88 | 1.05 ± 0.51 | 1.39 ± 0.55 | 0.40 ± 0.14 |
| Bladder | 2.04 ± 1.06 | 2.50 ± 0.48 | 0.73 ± 0.36 | 2.47 ± 1.30 | 0.58 ± 0.27 |
| Muscle | 0.36 ± 0.06 | 0.73 ± 0.56 | 0.10 ± 0.03 | 0.02 ± 0.01 | 0.09 ± 0.06 |
| Bone | 1.04 ± 0.44 | 0.43 ± 0.10 | 0.29 ± 0.09 | 0.07 ± 0.04 | 0.23 ± 0.12 |
| Tail | 4.25 ± 1.46 | 5.13 ± 2.92 | 0.81 ± 0.34 | 0.26 ± 0.05 | 0.29 ± 0.18 |

|  | 4 h | 12 h | | 24 h | |
| --- | --- | --- | --- | --- | --- |
|  | Zr-DFO | Zr-HOPO | Zr-DFO | Zr-HOPO | Zr-DFO |
| Blood | 0.03 ± 0.01 | 0.02 ± 0.00 | 0.01 ± 0.00 | 0.02 ± 0.00 | 0.02 ± 0.02 |
| Heart | 0.03 ± 0.01 | 0.06 ± 0.01 | 0.02 ± 0.00 | 0.07 ± 0.01 | 0.02 ± 0.01 |
| Lung | 0.04 ± 0.02 | 0.06 ± 0.01 | 0.02 ± 0.01 | 0.06 ± 0.05 | 0.04 ± 0.01 |
| Gall Bladder | 0.26 ± 0.15 | 2.45 ± 1.02 | 0.16 ± 0.14 | 1.15 ± 0.59 | 0.23 ± 0.21 |
| Liver | 0.12 ± 0.03 | 0.09 ± 0.02 | 0.06 ± 0.02 | 0.06 ± 0.03 | 0.11 ± 0.02 |
| Spleen | 0.03 ± 0.01 | 0.05 ± 0.01 | 0.02 ± 0.01 | 0.06 ± 0.01 | 0.02 ± 0.01 |
| Stomach | 0.06 ± 0.02 | 0.01 ± 0.00 | 0.01 ± 0.00 | 0.02 ± 0.00 | 0.01 ± 0.01 |
| Large Intestine | 0.62 ± 0.55 | 0.10 ± 0.03 | 0.07 ± 0.05 | 0.03 ± 0.02 | 0.02 ± 0.01 |
| Small Intestine | 0.04 ± 0.02 | 0.02 ± 0.01 | 0.01 ± 0.01 | 0.02 ± 0.00 | 0.02 ± 0.01 |
| Kidney | 1.10 ± 0.44 | 0.53 ± 0.23 | 0.36 ± 0.13 | 0.51 ± 0.29 | 1.12 ± 0.33 |
| Bladder | 1.22 ± 0.77 | 0.54 ± 0.26 | 0.69 ± 0.31 | 0.28 ± 0.14 | 0.56 ± 0.41 |
| Muscle | 0.01 ± 0.01 | 0.06 ± 0.01 | 0.01 ± 0.00 | 0.06 ± 0.01 | 0.01 ± 0.00 |
| Bone | 0.04 ± 0.02 | 0.25 ± 0.07 | 0.03 ± 0.01 | 0.17 ± 0.03 | 0.06 ± 0.01 |
| Tail | 0.14 ± 0.08 | 0.11 ± 0.04 | 0.13 ± 0.05 | 0.05 ± 0.01 | 0.08 ± 0.02 |

Biodistribution data confirmed the significantly lower bone activity of the HOPO conjugate, measuring 17.0±4.1% ID/g in the bone for the $^{89}$Zr-DFO-trastuzumab while the $^{89}$Zr-HOPO-trastuzumab only had 2.4±0.3% ID/g (e.g., reduction by a factor of approximately 7).

Figure 15:
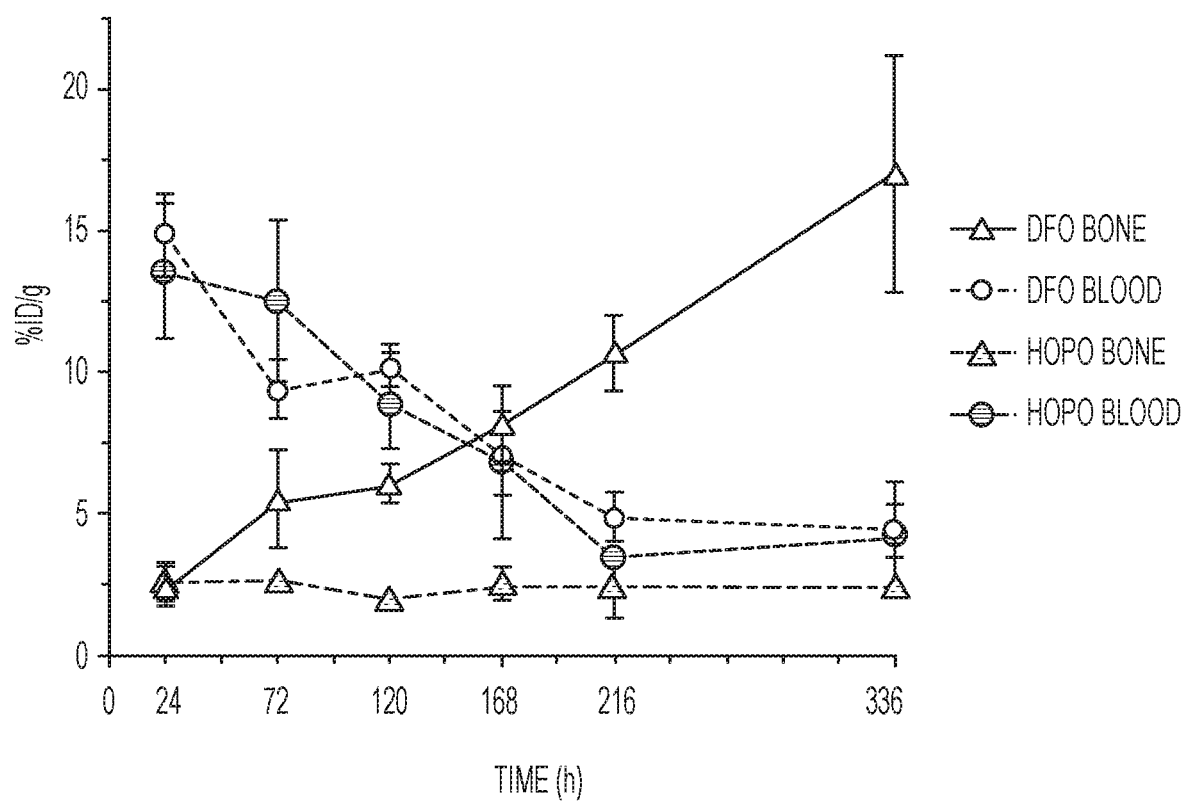
FIG. 15 shows bone activity increases over time as $^{89}$Zr$^{4+}$ is released from DFO and that bone activity for HOPO complex never goes over the background blood level.

The amount of activity seen in the bone with $^{89}$Zr-HOPO-trastuzumab is consistently less than the residual bone activity which means it is possible that there is no specific bone accumulation since the % ID/g values do not increase over time (FIG. 15). This is particularly striking when compared with the constantly increasing bone uptake seen with $^{89}$Zr-DFO-trastuzumab which is indicative of accumulation of $^{89}$Zr$^{4+}$ in the skeleton. While $^{89}$Zr-DFO-trastuzumab has a higher tumor-to-blood ratio than $^{89}$Zr-HOPO-trastuzumab (31.4 vs. 14.4, respectively), the $^{89}$Zr-HOPO-trastuzumab complex has a drastically improved tumor-to-bone ratio of 25.8 compared to 8.1 for $^{89}$Zr-DFO-trastuzumab. Both compounds show a high contrast between the tumor and the general background as represented by the blood activity, but $^{89}$Zr-HOPO-trastuzumab provides increased contrast between the tumor and the bone specifically. Without wishing to be bound to any theory, this benefit of the improved stability of the p-SCN-Bn-HOPO ligand can improve the distinction of bone metastasis metathesis which would reduce radiation dose to healthy bone and bone marrow.

The 3,4,3-(LI-1,2-HOPO) ligand exhibits excellent stability for $^{89}$Zr complexes. For example, p-SCN-Bn-HOPO achieved specific activities of ~2 mCi/mg, was ~90% stable through a 7 d incubation in human serum, and $^{89}$Zr-HOPO-trastuzumab exhibited reduced bone uptake (e.g., more than 7 times compared to $^{89}$Zr-DFO-trastuzumab). While the absolute uptake in BT474 breast cancer tumors was just over 2 times higher for $^{89}$Zr-DFO-trastuzumab, the tumor-to-bone ratio was more than 3 times higher for $^{89}$Zr-HOPO-trastuzumab. This improved contrast between tumor and bone can improve the detection of bone metastasis and improve the general clarity of the images. Without wishing to be bound to any theory, the lower bone uptake furthermore demonstrates that p-SCN-Bn-HOPO ligand forms a more stable complex with $^{89}$Zr$^{4+}$ than p-SCN-Bn-DFO, suggesting a reduced release of free $^{89}$Zr$^{4+}$ in vivo. For example, FIG. 15 shows bone activity increases over time as $^{89}$Zr$^{4+}$ is released from DFO and that bone activity for HOPO complex never goes over the background blood level. As described herein, the bifunctional chelator p-SCN-Bn-HOPO was shown to be an effective chelator of $^{89}$Zr$^{4+}$ for immunoPET applications.

Another possible avenue for investigation is the application of p-SCN-Bn-HOPO toward the chelation of other metals, whether radioactive or otherwise, as therapeutic agents. As the 3,4,3-(LI-1,2-HOPO) ligand was originally made for the purpose of chelating actinides, it follows that the bifunctional ligand p-SCN-Bn-HOPO might also be useful with radiolabels that have medical applications, including but not limited to the actinides and lanthanides. In certain embodiments, a bifunctional ligand where one functionality allows for complexing to a radiolabel and the other allows for complexing with a targeting agent (e.g., an antibody) allows for targeted radioimmunotherapy (RIT) to be administered to a subject (e.g., by injection). In certain embodiments, actinium-225, thorium-227 or lutetium-177 are used as radiolabels for complexing with p-SCN-Bn-HOPO for RIT. Actinium-225 and thorium-227 both emit alpha particles and lutetium-177 emits beta particles that are all suitable for RIT. The thermodynamic stability constant of Th-HOPO has been determined and is comparable to that of Zr-HOPO suggesting that $^{227}$Th can be a good candidate for evaluation with a p-SCN-Bn-HOPO-antibody system. Furthermore, $^{225}$Ac is at the forefront of radioimmunotherapy due to its decay chain containing many other radioactive daughter nuclides which increase the therapeutic payload of the RIT agent. Scandium-44 and gallium-68 are commonly utilized radiolabels for PET. In certain embodiments, scandium-44 or gallium-68 are used as radiolabels in complexes with p-SCN-Bn-HOPO for PET imaging.

Lutetium-177 ($^{177}$Lu) is a radionuclide that emits a beta particle (0.5 MeV $\beta_{max}$, $t_{1/2}$: 6.7 day) and two low energy γ rays (208 keV, 10%; 113 kev, 6%). Lu-177 is used for radiotherapy. In certain embodiments, HOPO and p-SCN-Bn-HOPO can complex with Lutetium-177. The ligand, DOTA (1,4,7,10-tetraazacyclododecane-N,N',N",N"'-tetraacetic acid), is normally employed for complexing Lu-177 for peptides and antibodies for radiotherapy. In certain embodiments, HOPO, when conjugated to an antibody, can be used to stably complex $^{177}$Lu in vivo in an effort to produce a single antibody conjugate that can be radiolabeled with $^{89}$Zr for in vivo PET imaging and/or $^{177}$Lu for targeted radiotherapy. Thus, in certain embodiments, the stability of the $^{177}$Lu complex in biological media, chelator competition, and metal ion competition studies were conducted. Secondly, in vivo studies to determine the in vivo biodistribution of the $^{177}$Lu-HOPO complex was carried out. Finally, $^{177}$Lu-HOPO-trastuzumab was prepared to determine the in vivo stability in both SKOV3 tumor-bearing nude female mice and healthy female mice in order to determine the stability in a longer circulating animal model.

Comparison of HOPO to DOTA

Figure 16:
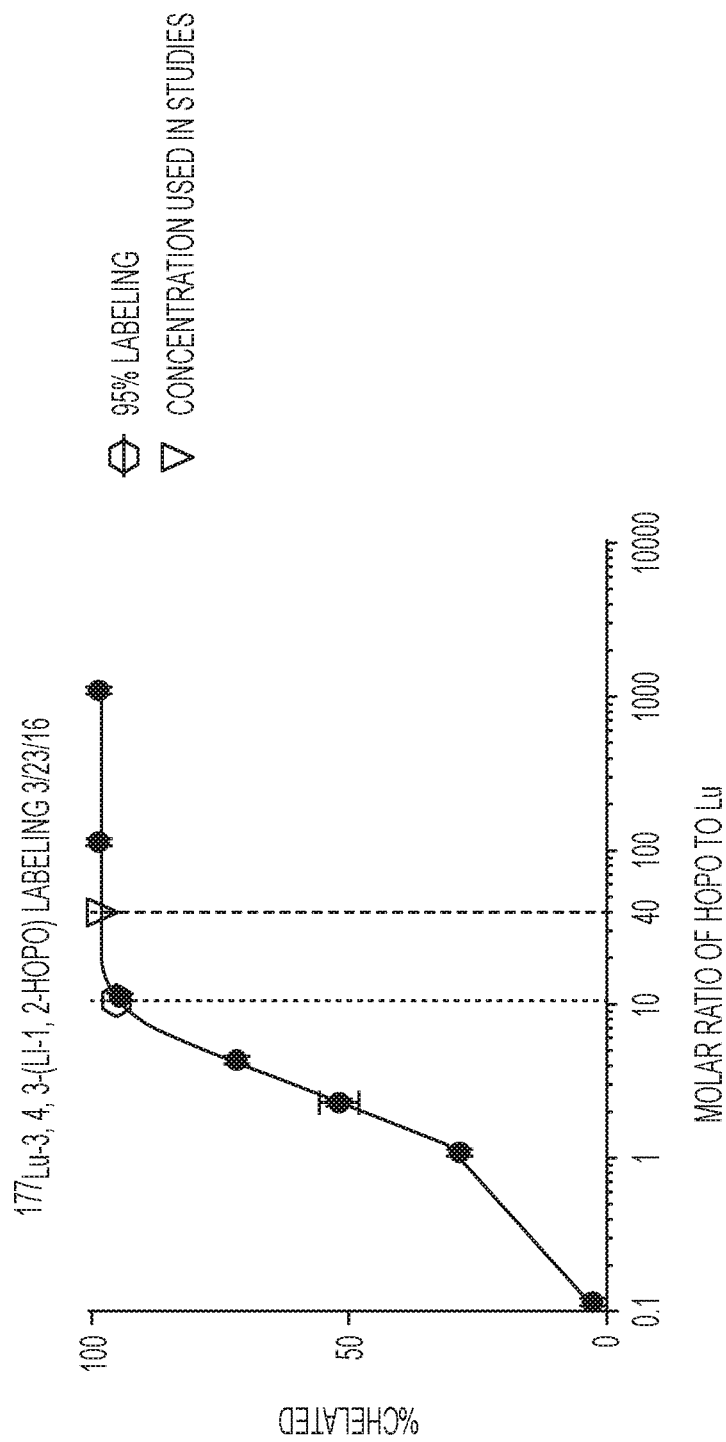
FIG. 16 shows $^{177}$Lu-HOPO labeling at various molar ratios to determine the optimal labeling ratio. The ratio at which 95% labeling is achieved and the labeling ratio used in subsequent studies are displayed by the dotted and dashed lines, respectively. All data points have error bars, but some may be too small to extend past the symbol.
Figure 17A:
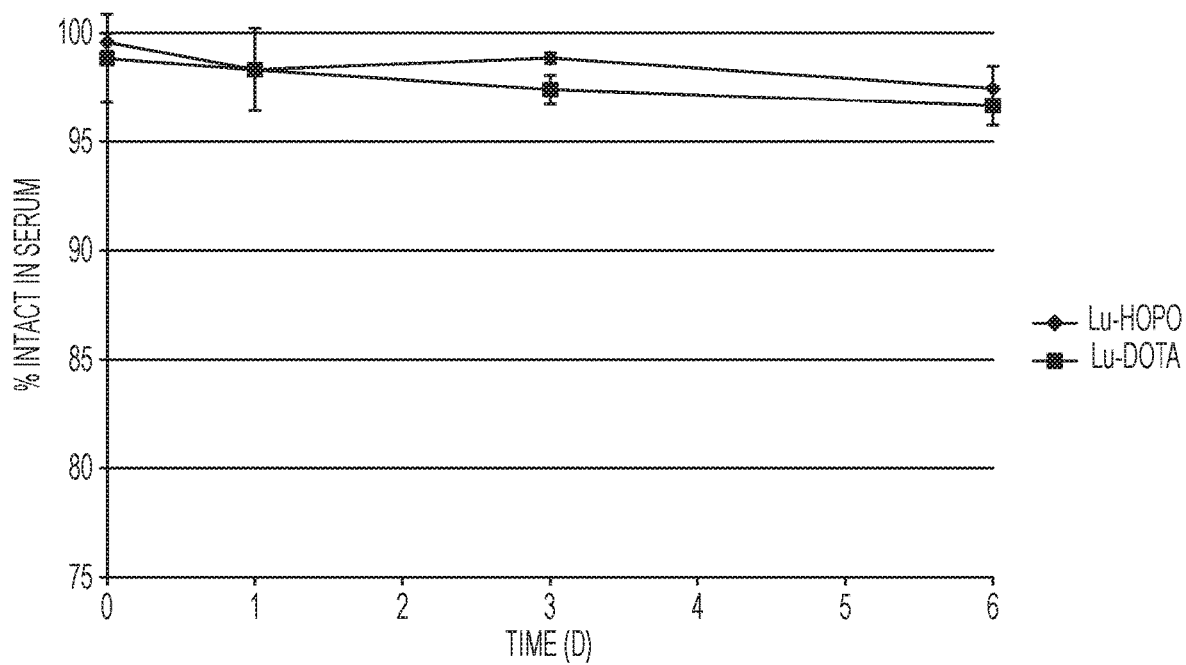
FIG. 17A and FIG. 17B show $^{177}$Lu-HOPO and $^{177}$Lu-DOTA stability in biologically relevant media. Stability is measured in serum (FIG. 17A) and DME HG media (FIG. 17B). Error bars are present on each data point, but may be too small to extend past the symbol.
Figure 17B:
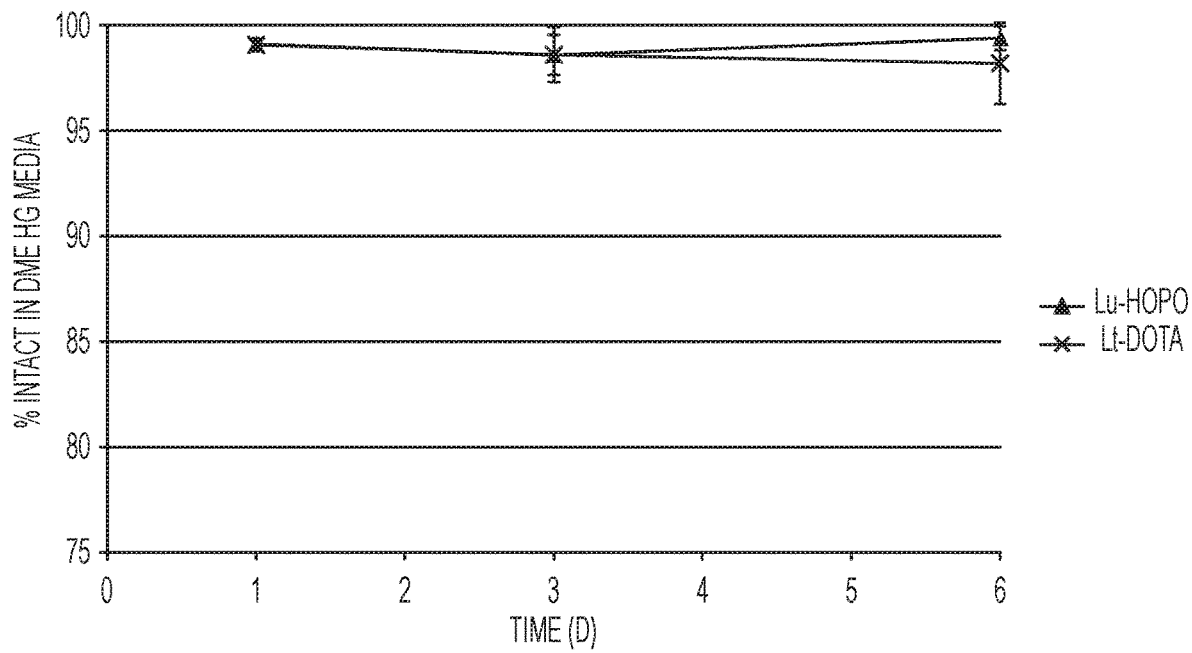
Figure 18:
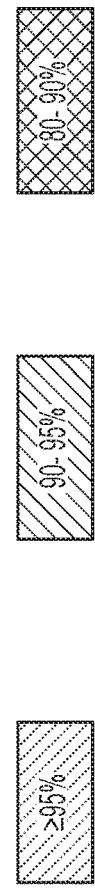
FIG. 18 shows DOTA and HOPO radiolabeled with $^{177}$Lu and then incubated in a 100-fold excess of EDTA at 35° C. and various pHs in order to test for transchelation, or if excess EDTA can strip the $^{177}$Lu out of the ligands over time.
Figure 20:
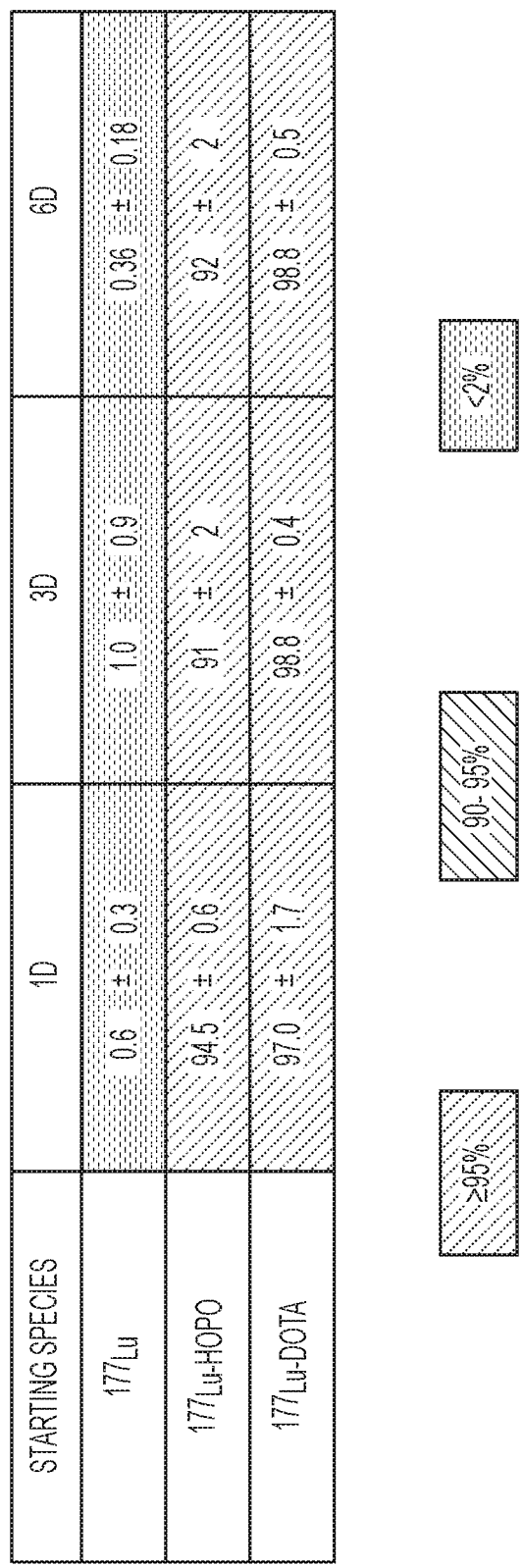
FIG. 20 shows DOTA and HOPO radiolabeled with $^{177}$Lu and then incubated with 1-5 mg of hydroxyapatite in 0.05 M trisacetate buffer at 37° C. at a pH of 7.4 in order to test for hydroxyapatite competition.

Initially, the chelating agents HOPO and DOTA ligands were evaluated with $^{177}$Lu. HOPO was labeled with a constant amount of $^{177}$Lu and varying concentrations of HOPO to determine the optimal labeling ratio of lutetium to HOPO (FIG. 16). These studies showed that, in certain embodiments, for >95% labeling, ten or greater HOPO ligands per lutetium ion was required. For all of the comparison studies between HOPO and DOTA, both ligands were labeled at a ratio of 40 ligand molecules/metal ion.

Once the labeling conditions were decided, the $^{177}$Lu-HOPO and $^{177}$Lu-DOTA complex stabilities were compared in human serum, Dulbecco's Modified Eagle High Glucose (DME HG) cell culture media, EDTA solution buffered at various pH's, 10-fold excess of possible competing metal ions, and in 0.5 M tris buffer in the presence of hydroxyapatite. The results of these studies are shown in FIG. 17A, FIG. 17B, FIG. 18, FIG. 19, and FIG. 20. Greater than 95% of the complexes remained intact in human serum and cell culture media over 6 d. The Lu is transchelated from HOPO more than DOTA at all pHs, but the transchelation is less prevalent at pH 7.0. The peak of stability at pH 7.0 is similar to the stability seen in when EDTA is introduced as a transchelation agent for $^{89}$Zr-DFO, The metal competition study shows that the Lu-DOTA complex is stable to transmetallation with all of the metals investigated in this study, whereas the Lu-HOPO complex is unstable with $Cu^{2+}$ and $Gd^{3+}$. This was in contrast to the results for Zr-based systems that showed that the Zr-HOPO complex was stable in all of the metal solutions except $Fe^{3+}$. Additionally, only a subset of the competing metal cations were chosen for this study, but the DME HG media contained excess metal ions (e.g., 116 fold $Ca^{2+}$, 52 fold $Mg^{2+}$, and 340 fold $K^+$). The results from the metal competition study with Lu-HOPO are inconsistent with the thermodynamic stability constants that were reported by Sturzbecher-Hoehne et al. "In vitro formation of highly stable lanthanide complexes translates into efficacious in vivo europium decorporation. Dalton Trans. 2011; 40(30), 8340-8346.", in which the thermodynamic stability for Lu-HOPO is greater than that of Gd-HOPO. Additionally, there should be excess ligand (ratio of ligand:Lu:metal is 40:1:10), which would decrease the chance of transmetallation. The transmetallation results indicate that the Lu-HOPO complex is less stable than the Lu-DOTA complex, but the concentration of free $Gd^{3+}$ and $Cu^{2+}$ ions should be significantly lower (less than 0.029 mM for total Cu content in the blood) in vivo than evaluated in this study (0.104 mM). Finally, the hydroxyapatite competition showed that the Lu-HOPO complex was >90% intact after 6 d, but was less stable than the Lu-DOTA complex (>98% intact after 6 d).

Figure 21A:
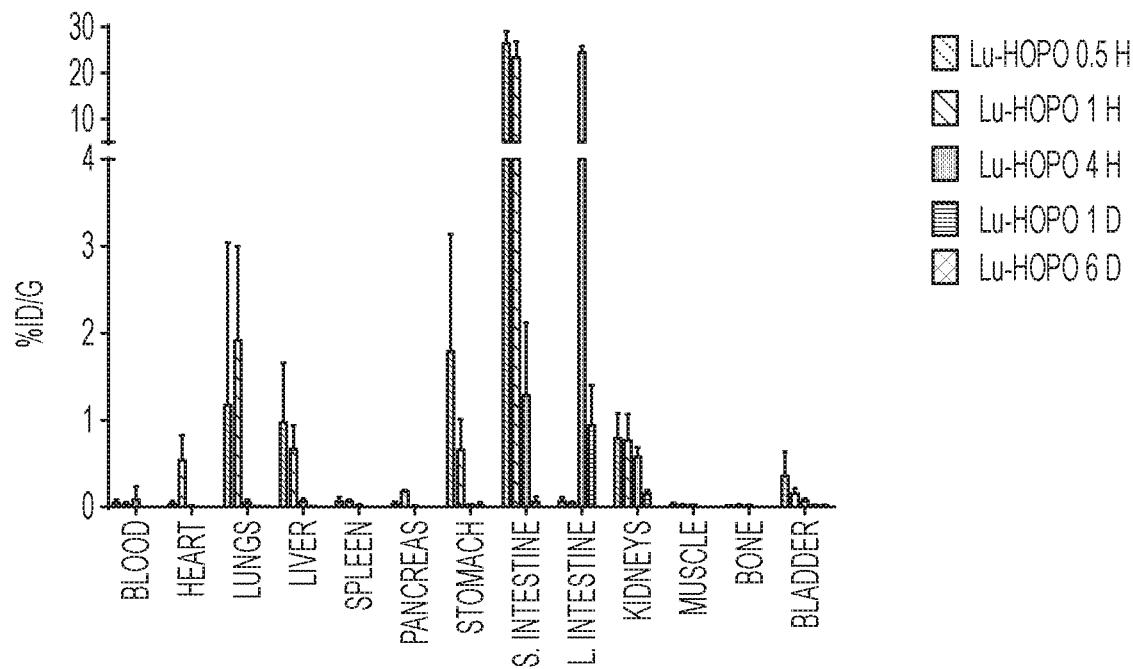
FIG. 21A shows the biodistribution of $^{177}$Lu-HOPO and $^{177}$Lu-DOTA in healthy female nude mice from values in Table 3.
Figure 21A:
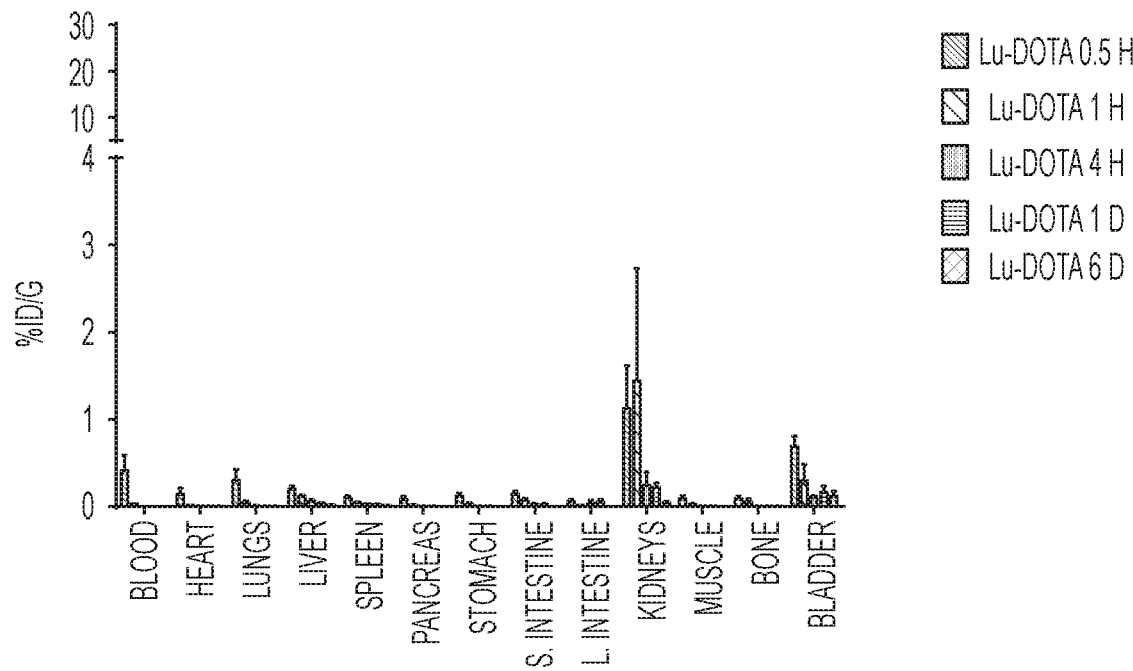
Figure 21B:
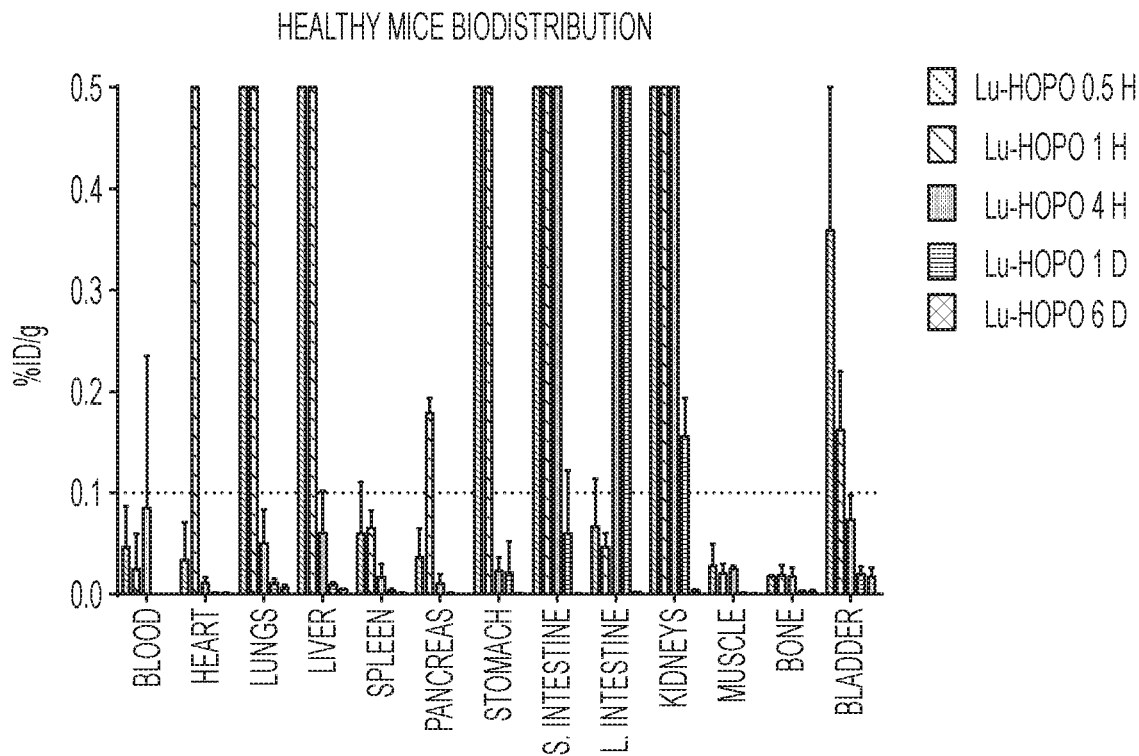
FIG. 21B shows the biodistribution of $^{177}$Lu-HOPO and $^{177}$Lu-DOTA in healthy female nude mice from values in Table 3. The y-axis is modified from FIG. 21A to show precise uptake values for organs that had low uptake.
Figure 21B:
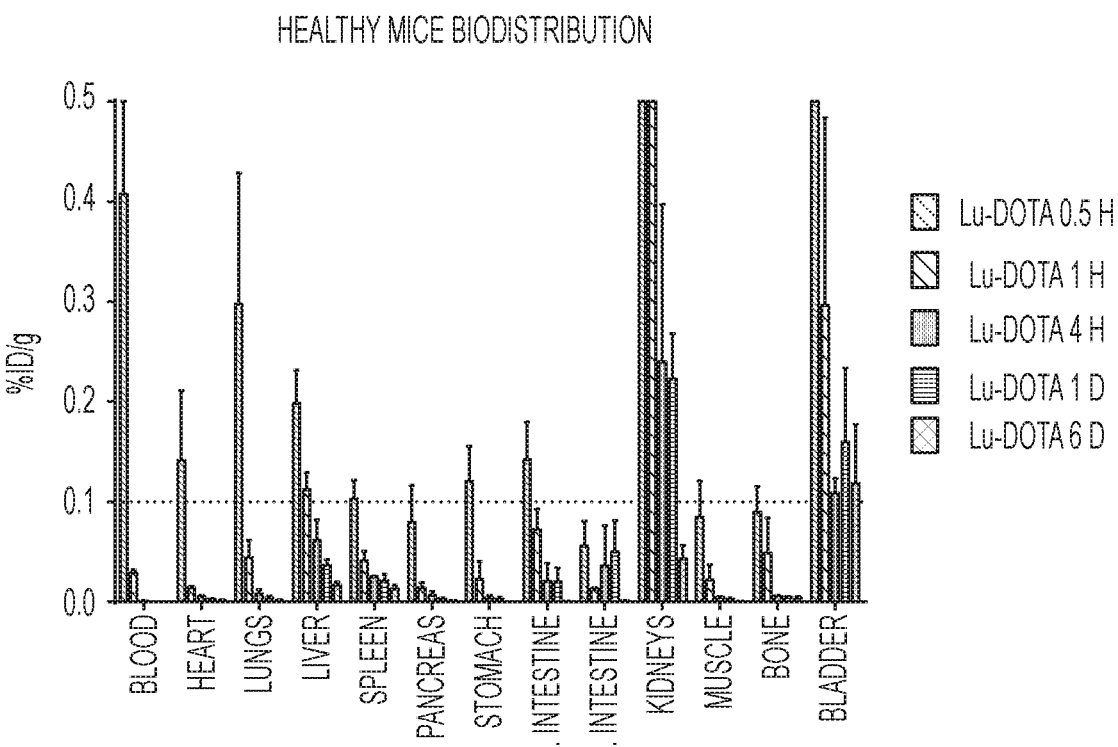
Figure 22:
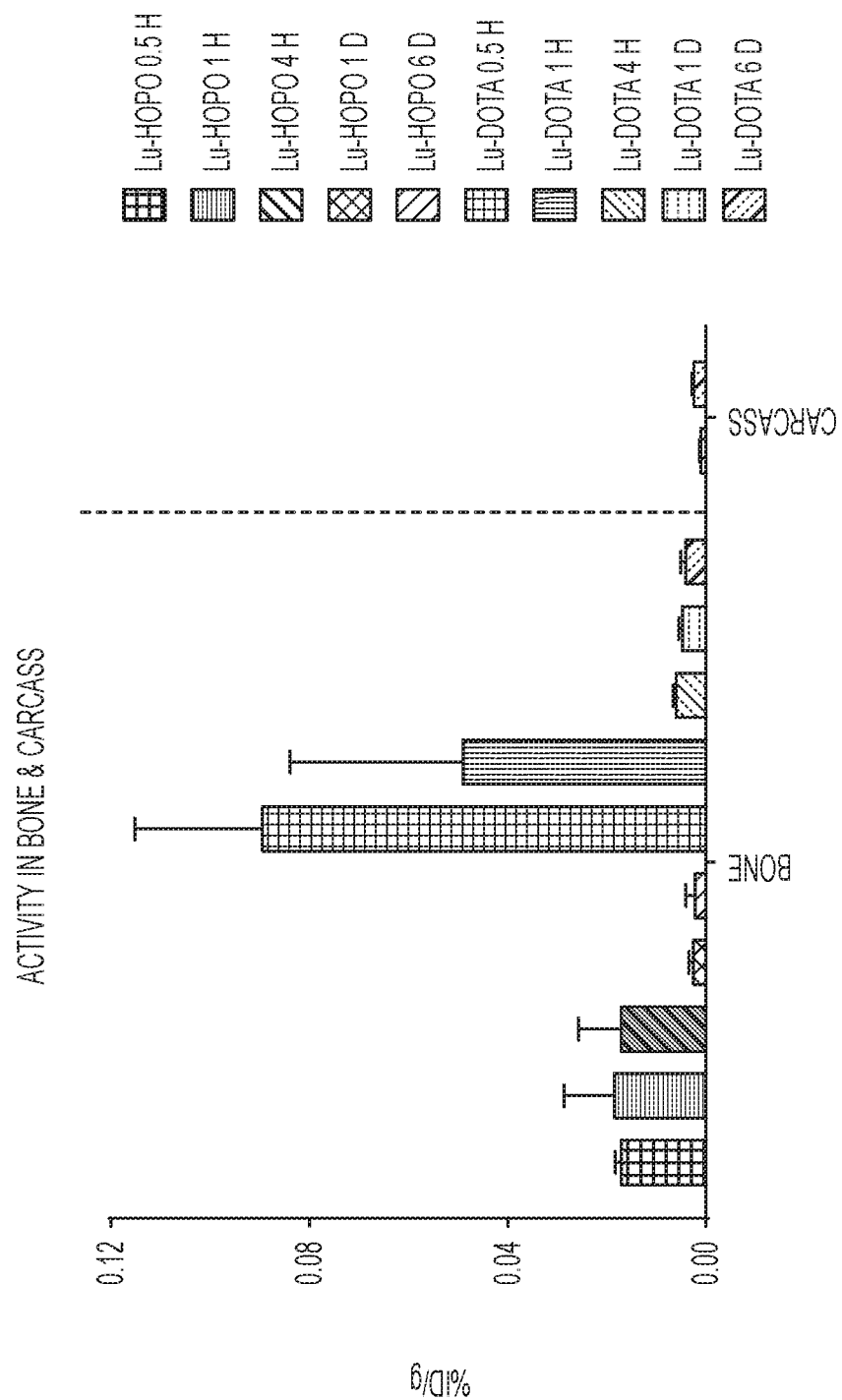
FIG. 22 shows the bone and carcass values for the $^{177}$Lu-HOPO and $^{177}$Lu-DOTA biodistributions in healthy female nude mice showing higher bone uptake for the $^{177}$Lu-DOTA complex compared to $^{177}$Lu-HOPO at all time points except 4 h. The p value between the two carcass values (only collected at 6 d) is 0.000876747.

While in vitro assays suggest lower stability for the Lu-HOPO complex, the in vivo assays are the most important tests. Therefore, healthy female nude mice were injected with each of the complexes in order to determine their relative in vivo stabilities. The results are tabulated in Table 3 and are shown as graphs in FIG. 21A, FIG. 21B and FIG. 22.

TABLE 3

| | 0.5 h | 1 h | 4 h | 1 d | 6 d |
|---|---|---|---|---|---|
| $^{177}$Lu-HOPO | | | | | |
| Blood | 0.0462 ± 0.0408 | 0.025 ± 0.034 | 0.085 ± 0.150 | 0.00012 ± 0.00013 | 0.00003 ± 0.00005 |
| Heart | 0.0334 ± 0.0373 | 0.540 ± 0.284 | 0.011 ± 0.006 | 0.00082 ± 0.00046 | 0.00085 ± 0.00031 |
| Lungs | 1.1718 ± 1.8701 | 1.917 ± 1.084 | 0.050 ± 0.034 | 0.01064 ± 0.00462 | 0.00608 ± 0.00276 |
| Liver | 0.9739 ± 0.6883 | 0.667 ± 0.276 | 0.060 ± 0.041 | 0.00924 ± 0.00233 | 0.00454 ± 0.00060 |
| Spleen | 0.0596 ± 0.0508 | 0.065 ± 0.017 | 0.017 ± 0.013 | 0.00302 ± 0.00217 | 0.00074 ± 0.00049 |
| Pancreas | 0.0362 ± 0.0285 | 0.179 ± 0.015 | 0.010 ± 0.009 | 0.00065 ± 0.00034 | 0.00006 ± 0.00012 |
| Stomach | 1.7917 ± 1.3509 | 0.659 ± 0.356 | 0.023 ± 0.014 | 0.02101 ± 0.03101 | 0.00052 ± 0.00025 |
| S. Intestine | 26.3302 ± 2.6395 | 23.255 ± 3.542 | 1.283 ± 0.843 | 0.05965 ± 0.06206 | 0.00032 ± 0.00009 |
| L. Intestine | 0.0666 ± 0.0473 | 0.046 ± 0.018 | 24.419 ± 1.444 | 0.93994 ± 0.46206 | 0.00214 ± 0.00015 |
| Kidneys | 0.7883 ± 0.2897 | 0.767 ± 0.303 | 0.575 ± 0.113 | 0.15524 ± 0.03810 | 0.00325 ± 0.00096 |
| Muscle | 0.0277 ± 0.0216 | 0.020 ± 0.010 | 0.025 ± 0.003 | 0.00072 ± 0.00036 | 0.00022 ± 0.00039 |
| Bone | 0.0171 ± 0.0013 | 0.019 ± 0.010 | 0.017 ± 0.009 | 0.00257 ± 0.00100 | 0.00221 ± 0.00194 |
| Bladder | 0.3588 ± 0.2743 | 0.162 ± 0.058 | 0.074 ± 0.024 | 0.01997 ± 0.00740 | 0.01705 ± 0.00872 |
| Carcass | | | | | 0.00112 ± 0.00016 |
| $^{177}$Lu-DOTA | | | | | |
| Blood | 0.407 ± 0.179 | 0.0287 ± 0.0038 | 0.0011 ± 0.0003 | 0.00020 ± 0.00011 | 0.00003 ± 0.00006 |
| Heart | 0.142 ± 0.069 | 0.0142 ± 0.0016 | 0.0052 ± 0.0016 | 0.00270 ± 0.00067 | 0.00158 ± 0.00062 |
| Lungs | 0.298 ± 0.131 | 0.0444 ± 0.0175 | 0.0080 ± 0.0044 | 0.00410 ± 0.00192 | 0.00142 ± 0.00102 |
| Liver | 0.199 ± 0.033 | 0.1121 ± 0.0174 | 0.0614 ± 0.0205 | 0.03690 ± 0.00538 | 0.01724 ± 0.00259 |
| Spleen | 0.103 ± 0.019 | 0.0410 ± 0.0100 | 0.0249 ± 0.0009 | 0.02143 ± 0.00625 | 0.01313 ± 0.00408 |
| Pancreas | 0.080 ± 0.037 | 0.0143 ± 0.0050 | 0.0068 ± 0.0038 | 0.00337 ± 0.00062 | 0.00120 ± 0.00048 |
| Stomach | 0.120 ± 0.035 | 0.0230 ± 0.0174 | 0.0038 ± 0.0026 | 0.00294 ± 0.00146 | 0.00045 ± 0.00010 |
| S. Intestine | 0.142 ± 0.038 | 0.0722 ± 0.0209 | 0.0209 ± 0.0180 | 0.02037 ± 0.01362 | 0.00100 ± 0.00011 |
| L. Intestine | 0.056 ± 0.025 | 0.0129 ± 0.0015 | 0.0361 ± 0.0403 | 0.05022 ± 0.03098 | 0.00140 ± 0.00017 |
| Kidneys | 1.121 ± 0.490 | 1.4402 ± 1.2901 | 0.2398 ± 0.1571 | 0.22256 ± 0.04562 | 0.04311 ± 0.01362 |
| Muscle | 0.085 ± 0.037 | 0.0219 ± 0.0154 | 0.0044 ± 0.0007 | 0.00281 ± 0.00151 | 0.00067 ± 0.00046 |
| Bone | 0.090 ± 0.026 | 0.0491 ± 0.0349 | 0.0060 ± 0.0007 | 0.00484 ± 0.00076 | 0.00412 ± 0.00104 |
| Bladder | 0.691 ± 0.116 | 0.2962 ± 0.1869 | 0.1088 ± 0.0148 | 0.15991 ± 0.07394 | 0.11857 ± 0.05899 |
| Carcass | | | | | 0.0025 ± 0.0003 |

From these results, the Lu-HOPO complex is excreted via the hepatobiliary clearance pathway with minimal kidney clearance; whereas, the Lu-DOTA complex is excreted mostly via the renal-urinary clearance pathway. The Log $D_{7.4}$, measured for the two complexes in octanol/PBS, are consistent with these results: the Lu-HOPO complex (Log $D_{7.4}$=−2.43±0.05) presents as more lipophilic than the Lu-DOTA complex (Log $D_{7.4}$=−4.1±0.4). By 1 d post injection (p.i.), the majority of both complexes are cleared. Interestingly, the carcasses of the mice at 6 d p.i. were collected and showed slightly more residual Lu-DOTA (0.044±0.004% ID in carcass; 0.092±0.009% ID in all tissues and carcass) remaining in the mice than Lu-HOPO (0.022±0.002% ID in carcass; 0.036±0.002% ID in all tissues and carcass). The additional activity remaining in the mice injected with Lu-DOTA resulted in greater bone uptake for Lu-DOTA (0.004±0.001% ID/g) compared to Lu-HOPO (0.0022±0.0019% ID/g) at 6 d p.i. Since the bone is the most likely accumulation site for lost $^{177}$Lu, the organ ratios were compared to bone and are tabulated in Table 4.

TABLE 4

| Ratios | 0.5 h | 1 h | 4 h | 1 d | 6 d |
|---|---|---|---|---|---|
| $^{177}$Lu-HOPO | | | | | |
| Muscle/Bone | 1.6 ± 1.3 | 1.1 ± 0.8 | 1.4 ± 0.8 | 0.28 ± 0.18 | 0.10 ± 0.20 |
| Blood/Bone | 3 ± 2 | 1 ± 2 | 5 ± 9 | 0.05 ± 0.05 | 0.02 ± 0.02 |
| Liver/Bone | 60 ± 40 | 40 ± 20 | 4 ± 3 | 3.6 ± 1.7 | 2.1 ± 1.8 |
| S. Intestine/Bone | 1500 ± 200 | 1300 ± 700 | 80 ± 60 | 20 ± 30 | 0.14 ± 0.13 |
| L. Intestine/Bone | 4 ± 3 | 2 ± 2 | 1400 ± 700 | 400 ± 200 | 1.0 ± 0.9 |
| Kidney/Bone | 46 ± 17 | 40 ± 30 | 34 ± 19 | 60 ± 30 | 1.5 ± 1.4 |
| Carcass/Bone | | | | | 0.5 ± 1.4 |
| $^{177}$Lu-DOTA | | | | | |
| Muscle/Bone | 0.9 ± 0.5 | 0.4 ± 0.4 | 0.74 ± 0.15 | 0.6 ± 0.3 | 0.16 ± 0.12 |
| Blood/Bone | 5 ± 2 | 0.6 ± 0.4 | 0.18 ± 0.06 | 0.04 ± 0.02 | 0.007 ± 0.015 |
| Liver/Bone | 2.2 ± 0.7 | 2.3 ± 1.7 | 10 ± 4 | 7.6 ± 1.6 | 4.2 ± 1.2 |
| S. Intestine/Bone | 1.6 ± 0.6 | 1.5 ± 1.1 | 3 ± 3 | 4 ± 3 | 0.24 ± 0.07 |
| L. Intestine/Bone | 0.6 ± 0.3 | 0.26 ± 0.19 | 6 ± 7 | 10 ± 7 | 0.34 ± 0.10 |
| Kidney/Bone | 13 ± 7 | 30 ± 30 | 40 ± 30 | 46 ± 12 | 10 ± 4 |
| Carcass/Bone | | | | | 0.60 ± 0.17 |

| Ratios | 0.17 h | 1 h | 4 h | 1 d |
|---|---|---|---|---|
| $^{89}$Zr-HOPO* | | | | |
| Muscle/Bone | 0.35 ± 0.16 | 0.34 ± 0.15 | 0.4 ± 0.3 | 0.35 ± 0.09 |
| Blood/Bone | 3.1 ± 1.5 | 0.6 ± 0.4 | 0.2 ± 0.2 | 0.12 ± 0.02 |

The ratios show residual kidney and greater liver uptake for the Lu-DOTA than Lu-HOPO. Additionally, similar muscle/bone and blood/bone ratios were determined for Lu-HOPO when compared to Zr-HOPO at 1 d p.i. Without wishing to be bound by any theory, these results indicated that the Lu-HOPO complex was stable enough for further in vivo studies.

Conjugation, Radiolabeling, and In Vitro Analysis of the Bifunctional Ligand-Antibody Conjugate.

In order to assess the stability of the Lu-HOPO complex for longer periods of time in vivo, the bifunctional HOPO was conjugated to trastuzumab (HOPO-Tz) to obtain 0.95±0.08 HOPO ligands/antibody (MALDI analysis). The HOPO-Tz was radiolabeled with $^{177}$Lu ($^{177}$Lu-HOPO-Tz) with a specific activity of 4-5 mCi/mg (148-185 MBq/mg) and >98% radiochemical purity. The $^{177}$Lu-HOPO-Tz was eluted from the PD-10 column in phosphate buffered saline (PBS) with 6 mg/mL L-ascorbic acid. To assess the biological stability of the $^{177}$Lu-HOPO-Tz, 10% of the recovered $^{177}$Lu-HOPO-Tz was incubated at 37° C. in human serum. The amount of intact $^{177}$Lu-HOPO-Tz over time was assessed by radio-ITLC and showed a decrease over the course of 6 days (93±3% intact at 1 d; 89±2% intact at 3 d; 82±2% intact at 6 d). The decrease in stability of the $^{177}$Lu-HOPO-Tz complex relative to $^{177}$Lu-HOPO is similar to that which was observed for $^{89}$Zr-HOPO-Tz relative to $^{89}$Zr-HOPO. [1b]

Using a protocol similar to the $^{177}$Lu-HOPO hydroxyapatite study, $^{177}$Lu-HOPO-Tz was shown to be >97% intact over the course of 6 d. The major difference was that the $^{177}$Lu-HOPO-Tz stuck to the walls of the microcentrifuge tubes that were used in the assay as well as remaining in solution. Thus, a concerted effort was made to remove all of the hydroxyapatite from the microcentrifuge tube in these analyses and the activity remaining in the microcentrifuge tube was summed with the filtrate to obtain the total $^{177}$Lu-HOPO-Tz.

To assess the tumor targeting ability of the radioimmunoconjugate, a saturation binding assay was performed with SKOV-3 cells (human ovarian adenocarcinoma, HER2 expressing cell line). The saturation binding assay indicated that 86.0±0.7% (on ice) or 89±2% (at 37° C.) of the radioimmunoconjugate was bound to the cell pellet. Without wishing to be bound by any theory, binding about 85-95% for this assay indicates that the modified antibody targets cell surface receptors at a level similar to the unmodified antibody.

In Vivo Analysis of $^{177}$Lu-HOPO-Tz

Figure 23:
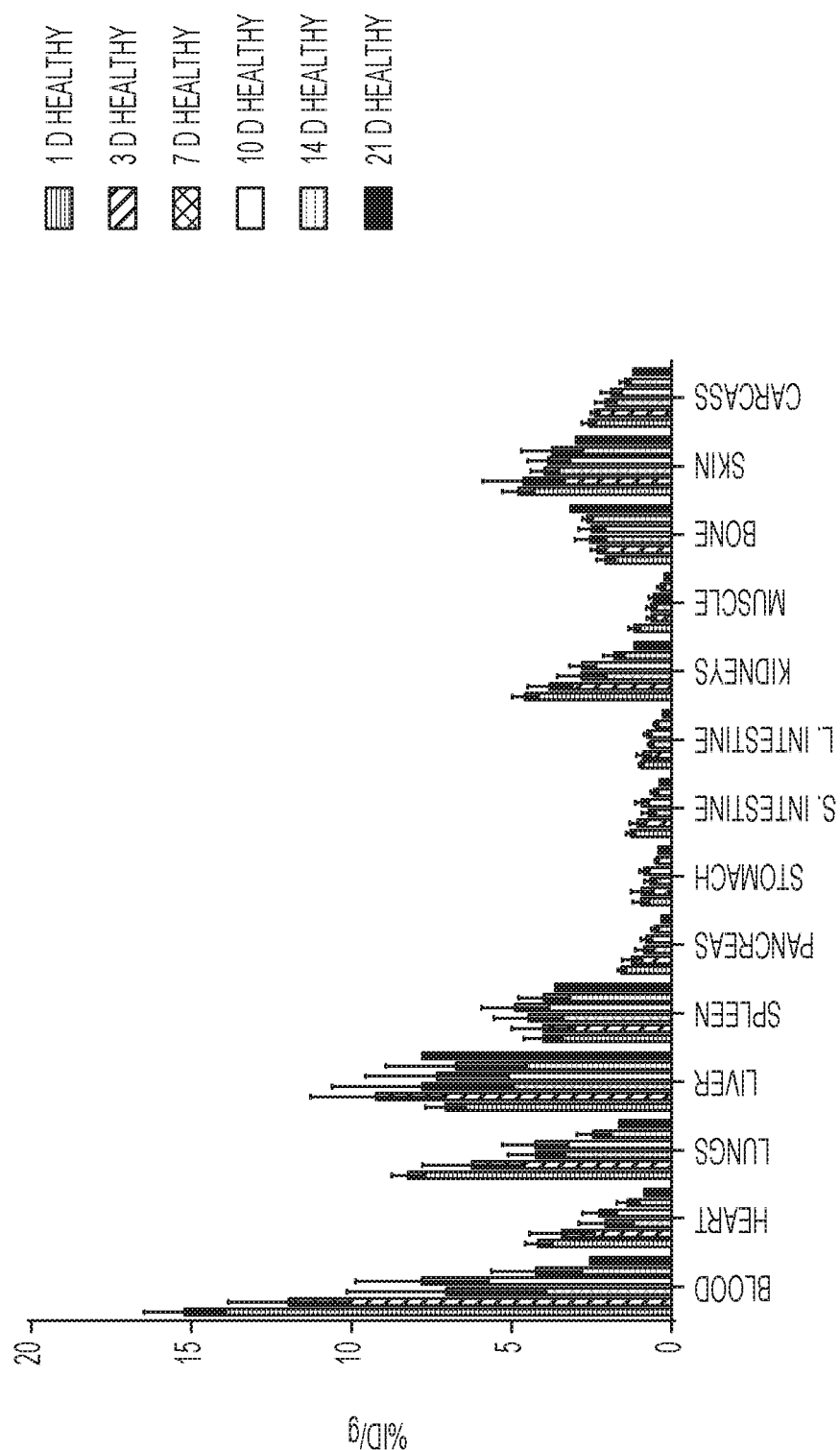
FIG. 23 shows the biodistribution of $^{177}$Lu-HOPO-Tz in healthy female nude mice from the values presented in Table 5.
Figure 24:
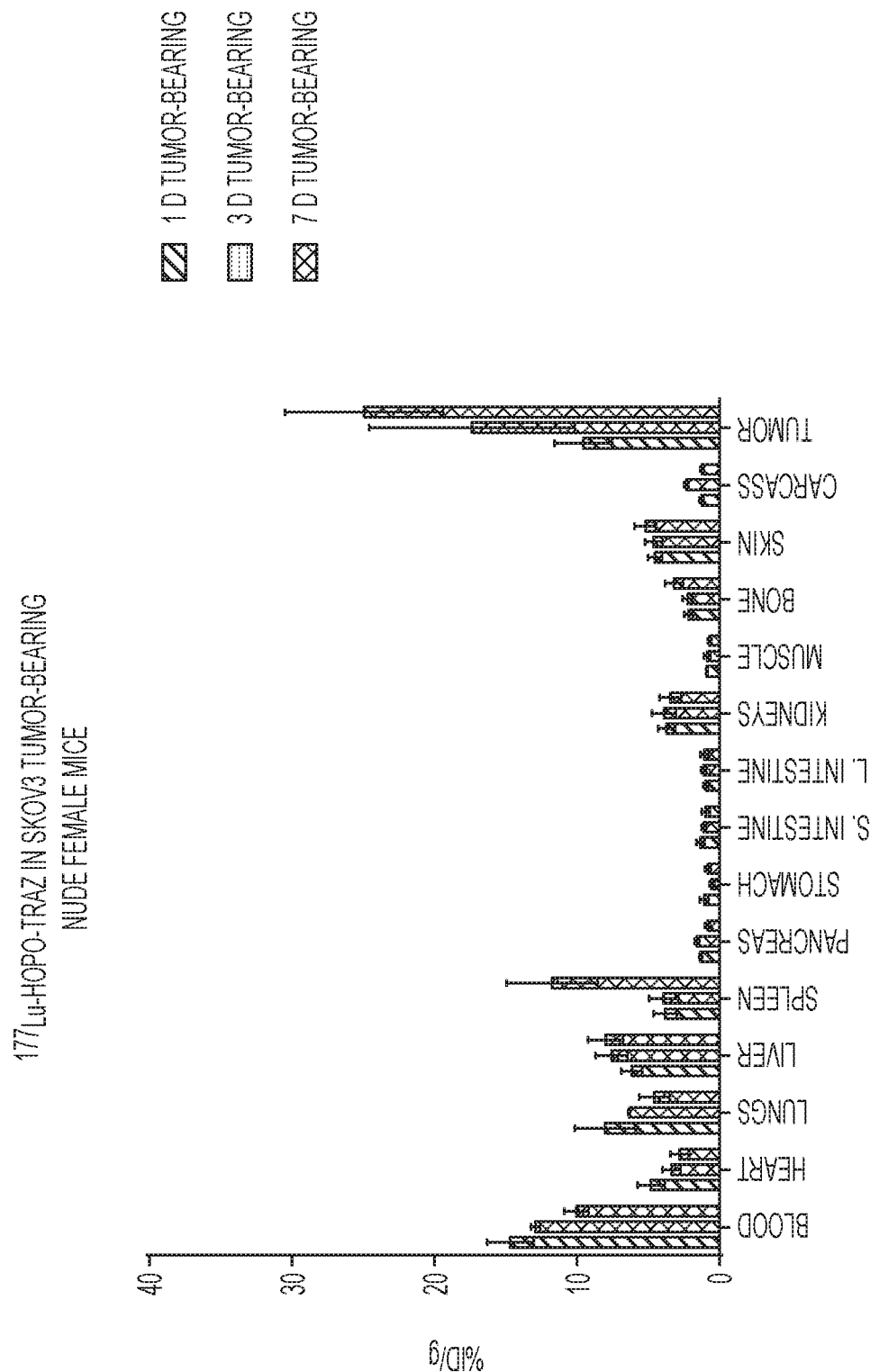
FIG. 24 shows the biodistribution of $^{177}$Lu-HOPO-Tz in SKOV-3 tumor-bearing female nude mice from the values presented in Table 5.

In order to determine if the $^{177}$Lu-HOPO-Tz was stable for in vivo delivery of $^{177}$Lu, the radioimmunoconjugate was administered to a group of SKOV-3 tumor-bearing female nude mice (four with approximately 500 µCi (18.5 MBq) or 9.54 µg for SPECT imaging; eight with approximately 50 µCi (1.85 MBq) or 0.954 µg for biodistribution) and healthy female nude mice (thirty with approximately 50 µCi (1.85 MBq) or 0.954 µg for biodistribution only). The latter group was investigated because there would not be a sink for the radioimmunoconjugate within the mouse; thus, the antibody would circulate for longer and would have the maximum metabolism of the construct. The major organ of interest to show instability was the bone and residual carcass because, without wishing to be bound to any particular theory, any free $^{177}$Lu should accumulate in the bone. The biodistribution results for these mice are in Table 5 and shown graphically in FIG. 23 and FIG. 24 (tissue ratios are given in Table 6 and Table 7).

TABLE 5

| Organ | 1 d Tumor-bearing | 1 d Healthy | 3 d Tumor-bearing | 3 d Healthy | 7 d Tumor-bearing* | 7 d Healthy | 10 d Healthy | 14 d Healthy | 21 d Healthy |
|---|---|---|---|---|---|---|---|---|---|
| Blood | 14.7 ± 1.6 | 15.2 ± 1.3 | 12.9 ± 0.3 | 12.0 ± 1.9 | 10.0 ± 0.9 | 7 ± 3 | 8 ± 2 | 4.2 ± 1.4 | 3 ± 2 |
| Heart | 4.8 ± 1.0 | 4.2 ± 0.4 | 3.4 ± 0.6 | 3.4 ± 1.0 | 2.8 ± 0.6 | 2.1 ± 0.9 | 2.3 ± 0.5 | 1.4 ± 0.3 | 0.9 ± 0.6 |
| Lung | 8 ± 2 | 8.2 ± 0.5 | 6.33 ± 0.06 | 6.2 ± 1.6 | 4.6 ± 1.1 | 4.2 ± 0.9 | 4.3 ± 1.0 | 2.4 ± 0.5 | 1.6 ± 1.2 |
| Liver | 6.2 ± 0.7 | 7.1 ± 0.6 | 7.6 ± 1.1 | 9 ± 2 | 8.0 ± 1.2 | 8 ± 3 | 7 ± 2 | 7 ± 2 | 8 ± 2 |
| Spleen | 3.8 ± 0.8 | 4.0 ± 0.6 | 3.9 ± 1.0 | 4.0 ± 1.0 | 12 ± 3 | 4.5 ± 1.1 | 4.9 ± 1.1 | 4.0 ± 0.8 | 3.6 ± 1.9 |
| Pancreas | 1.32 ± 0.10 | 1.56 ± 0.13 | 1.58 ± 0.17 | 1.2 ± 0.3 | 0.84 ± 0.17 | 0.9 ± 0.3 | 0.80 ± 0.18 | 0.54 ± 0.11 | 0.32 ± 0.19 |
| Stomach | 1.1 ± 0.3 | 1.0 ± 0.3 | 0.56 ± 0.17 | 0.9 ± 0.3 | 0.8 ± 0.2 | 0.67 ± 0.18 | 0.86 ± 0.15 | 0.47 ± 0.05 | 0.4 ± 0.2 |
| S. Intestine | 1.3 ± 0.3 | 1.29 ± 0.14 | 1.10 ± 0.15 | 1.1 ± 0.3 | 1.0 ± 0.3 | 0.7 ± 0.2 | 0.9 ± 0.2 | 0.54 ± 0.12 | 0.4 ± 0.2 |
| L. Intestine | 0.98 ± 0.16 | 0.96 ± 0.07 | 1.14 ± 0.18 | 0.9 ± 0.2 | 1.0 ± 0.3 | 0.67 ± 0.07 | 0.77 ± 0.12 | 0.50 ± 0.07 | 0.28 ± 0.09 |
| Kidneys | 3.7 ± 0.6 | 4.6 ± 0.4 | 3.9 ± 0.8 | 3.8 ± 0.7 | 3.4 ± 0.8 | 2.8 ± 0.8 | 2.8 ± 0.4 | 1.8 ± 0.3 | 1.2 ± 0.5 |
| Muscle | 0.90 ± 0.03 | 1.17 ± 0.18 | 0.9 ± 0.2 | 0.64 ± 0.13 | 0.70 ± 0.14 | 0.64 ± 0.16 | 0.57 ± 0.14 | 0.34 ± 0.10 | 0.15 ± 0.09 |
| Bone | 2.2 ± 0.3 | 2.1 ± 0.3 | 2.2 ± 0.4 | 2.3 ± 0.2 | 3.2 ± 0.6 | 2.5 ± 0.5 | 2.5 ± 0.4 | 2.64 ± 0.16 | 3.2 ± 0.6 |
| Skin | 4.5 ± 0.5 | 4.8 ± 0.5 | 4.6 ± 0.6 | 4.6 ± 1.3 | 5.2 ± 0.8 | 4.0 ± 0.4 | 3.9 ± 0.7 | 3.7 ± 1.0 | 3.0 ± 1.1 |
| Carcass | 1.27 ± 0.13 | 2.6 ± 0.2 | 2.34 ± 0.15 | 2.39 ± 0.15 | 1.23 ± 0.12 | 2.1 ± 0.3 | 1.9 ± 0.3 | 1.45 ± 0.16 | 1.2 ± 0.4 |
| Tumor | 10 ± 2 | — | 17 ± 7 | — | 25 ± 6 | — | — | — | — |

TABLE 6

| | 1 d Healthy | 3d Healthy | 7 d Healthy | 10 d Healthy | 14 d Healthy | 21 d Healthy |
|---|---|---|---|---|---|---|
| Blood | 7.4 ± 1.2 | 5.2 ± 1.0 | 2.8 ± 1.3 | 3.1 ± 1.0 | 1.6 ± 0.5 | 0.8 ± 0.8 |
| Heart | 2.0 ± 0.3 | 1.5 ± 0.5 | 0.8 ± 0.4 | 0.9 ± 0.3 | 0.52 ± 0.14 | 0.27 ± 0.18 |
| Lungs | 4.0 ± 0.6 | 2.7 ± 0.7 | 1.7 ± 0.5 | 1.7 ± 0.5 | 0.9 ± 0.2 | 0.5 ± 0.4 |
| Liver | 3.4 ± 0.6 | 4.0 ± 1.0 | 3.1 ± 1.3 | 2.9 ± 1.0 | 2.6 ± 0.8 | 2.5 ± 0.9 |
| Spleen | 1.9 ± 0.4 | 1.7 ± 0.5 | 1.8 ± 0.5 | 2.0 ± 0.5 | 1.5 ± 0.3 | 1.2 ± 0.6 |
| Pancreas | 0.76 ± 0.12 | 0.54 ± 0.14 | 0.34 ± 0.13 | 0.32 ± 0.09 | 0.20 ± 0.04 | 0.10 ± 0.06 |
| Stomach | 0.47 ± 0.14 | 0.40 ± 0.15 | 0.26 ± 0.09 | 0.34 ± 0.08 | 0.18 ± 0.02 | 0.13 ± 0.07 |
| S. Intestine | 0.63 ± 0.11 | 0.46 ± 0.12 | 0.28 ± 0.10 | 0.37 ± 0.11 | 0.21 ± 0.05 | 0.12 ± 0.07 |
| L. Intestine | 0.47 ± 0.07 | 0.38 ± 0.10 | 0.26 ± 0.06 | 0.31 ± 0.07 | 0.19 ± 0.03 | 0.09 ± 0.03 |
| Kidneys | 2.2 ± 0.4 | 1.7 ± 0.3 | 1.1 ± 0.4 | 1.1 ± 0.2 | 0.69 ± 0.14 | 0.37 ± 0.19 |
| Muscle | 0.57 ± 0.12 | 0.28 ± 0.06 | 0.25 ± 0.08 | 0.23 ± 0.07 | 0.13 ± 0.04 | 0.05 ± 0.03 |
| Skin | 2.3 ± 0.4 | 2.0 ± 0.6 | 1.6 ± 0.3 | 1.5 ± 0.4 | 1.4 ± 0.4 | 0.9 ± 0.4 |
| Carcass | 1.3 ± 0.2 | 1.04 ± 0.12 | 0.8 ± 0.2 | 0.76 ± 0.18 | 0.55 ± 0.07 | 0.38 ± 0.15 |

TABLE 7

| | Tissue/Bone Ratios | | | Tumor/Tissue Ratios | | |
|---|---|---|---|---|---|---|
| | 1 d Tumor | 3 d Tumor | 7 d Tumor | 1 d Tumor | 3 d Tumor | 7 d Tumor |
| Blood | 6.8 ± 1.2 | 5.8 ± 1.0 | 3.1 ± 0.7 | 0.65 ± 0.16 | 1.3 ± 0.6 | 2.5 ± 0.6 |
| Heart | 2.2 ± 0.5 | 1.5 ± 0.4 | 0.9 ± 0.3 | 2.0 ± 0.6 | 5 ± 2 | 9 ± 3 |
| Lungs | 3.7 ± 1.1 | 2.8 ± 0.5 | 1.4 ± 0.4 | 1.2 ± 0.4 | 2.7 ± 1.1 | 5.5 ± 1.8 |
| Liver | 2.8 ± 0.5 | 3.4 ± 0.8 | 2.5 ± 0.6 | 1.6 ± 0.4 | 2.3 ± 1.0 | 3.1 ± 0.8 |
| Spleen | 1.8 ± 0.4 | 1.8 ± 0.5 | 3.7 ± 1.2 | 2.5 ± 0.7 | 4 ± 2 | 2.1 ± 0.7 |
| Pancreas | 0.61 ± 0.10 | 0.70 ± 0.14 | 0.26 ± 0.07 | 7.3 ± 1.6 | 11 ± 5 | 30 ± 9 |
| Stomach | 0.49 ± 0.15 | 0.25 ± 0.08 | 0.26 ± 0.08 | 9 ± 3 | 31 ± 16 | 30 ± 10 |
| S. Intestine | 0.62 ± 0.16 | 0.49 ± 0.11 | 0.30 ± 0.11 | 7 ± 2 | 16 ± 7 | 26 ± 10 |
| L. Intestine | 0.45 ± 0.10 | 0.51 ± 0.12 | 0.33 ± 0.11 | 10 ± 3 | 15 ± 7 | 24 ± 8 |
| Kidneys | 1.7 ± 0.4 | 1.7 ± 0.5 | 1.1 ± 0.3 | 2.6 ± 0.7 | 4 ± 2 | 7 ± 2 |
| Muscle | 0.41 ± 0.06 | 0.38 ± 0.12 | 0.22 ± 0.06 | 11 ± 2 | 20 ± 10 | 36 ± 11 |
| Bone | — | — | — | 4.4 ± 1.1 | 8 ± 3 | 8 ± 2 |
| Skin | 2.1 ± 0.4 | 2.1 ± 0.4 | 1.6 ± 0.4 | 2.1 ± 0.5 | 3.8 ± 1.6 | 4.8 ± 1.3 |
| Carcass | 0.58 ± 0.10 | 1.04 ± 0.19 | 0.38 ± 0.08 | — | — | — |
| Tumor | 4.4 ± 1.1 | 8 ± 3 | 8 ± 2 | — | — | — |

Figure 25:
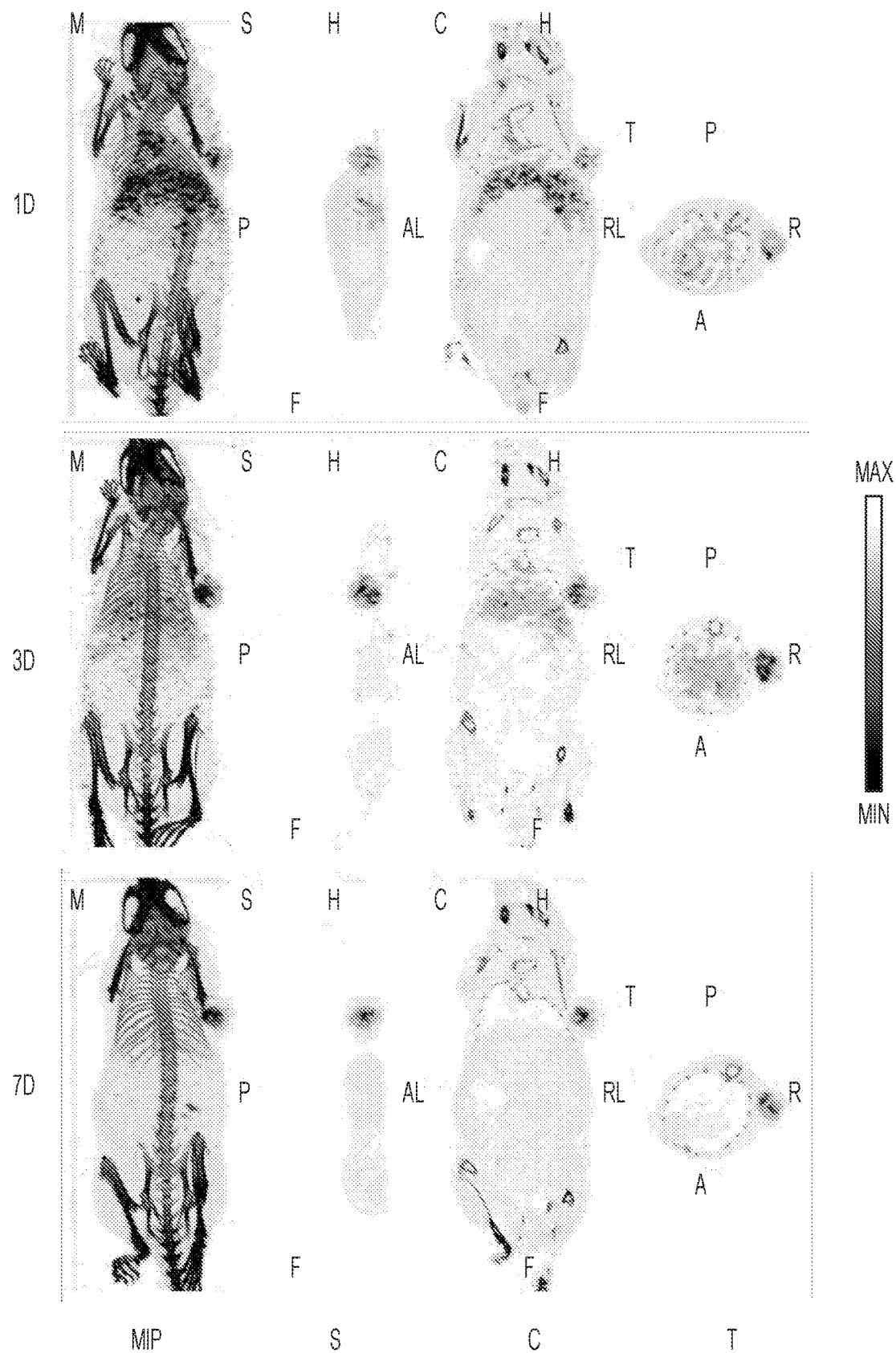
FIG. 25 shows single photon emission computed tomography (SPECT)/CT results of the $^{177}$Lu-HOPO-Tz biodistribution in SKOV3 tumor-bearing nude female mice at 1, 3, and 7 days post injection. MIP is maximum intensity projection. S is the sagittal, C is the coronal, and T is the transverse slice at the tumor level.

Additionally, the single photon emission computed tomography/computed tomography (SPECT/CT) images at 1, 3, and 7 d p.i. of one of the mice that received an imaging dose are shown in FIG. 25. The tumor accumulation (10±2% ID/g at 1 d; 17±7% ID/g at 3 d; and 25±6% ID/g at 7 d), although lower than previously reported for other trastuzumab-based radioimmunoconjugates, is clearly visible in the maximum intensity projections (MIPs) shown in FIG. 25. Additionally, the muscle-to-bone ratios reported here (0.28±0.06 (healthy) and 0.38±0.12 (tumor-bearing)) are similar to those previously reported at 3 d p.i. for tumor-bearing mice injected with $^{111}$In-octapa-Tz (0.4±0.2), $^{177}$Lu-octapa-Tz (0.26±0.17), $^{111}$In-DOTA-Tz (0.45±0.19), $^{177}$Lu-DOTA-Tz (0.31±0.10), and [89]Zr-HOPO-Tz (0.41±0.11). This result holds true at 7 and 14 d p.i. for the comparison of $^{177}$Lu-HOPO-Tz (0.25±0.08 healthy 7 d, 0.13±0.04 healthy 14 d, and 0.22±0.06 tumor-bearing 7 d) to [89]Zr-HOPO-Tz (0.32±0.08 tumor-bearing 7 d and 0.17±0.05 tumor-bearing 14 d). Additionally, the 7 d p.i., muscle-to-bone ratios for $^{177}$Lu-HOPO-Tz are statistically the same as the 6 d p.i. muscle-to-bone ratios for just the $^{177}$Lu-HOPO. From these results, the potential loss of the radiometals from the chelators appears to be similar across each of the systems investigated in these studies, which is quite low. Interestingly, the imaging mice (7 d tumor-bearing) were injected with 10 times the radioactivity compared to the healthy mice (7 d healthy), which did not noticeably affect the muscle-to-bone ratio and, without wishing to be bound to any particular theory, further indicates the complex stability.

Besides the accumulation in the bone, the carcasses from the $^{177}$Lu-HOPO-Tz studies were collected and both an overall % ID/g and % ID from the entire mouse (Table 8) and the % ID/g (Table 5) of just the remaining carcasses were calculated. These results show that in certain embodiments, in both the healthy and the tumor-bearing mice, the $^{177}$Lu is being excreted rather than retained by the mouse. In certain embodiments, the % ID of the mice injected with 10 times the construct for imaging (7 d tumor-bearing mice) have much lower % ID remaining in the mice compared to the healthy mice at 7 d p.i.

TABLE 8

|  | t (d) | % ID/g | % ID |
|---|---|---|---|
| Healthy | 1 | 2.86 ± 0.2 | 76.0 ± 1.5 |
|  | 3 | 2.67 ± 0.18 | 68 ± 3 |
|  | 7 | 2.34 ± 0.14 | 63 ± 3 |
|  | 10 | 2.2 ± 0.2 | 56 ± 5 |
|  | 14 | 1.67 ± 0.19 | 45 ± 4 |
|  | 21 | 1.5 ± 0.4 | 41 ± 8 |
| SKOV-3 tumor-bearing | 1 | 2.8 ± 0.3 | 75 ± 7 |
|  | 3 | 2.68 ± 0.16 | 70 ± 4 |
|  | 7 | 2.0 ± 0.2 | 46 ± 3 |

Figure 26:
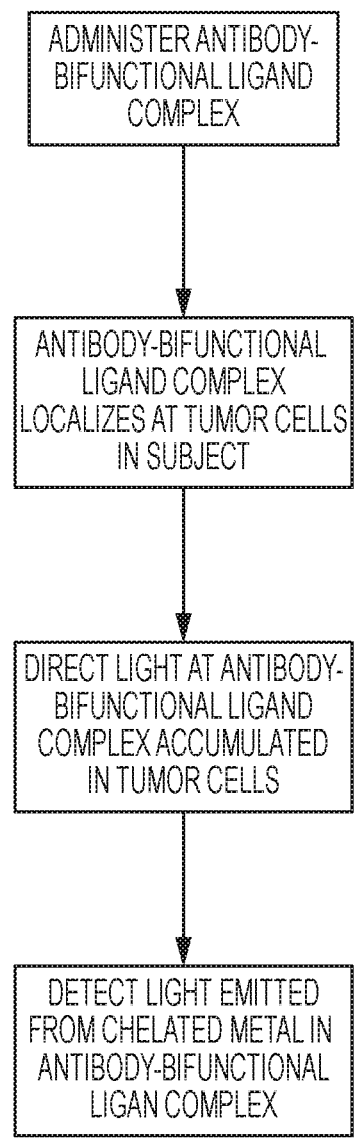
FIG. 26 shows an illustrative embodiment of a method to use light for detection of antibody-bifunctional ligand complexes that have accumulated in regions targeted by the antibody where the complexes contain a chelated metal ion that is photoluminescent.

In certain embodiments, p-SCN-Bn-HOPO is used with europium(III) or other lanthanide ions for optical imaging. In these embodiments, light of wavelength 300-400 nm excite the hydroxypyridinone groups for energy transfer to the Eu(III) (or other lanthanide ion). After excitation, the Eu(III) emits light in the 660 nm range. Other lanthanides can emit in the visible or near infrared (IR) range. FIG. 26 shows an illustrative embodiment of a method that utilizes a bifunctional ligand and a lanthanide ion complex to detect complexes that have been attached to their targets. The bifunctional ligand chelated to a photoluminescent metal (e.g., europium(III)) can be complexed with an antibody that is capable of complexing to the desired location in the subject. Upon administration of the bifunctional ligand-antibody complex and the complexing of the complex to the region of interest in the subject, a light can be directed at the region of interest. In certain embodiments, the region of interest comprises one or more tumor cells. The directed light can be absorbed by the bifunctional ligand and stimulate photoluminescence from the chelated metal that can be detected. The detected light can be used to signal the presence of tumor cells in the region or to generate an image of the tumor that can be used for gaining quantitative information about the tumor and/or one or more tumor cells, such as its/their dimensions (e.g., size, volume), shape, precise location, or rate of growth or shrinkage. Additional information about one or more moiety expressions (e.g., protein expressions) of the tumor can also be gained based on whether association of one or more antibodies utilized in the composition occurs with one or more tumor cells in the subject.

Materials and Methods
Chemical Synthesis

Attachment to an amine can be accomplished using the original spermine backbone at N1 as N5 is already a tertiary amine. Attachment to a carbon requires the synthesis of a new nitrogen backbone with a carbon sidechain. An initial scheme for positioning the linker off C2 is to build the ligand's backbone using commercially available Fmoc-(R)-3-amino-4-(4-nitro-phenyl)-butyric acid in a reaction with spermidine to add a nitrobenzyl group to the C2 position. This nitro group can then be converted to an amine which can be used to attach a spacer in a similar fashion as done with the N1 position.

The construction of the spacer can be partially determined by the attachment point since it can either have to react with an amine if attached at position N1 or be built off whatever carbon side-chain is used to attach at position C2. For linkers attached at N1, the length of the spacer can be easily altered because there are more commercially available reagents for reaction with the amine of spermine. However, for attachment at C2, the starting materials need to be synthesized for reaction with spermidine to add the spacer to the backbone. Spacers composed of alkyl chain, polylysine chain, or polyethylene glycol (PEG) chain can be evaluated. The polylysines and PEG chains improve the water solubility and facilitate conjugation. Commercially available heterobifunctional PEG cross linkers can be used in the synthesis of the PEG derivatives with one end attached to the ligand and the other to the conjugating functionality. Both of the functional groups proposed for conjugation to an antibody react with the amine of a lysine residue. The choice of conjugation chemistries can broaden the generated libraries in order to increase the opportunity of finding an improved functional ligand. Attaching the spacer at the N1 position (e.g., the first position of the chain) or at the C2 position (e.g., the second position of the chain) can influence the radiolabeling of the chelator to Zr or other metals and the stability of the construct.

Figure 27:
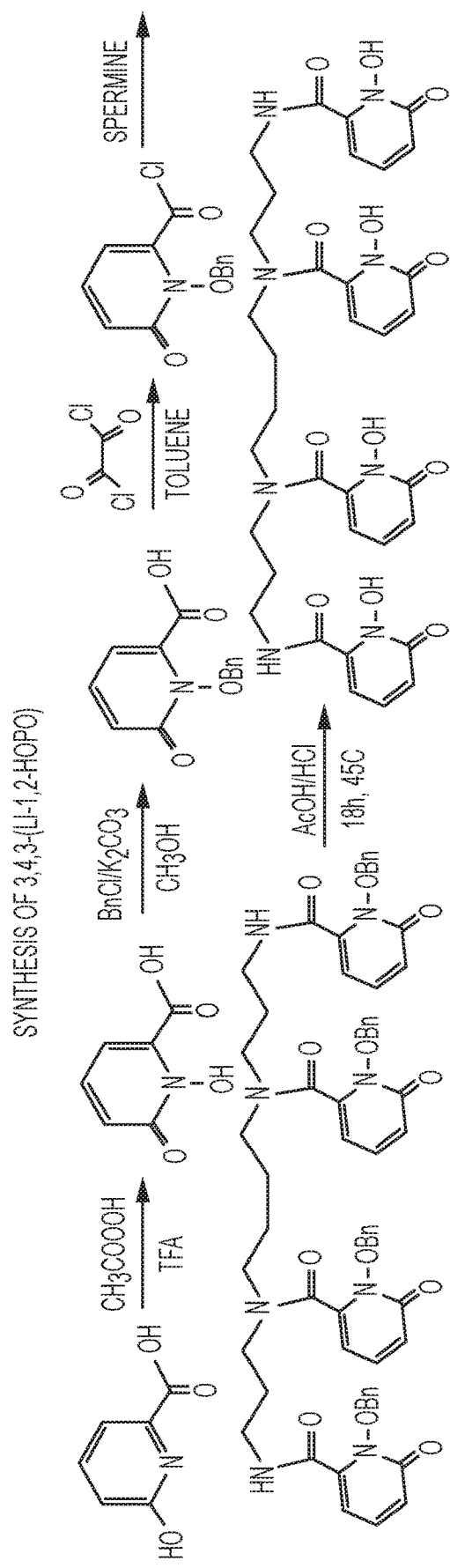
FIG. 27 shows a modular synthetic pathway of 3,4,3-(LI-1,2-HOPO). In certain embodiments, an acid chloride binding group is coupled to an amine backbone for switching out the acid chlorides to study different binding groups as well as use different amine backbones to make different shaped ligands. The LICAM ligand has been synthesized in a similar manner using a protected catechol acid chloride.
Figure 28A:
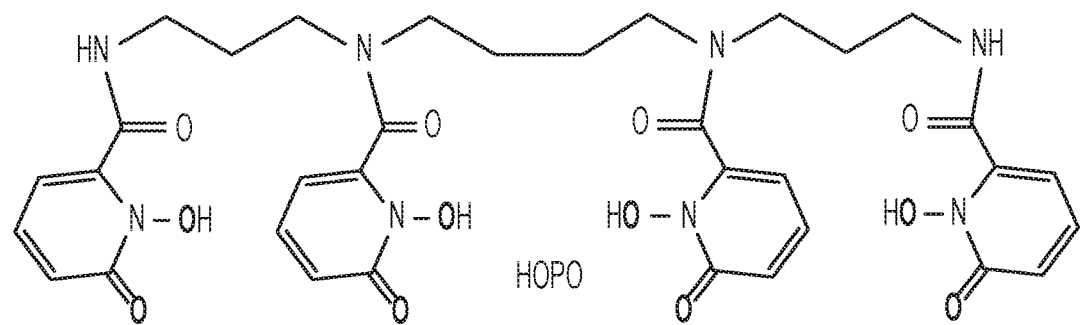
FIG. 28A and FIG. 28B show two exemplary structures of ligands that include hydroxypyridinone and catechol groups in the same acyclic, octadentate ligand structure, respectively. The two ligands are both Raymond ligands (Hydroxypyridinone ligand=3,4,3-(LI-1,2-HOPO)="HOPO" (FIG. 28A)) (Catechol ligand=3,4,3-LICAM="LICAM" (FIG. 28B)).
Figure 28B:
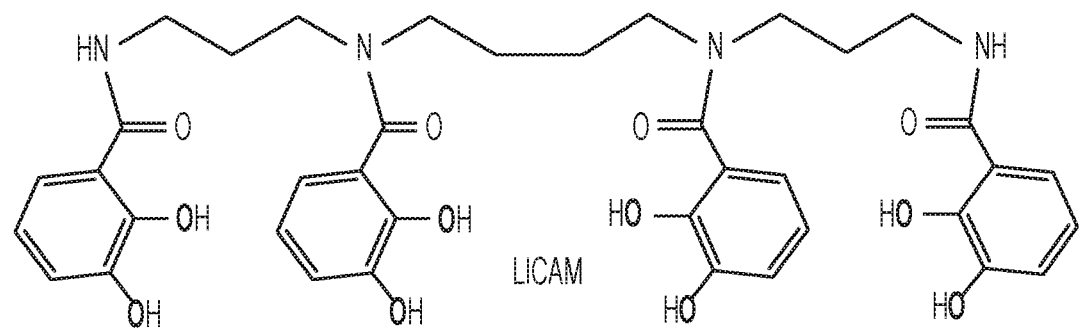

FIG. 27 shows a modular synthetic pathway of 3,4,3-(LI-1,2-HOPO). In certain embodiments, an acid chloride binding group can be coupled to an amine backbone for switching out the acid chlorides to study different binding groups as well as use different amine backbones to make different shaped ligands. The LICAM ligand was synthesized in the same manner using a protected catechol acid chloride. FIG. 28A and FIG. 28B show two exemplary acyclic octadentate ligands based on HOPO and catechol functional groups, respectively.

Figure 29:
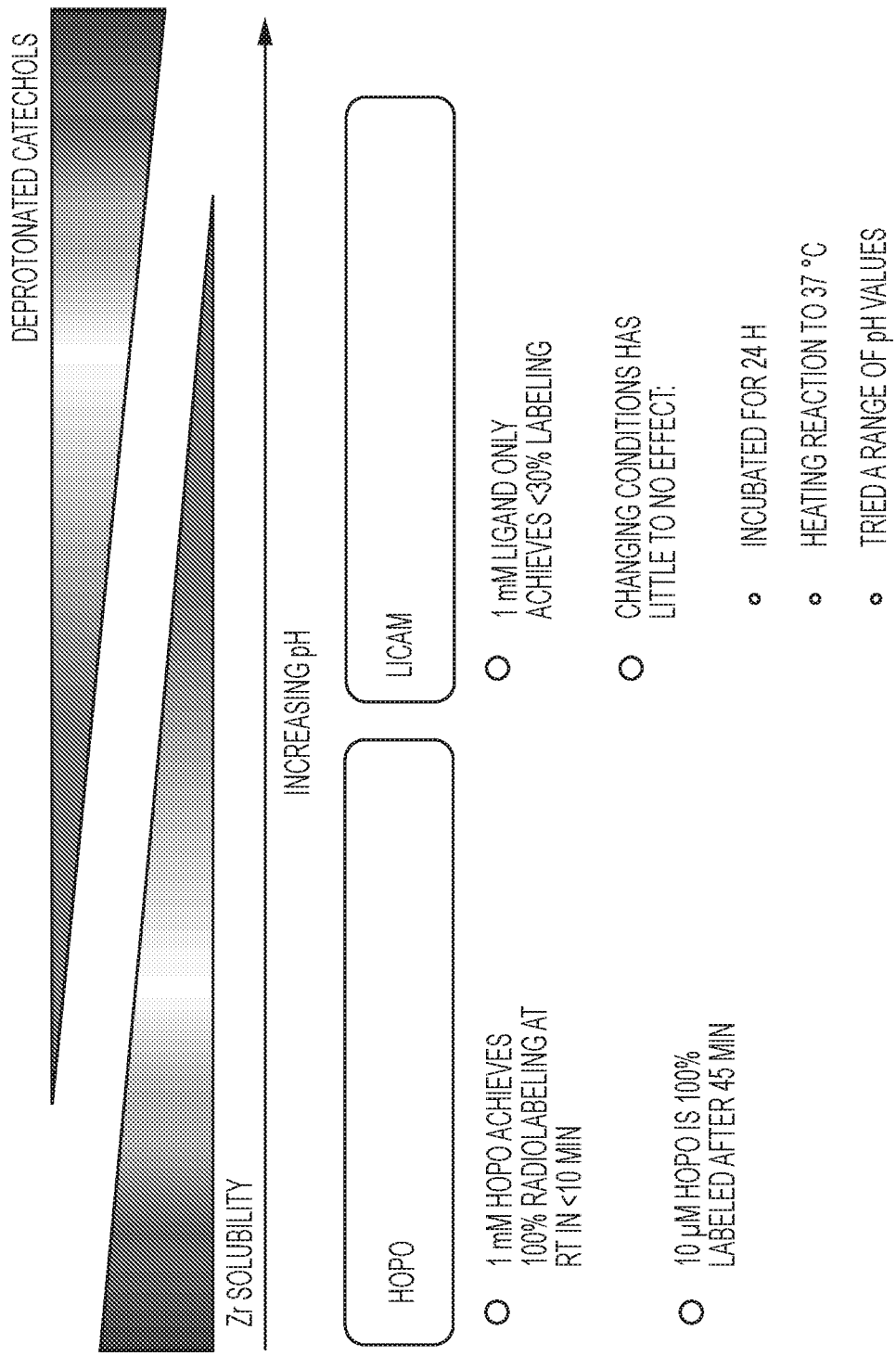
FIG. 29 shows a schematic of Zr solubility and deprotonated catechols as a function of pH and advantages of HOPO radiolabeling compared to LICAM radiolabeling.

As shown in FIG. 29, radiolabeling with $^{89}$Zr starts with a solution of $^{89}$Zr in 1M oxalic acid which is first neutralized to a pH (e.g., of 7) with sodium carbonate. This neutralized Zr solution is used to label the ligands and monitor the reactions by radio-ITLC. For initial tests, relatively high concentrations of ligand at 1 mM the HOPO ligand labeled with 100% efficiency at room temperature within 10 minutes of the addition of $^{89}$Zr. At 10 μM the HOPO ligand attained 100% radiolabeling within 45 min. In contrast, even at 1 mM, the LICAM ligand achieved less than 30% radiolabeling despite an increase in incubation time, addition of heat, and varying pH. Without having to be bound by theory, this is most likely due to the higher pKa of the catechol binding groups compared to the hydroxypyridinones. At low pH, the catechols are not fully deprotonated, but as the pH of the reaction the $^{89}$Zr increase, $^{89}$Zr begins to precipitate out of solution due to poor solubility in aqueous solution at higher pH. This incompatibility between the base strength of the binding groups and the workable pH range of $^{89}$Zr and antibodies determined that the LICAM ligand was not favorable for $^{89}$Zr chelation.

In certain embodiments, the bifunctional ligands are tested by conjugation to trastuzumab, radiolabeling with $^{89}$Zr, and investigation of the chemical and biological properties.

Figure 30A:
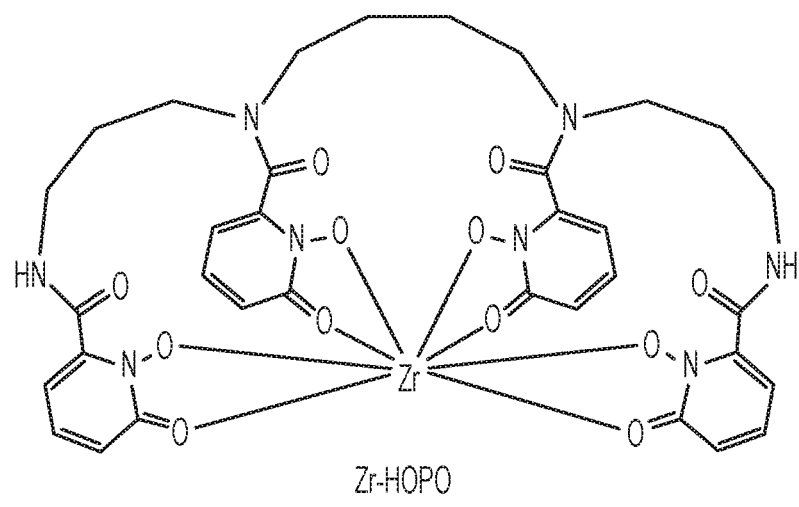
FIG. 30A and FIG. 30B show $^{89}$Zr-HOPO and $^{89}$Zr-LICAM ligands and values of mass spectrometry peaks, respectively.
Figure 30B:
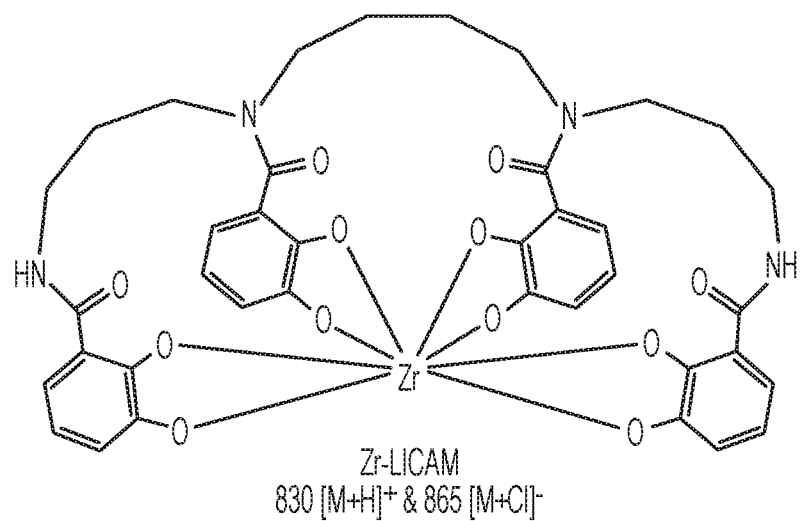

FIG. 30A and FIG. 30B show $^{89}$Zr-HOPO and Zr-LICAM ligands and values of mass spectrometry peaks, respectively. FIG. 29 shows a schematic of Zr solubility and deprotonated catechols as a function of pH and advantages of HOPO radiolabeling compared to LICAM radiolabeling.

At least one purpose behind a bifunctional ligand is to both bind a metal and form an attachment to a targeting vector (e.g., an antibody). After synthesis of the ligands, the ligands can be conjugated to an antibody and radiolabeling the complex. In certain embodiments, trastuzumab can be selected due to the availability of the antibody and the abundance of previous PET imaging data. Moreover, trastuzumab has been previously been tested when labeled with $^{89}$Zr-DFO so that direct comparisons can be made between the new ligands and the established standard.

Characterization

The characterization of the ligands described herein can include elemental analysis, nuclear magnetic resonance spectroscopy (NMR), mass spectrometry (MS), and high pressure liquid chromatography (HPLC) analysis. The MS studies can include electrospray ionization MS (ESI-MS), high resolution MS (HRMS), and liquid chromatography MS (LCMS).

HPLC purification produced final products as well as many intermediates described herein. The purification of these compounds can be carried out largely using a Symmetry C18 prep column (100 Å, 5 m, 19 mm×100 mm, Waters, Milford, Mass.).

Figure 31:
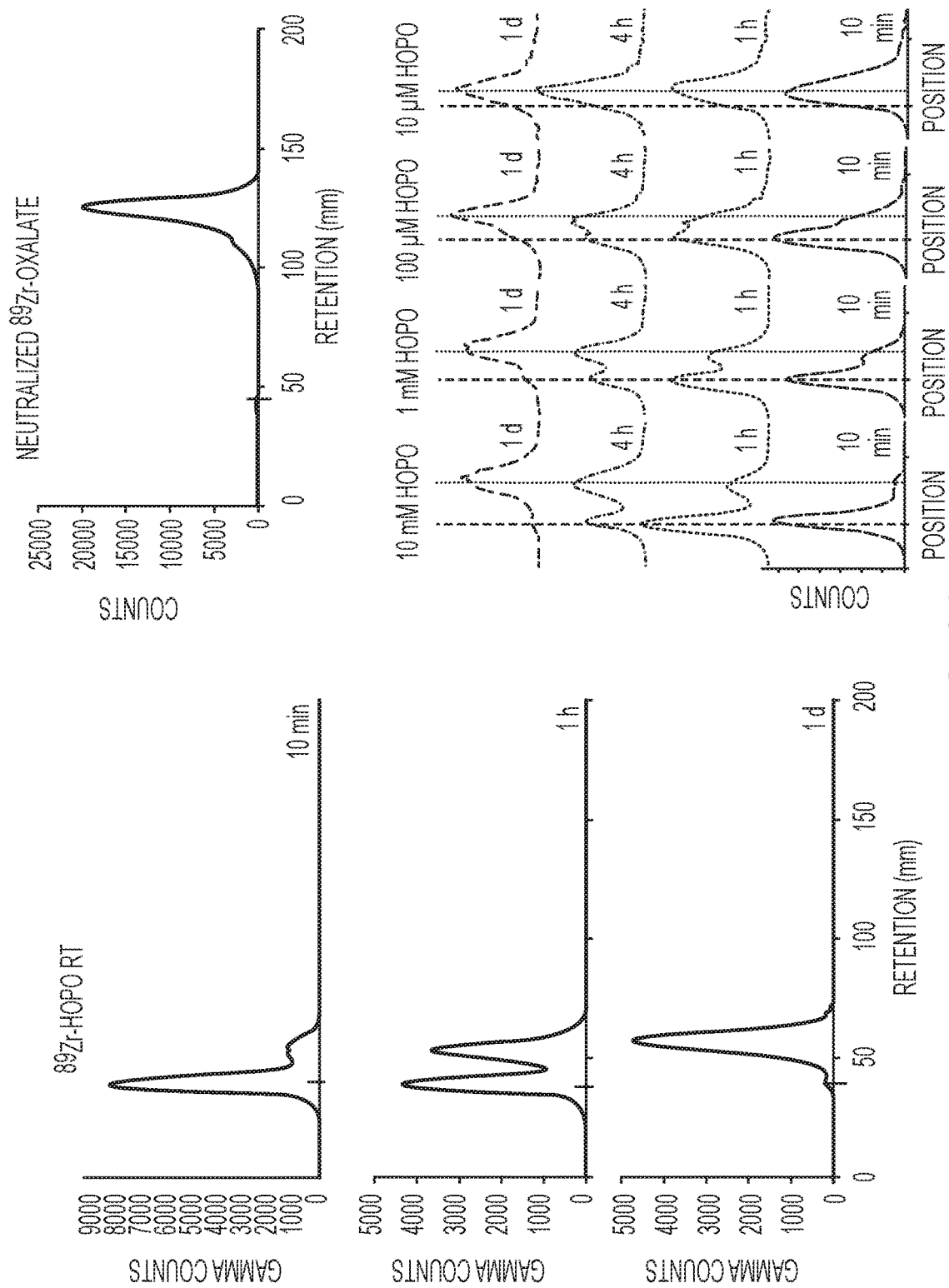
FIG. 31 shows $^{89}$Zr-HOPO radiolabeling at 10 minutes, 1 hour, 1 day, and neutralized $^{89}$Zr-oxalate.
Figure 32:
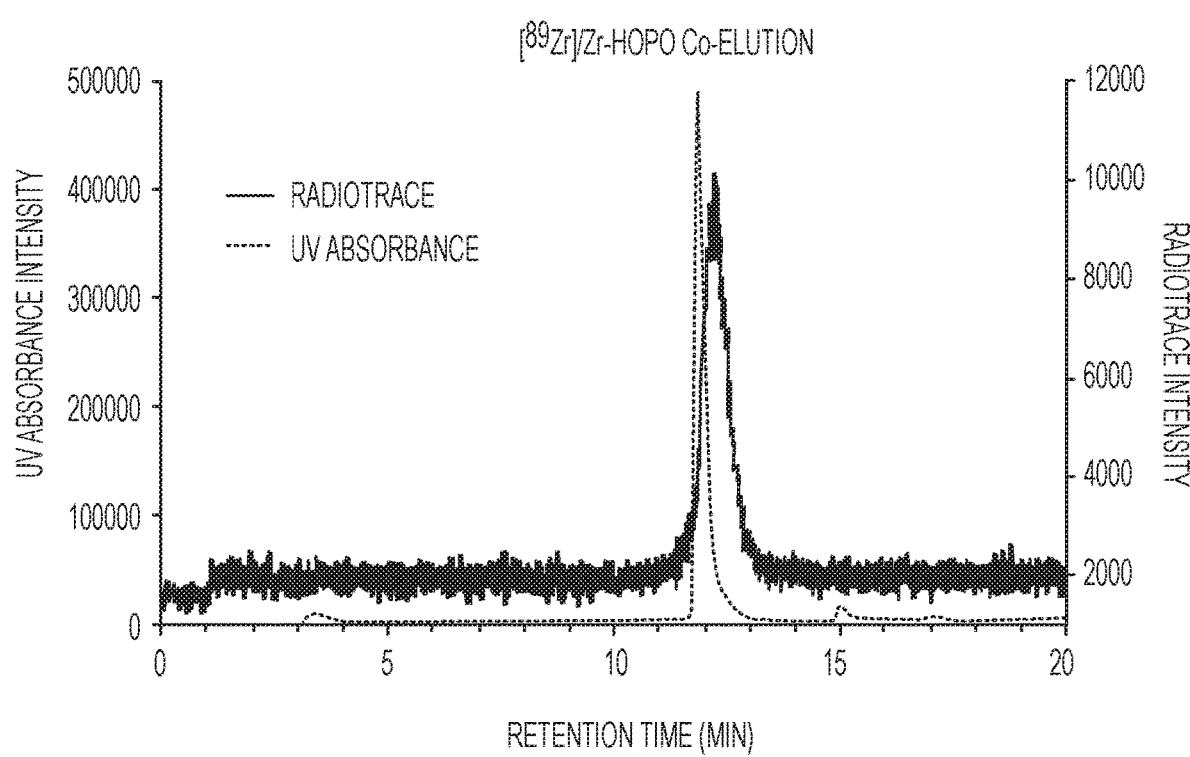
FIG. 32 shows [$^{89}$Zr]/Zr-HOPO co-elution. The HOPO ligand was radiolabeled and co-injected into hot $^{89}$Zr-HOPO complex with cold, characterized Zr-HOPO complex. The UV measurement is a result of the cold complex and the radiotrace comes from the hot complex. Taking into account the delay due to the sequential configuration of the detectors on the HPLC system, this shows a good co-elution between the two signals which confirms the identity of the radioactive species.

When monitoring the reaction by ITLC (FIG. 31), the radiolabeling initially appeared to give a single peak with a small shoulder. However, over time this small bump developed into a second peak suggesting two distinct species. This second peak slowly grew over time suggesting an initial kinetic product which converts into a second thermodynamically stable product. The behavior of the two peaks was shown to be somewhat concentration dependent with the relative intensities of the initial peaks and their separation on ITLC changing as the concentration of the ligand decreases. Importantly, the $^{89}$Zr is never released during the conversion. Without wishing to be bound by theory, this suggests some sort of intramolecular rearrangement. The identity of the radioactive species was confirmed by co-injecting a hot $^{89}$Zr-HOPO complex with a cold, characterized Zr-HOPO complex where the cold Zr-HOPO complex was formed using ZrCl$_4$ as a Zr source. The co-elution from HPLC of the two species as shown in FIG. 32 confirms the identity of the radioactive complex.

Computational Studies

DFT-based computations have been used previously to identify the lowest energy conformation of Zr(IV) complexes. Further improvements in the method and basis set choices for Zn(IV) can yield an enhanced ability to determine (1) equilibrium structures of the complexes and their relative energies, and (2) the impact of the linking group attachment on the Zr(IV)-3,4,3-(LI-1,2-HOPO) complex. Thus, several methods and basis sets to determine the computational level required to obtain reliable structures and energetics for Zr(IV) model complexes can be determined. Follow-up can then determine the effect of methylating the chelator at various attachment points (e.g., N1-C7 in FIG. 3) to mimic the effect of the linking group on the complex. (Note that attachment to any of the carbon atoms creates a chiral center. Both structures can be interrogated in silico.) These computational results can be compared to the experimental results for those compounds that are synthesized to inform further ligand improvement in a synergistic manner.

Figure 33:
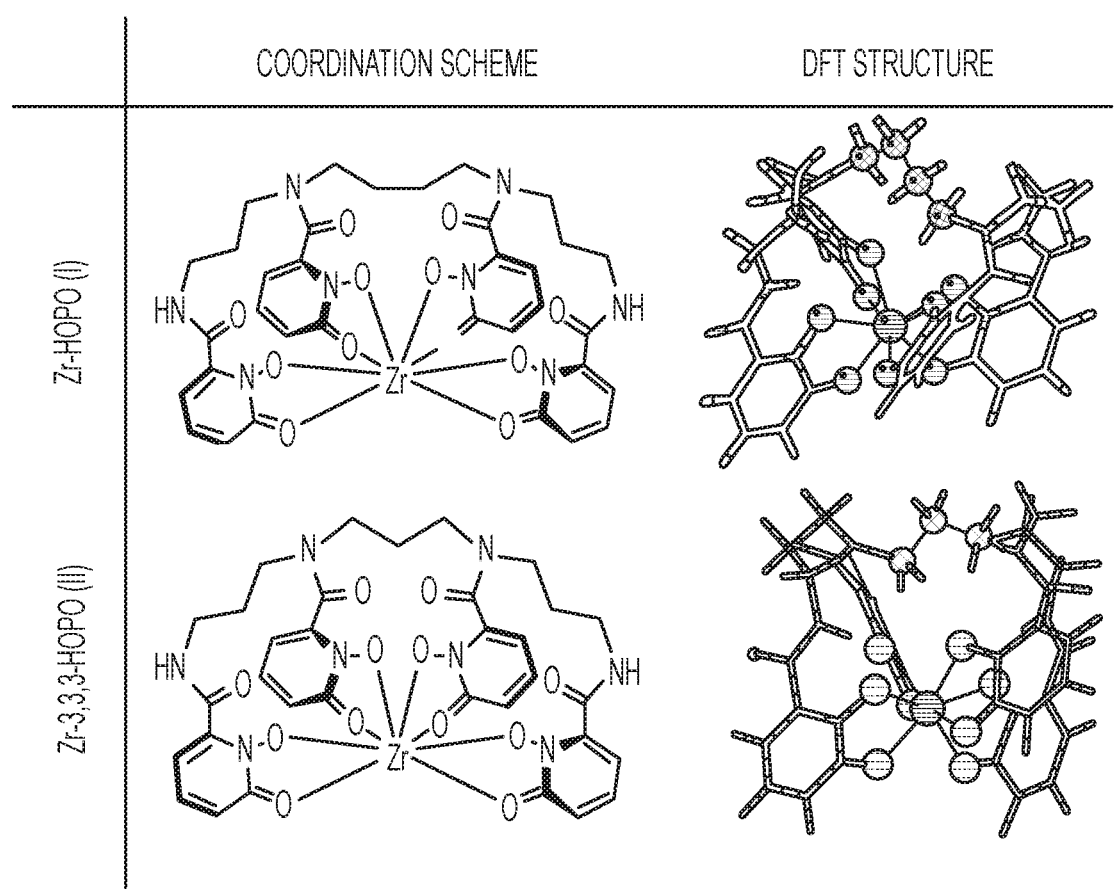
FIG. 33 shows 8 coordinate binding of $^{89}$Zr-HOPO (I) and Zr-3,3,3-HOPO (II) DFT structures. The Zr—O bond distances are shorter in the $^{89}$Zr-HOPO complexes than the $^{89}$Zr-DFO complexes.
Figure 36:
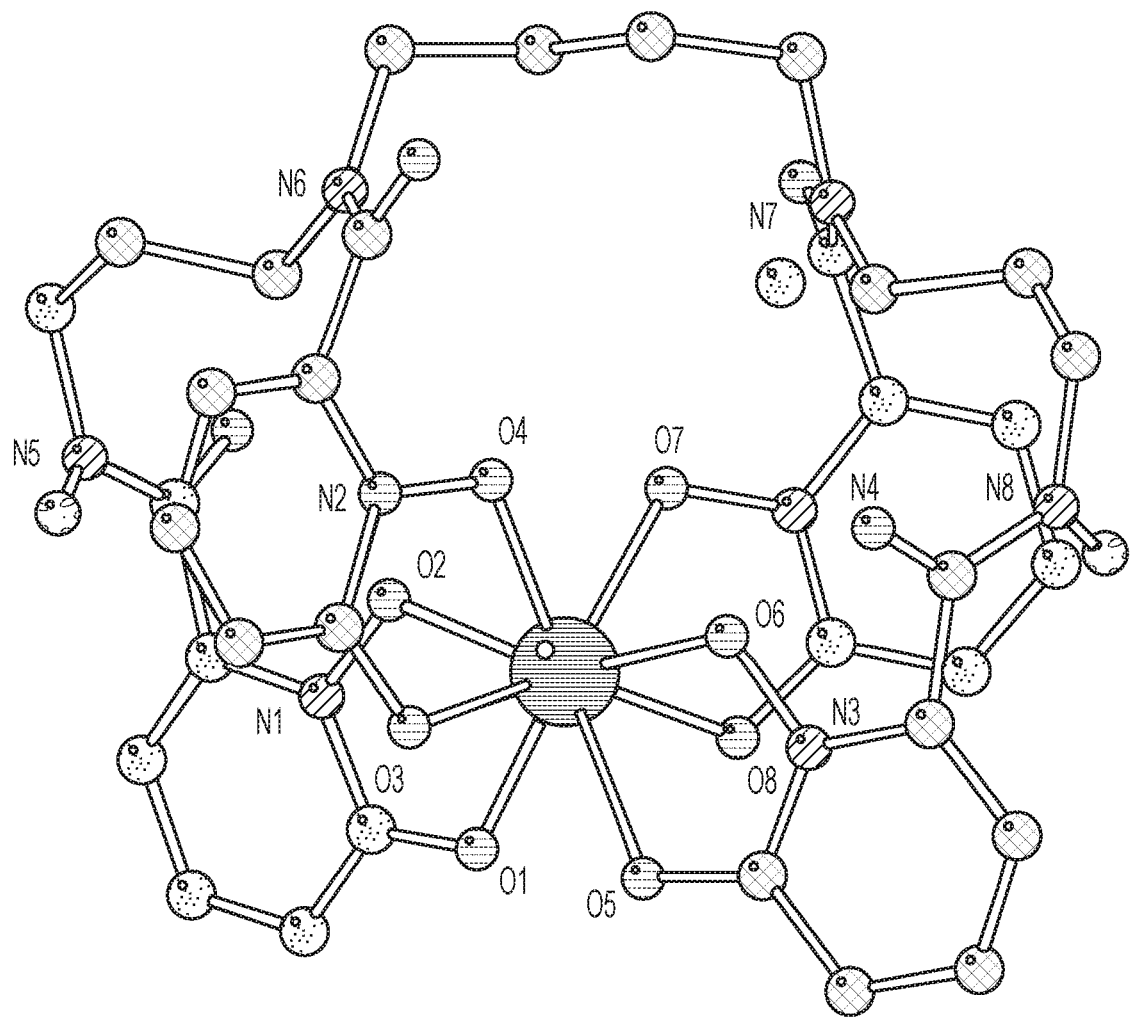
FIG. 36 shows a crystal structure that confirms 8 coordinate binding in a square antiprism geometry and that bond lengths are even shorter than DFT predictions.

FIG. 33 shows 8 coordinate binding of $^{89}$Zr-HOPO (I) and Zr-3,3,3-HOPO (II) DFT structures. The Zr—O bond distances are shorter in the $^{89}$Zr-HOPO complexes than the $^{89}$Zr-DFO complexes as shown in FIG. 34 and FIG. 35. FIG. 36 shows 8 coordinate binding in a square antiprism geometry and that bond lengths are even shorter than DFT predictions.

As the HOPO-trastuzumab has shown less efficient radiolabeling than DFO-trastuzumab, molecular dynamics simulations of the bifunctional ligands conjugated to the antibody (but without the metal center) can be performed to investigate the effect of the linker (e.g., size and functional groups) on the availability of the ligand toward radiometal complexation. These tests can be done in gas and solution phases (both implicit and explicit) to elucidate the effects of the various linkers on the structure and dynamics of the overall bifunctional chelator.

Figure 37:
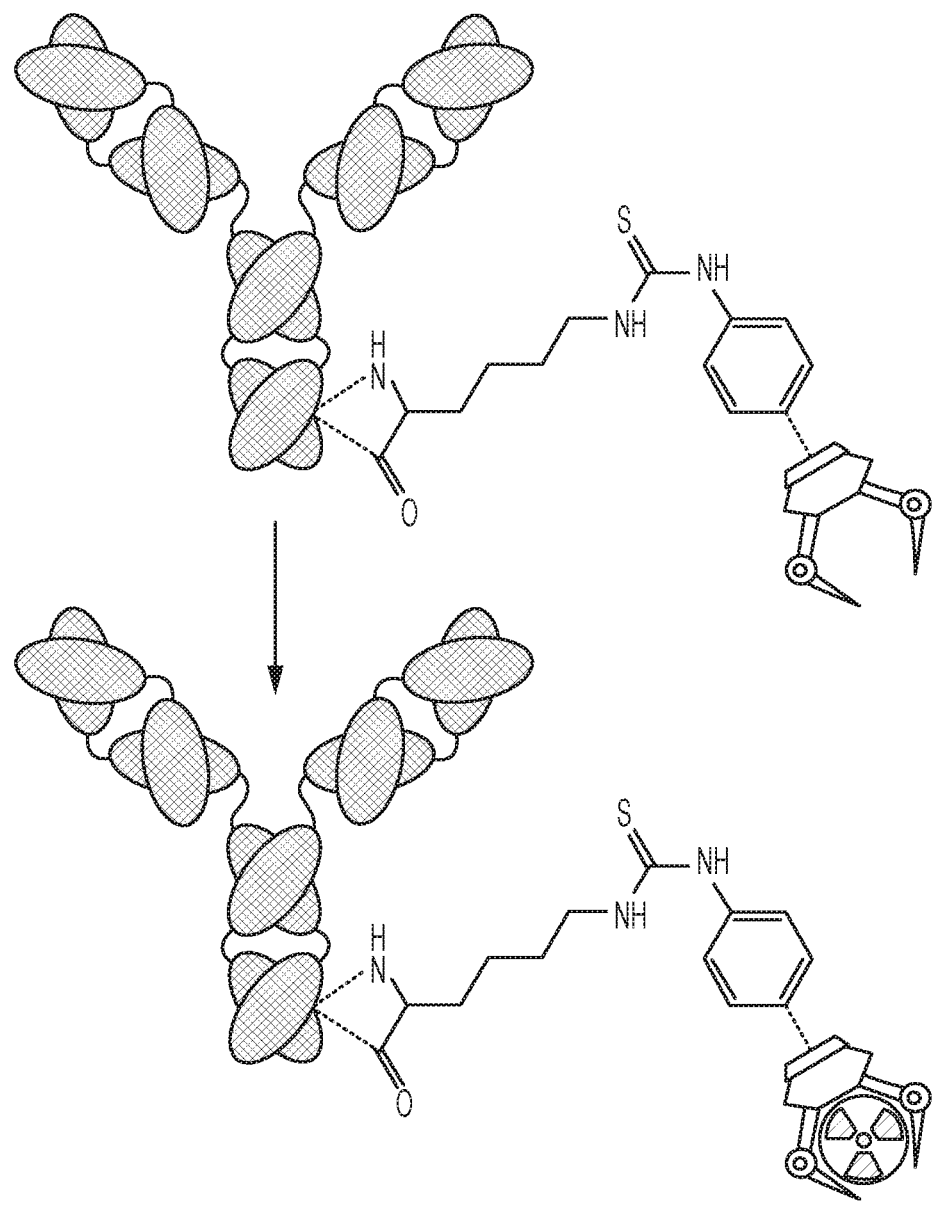
FIG. 37 shows a schematic of ligand-antibody labeling. Both p-SCN-Bn-DFO-Trastuzumab and p-SCN-Bn-HOPO-Trastuzumab were reacted with $^{89}$Zr radiolabeling reaction. Similar conditions as bare ligands, room temperature and pH 7, 1-3 h. Typical specific activity achieved is ~2 mCi/mg.

The conjugation of p-SCN-Bn-DFO to an antibody is typically carried out at pH 9 at 37° C. in 1 h, and the final product is purified through size exclusion chromatography using pre-packed PD-10 desalting columns (GE Healthcare). FIG. 37 shows a schematic of ligand-antibody labeling. Both p-SCN-Bn-DFO-Trastuzumab and p-SCN-Bn-HOPO-Trastuzumab were reacted with $^{89}$Zr radiolabeling reaction. Similar conditions were used as the bare ligands (e.g., room temperature and pH 7, 1-3 h). Typical specific activity achieved is ~2 mCi/mg. In certain embodiments, ligands with benzyl isothiocyanate functionalities use the exact same conditions for conjugation. The reaction of an NHS ester containing ligand should be similar to that of the isothiocyanate, with some variation such as incubations at RT with a longer reaction time. $^{89}$Zr is produced on a cyclotron through a (p,n) reaction on a 100% naturally abundant $^{89}$Y thin foil target using a 15 MeV proton beam with a 100 angle of incidence to the target. The $^{89}$Zr is then purified on a column of hydroxamate resin and eluted with 1 M oxalic acid, thus yielding $^{89}$Zr-oxalate as the starting material for radiolabeling. This $^{89}$Zr-oxalate solution can be neutralized to pH 7 and used to radiolabel the ligand-antibody complexes.

The time and temperature of the radiolabeling reaction can be evaluated for each ligand-antibody complex. The reactions can be monitored using radio-ITLC with salicylic acid impregnated instant thin-layer chromatography paper (ITLC-SA, Agilent Technologies) and 50 mM EDTA at pH 5.5 as the elutant.

The suitability of the bifunctional ligands can be evaluated by their ability to be (1) conjugated to an antibody, (2) whether they achieve a radiochemical yield (e.g., greater than 95%) and specific activity (e.g., greater than or equal to 2 mCi/mg) when radiolabeled, and (3) the stability of the radiolabeled complex. The stoichiometry of the conjugation of the ligand to the antibody can be evaluated using standard radiometric isotopic dilution as well as mass spectrometry studies. Furthermore, in vitro immunoreactivity assays can be carried out on the $^{89}$Zr-ligand-antibody complexes to ensure that the conjugation does not affect the ability of the antibody to bind its target. Radiolabeling can be carried out within an hour at room temperature. Radiochemical yield can be measured by radio-ITLC on the crude reaction mixture while specific activity can be calculated after purification of the final complex. The stability of the $^{89}$Zr-ligand-antibody complexes can be evaluated in both phosphate buffered saline (PBS) and human serum at 37° C. over a period of 7 days. All parameters can be measured and compared to those of $^{89}$Zr-DFO-antibody complexes as a standard.

Serum stability and immunoreactivity of $^{89}$Zr-complexes were evaluated. To determine the stability in serum, $^{89}$Zr-complexes were incubated in human serum at 37° C. for 7 d. The percentage of intact species was monitored by ITLC (Table 9).

TABLE 9

| Complex | Ligand Only | Ligand-mAb |
| --- | --- | --- |
| p-SCN-Bn-DFO | 97.7 ± 0.2% | 94.7 ± 0.7% |
| p-SCN-Bn-HOPO | 97.5 ± 0.5% | 89.2 ± 0.9% |

To calculate the immunoreactivity, $^{89}$Zr-complexes were incubated with BT474 cells for 1 h (Table 10).

TABLE 10

| Complex | Immunoreactive Fraction |
| --- | --- |
| $^{89}$Zr-DFO-Trastuzumab | 88.6 ± 2.1% |
| $^{89}$Zr-HOPO-Trastuzumab | 92.4 ± 6.8% |

$^{89}$Zr-ligand-mAb complexes can be characterized with radio-ITLC, HPLC, and size exclusion chromatography as well as checked for stability and immunoreactivity. Radio-ITLC analysis can be measured on a Bioscan AR-2000 radio-ITLC plate reader using Winscan Radio-TLC software (Bioscan Inc., Washington, D.C.). All stability tests can be carried out in triplicate.

The pharmacokinetics of the $^{89}$Zr-ligand-antibody complexes can be evaluated with PET imaging, acute biodistribution studies, and autoradiography in xenograft tumor-bearing mice. The number of mice required for the imaging and biodistribution experiences encompassed can be based on the ultimate number of bifunctionalized ligands that are developed and shown to effectively radiolabel as ligand-antibody conjugates. In certain embodiments, tests can be carried out as described in Table 11. In this embodiment, 16 total new bifunctional chelators can be developed and then the most promising quarter can be taken through to in vivo evaluation. These four $^{89}$Zr-ligand-trastuzumab complexes can then undergo imaging and biodistribution studies in tumor bearing mice. A group of mice, n=5, can be tested for a time point for biodistribution for each radiotracer with an additional group for imaging. Additionally, a full set of mice can be used for comparative imaging and biodistribution with $^{89}$Zr-DFO-trastuzumab.

Table 11 shows that each group can be imaged with $^{89}$Zr-trastuzumab with varying bifunctional ligands and 150 total mice can be used. Bilateral BT-474 (HER2/neu positive) and MDA-MB-468 (HER2/neu negative positive) can be used for this study.

TABLE 11

| Radiotracer (total animal #) | # mice per Group | Time points |
| --- | --- | --- |
| $^{89}$Zr-BH1-trastuzumab (30) | 5 | 6, 24, 72, 120, 168 h |
| $^{89}$Zr-BH2-trastuzumab (30) | 5 | 6, 24, 72, 120, 168 h |
| $^{89}$Zr-BH3-trastuzumab (30) | 5 | 6, 24, 72, 120, 168 h |
| $^{89}$Zr-BH4-trastuzumab (30) | 5 | 6, 24, 72, 120, 168 h |
| $^{89}$Zr-DFO-trastuzumab (30) | 5 | 6, 24, 72, 120, 168 h |

As trastuzumab can be used as the basis for the $^{89}$Zr-ligand-antibody complexes, immunoPET and biodistribution experiments can be conducted using female, athymic nu/nu mice bearing sub-cutaneous BT-474 (HER2/neu positive) and/or MDA-MB-468 (HER2/neu negative) tumor xenografts.

$^{177}$Lu-HOPO, $^{177}$Lu-DOTA, were evaluated in healthy nude female mice (8-10 weeks old, Charles River Laboratory). In certain embodiments, the mice (4 per group) were injected with approximately 50 µCi each ($^{177}$Lu) and dissected at 0.5, 1, 4, 24, and 144 h. Aliquots of the injectate (10 µL) were weighed and counted as standards with the tissues. The injection syringes were weighed pre- and post-injection to determine the weight of injectate and the activity according to the dose calibrator was measured before and after injection. All of the tissues were weighed and counted with the standards. The standards were used to obtain the counts/g injectate, the weights of the injectate were used to determine the total number of counts for the injected dose (ID), the counts of the tissue were used to get the % ID, and the weights of the tissues were used to obtain the % ID/g. Standard averaging and standard deviation calculations were applied.

$^{177}$Lu-HOPO-trastuzumab was evaluated in healthy nude female mice (11-13 weeks old, CRL) and in SKOV3 tumor-bearing nude female mice (shoulder xenografted with 5×10$^6$ cells in 1:1 matrigel:media approximately 3 weeks prior to being used in the study). In certain embodiments, the healthy mice (n=4) were injected with 50 µCi/mouse and sacrificed at 1, 3, 7, 10, 14, and 21 d after radioactive injection. Four of the tumor-bearing mice were injected with 500 µCi/mouse, imaged using the nanoSPECT/CT (Mediso, Budapest, Hungary) at 1, 3, and 7 d p.i, and dissected at 7 d p.i. To obtain the SPECT/CT images, the imaging mice were anesthetized using 4-3% isofluorane with 2 L/min oxygen flow, approximately a 7.5 min CT scan was obtained followed by a 1 h SPECT image acquisition using the same imaging window as the CT scan. The other eight mice (n=4) were injected with 50 µCi/mouse and dissected at 1 and 3 d p.i. Similar data collection and analysis was applied to this group as was described for the healthy mice injected with chelator complexes.

Biodistribution Studies

Following i.v. tail vein injection of 15-20 µCi of the $^{89}$Zr-radiolabeled compounds, the animals (n=5 per group) can be sacrificed at selected time points after injection and desired tissues can be removed, weighed, and counted for radioactivity accumulation. Tissues including blood, lung, liver, spleen, kidney, muscle, heart, bone, and tumor can be counted. The percentage injected dose per gram (% ID/g) and percentage injected dose per organ (% ID/organ) can be calculated by comparison to a weighed, counted standard solution. Time points can be 1, 12, 24, 96, and 168 h.

Pharmacokinetic Measurements

The acute biodistribution and PET data described above can provide the temporal concentration of the agents and allow for characterization of pharmacokinetic parameters of the agents in tissues. From this data, the standard pharmacokinetic measures of clearance, absorption, and volume of distribution of each organ can be calculated.

Data Analysis and Statistics

Radiolabeling of ligand-antibody complexes can be evaluated with radio-ITLC and purified by SEC and/or centrifugal filtration. Statistically significant differences between mean values can be determined using analysis of variances (ANOVA) coupled to Scheffe's test or, for statistical classification, a Student's t test can be performed using PRISM (San Diego, Calif.). Differences at the 95% confidence level (p<0.05) can be considered significant. In certain embodiments, at least one bifunctional chelator based on each of the conjugation chemistries can be evaluated in vivo. As described herein, the eight oxygen donor atoms fully coordinate to $^{89}$Zr. Moreover, the linear ligand exhibit fast $^{89}$Zr labeling kinetics at room temperature and physiological pH. Thus, the properties of HOPO stabilize $^{89}$Zr. To further these $^{89}$Zr binding properties, a bifunctional ligand with improved $^{89}$Zr binding properties and improved linker technology was created to eliminate the release of $^{89}$Zr and uptake of the radioisotope in bone and non-target organs during PET imaging. Reagents All chemicals, unless otherwise noted, were acquired from Sigma-Aldrich (St. Louis, Mo.) and used as received without further purification. All instruments were calibrated and maintained in accordance with standard quality-control procedures. High-resolution mass spectrometry was carried out through electrospray ionization using an Agilent 6520 QTOF instrument. $^1$H and $^{13}$C NMR spectra were recorded at varying temperatures on a Bruker Avance III spectrometer equipped with a triple resonance inverse cryoprobe, with $^1$H and $^{13}$C resonance frequencies of 600.13 MHz and 150 mHz or a Bruker DRX spectrometer equipped with a $^1$H, $^{13}$C cryoprobe, with respective resonance frequencies of 500.13 MHz and 125.76 MHz with Topsin software. The NMR spectra are expressed on the δ scale and were referenced to residual solvent peaks and/or internal tetramethylsilane. The HPLC system used for analysis and purification compounds consisted of a Rainin HPXL system with a Varian ProStar 325 UV-Vis Detector monitored at 254 nm. Analytical chromatography was carried out using a Waters Symmetry C18 Column, 100 Å, 5 µm, 4.6 mm×100 mm at a flow rate of 1.0 mL/min and purification was done with a preparatory Waters Symmetry C18 Prep Column, 100 Å, 5 µm, 19 mm×100 mm at a flow rate of 17.059 mL/min. IR spectroscopy was performed on a solid sample using an attenuated total reflectance attachment on a PerkinElmer Spectrum 2 FT-IR spectrometer with a UATR Two attachment.

$^{89}$Zr was produced at Memorial Sloan Kettering Cancer Center on a TR19/9 cyclotron (Ebco Industries Inc.) via the $^{89}$Y(p,n)$^{89}$Zr reaction and purified to yield $^{89}$Zr with a specific activity of 196-496 MBq/mg. Activity measurements were made using a CRC-15R Dose Calibrator (Capintec). For the quantification of activities, experimental samples were counted on an Automatic Wizard (2) g-Counter (Perkin Elmer). The radiolabeling of ligands was monitored using salicylic acid impregnated instant thin-layer chromatography paper (ITLC-SA) (Agilent Technologies) and analyzed on a Bioscan AR-2000 radio-TLC plate reader using Winscan Radio-TLC software (Bioscan Inc., Washington, D.C.). All in vivo experiments were performed according to protocols approved by the Memorial Sloan Kettering Institutional Animal Care and Use Committee (protocol 08-07-013). Purity of greater than 95% was confirmed using quantitative HPLC analysis for non-radioactive compounds (HOPO and Zr-HOPO) and radio-TLC for radioactive compounds ($^{89}$Zr-HOPO).

Synthesis of (N1, N4, N9-Tri-tert-butoxycarbonyl)-1,12-di-amino-4,9-diazadodecane (4 in FIG. 4)

The tri-BOC-protected spermine was prepared according to Geall et al. "Synthesis of Cholesteryl Polyamine Carbamate: pKa Studies and Condensation of Calf Thymus DNA. Bioconjugate Chem. 2000; 11:314-326." To a flask containing spermine (1 from FIG. 4) (2.02 g, 10 mmol) in 150 ml methanol at −78° C. under argon was added dropwise ethyl trifluoroacetate (1.42 g, 10 mmol) in 100 mL of methanol over 30 min while stirring. Stirring was continued for another 30 min and the reaction mixture was allowed to come to 0° C. An excess of di-tert-butyl dicarbonate (60 mmol) in 100 mL methanol was added over a period of 1 h. The reaction mixture was stirred at room temperature for 18 h. Concentrated ammonium hydroxide solution was added to the reaction mixture until the pH reached 11 and the reaction was stirred for another 15 h at room temperature. The methanol was evaporated under reduced pressure and the resulting liquid was dissolved in methylene chloride, washed with water, dried over anhydrous sodium sulfate, and evaporated to dryness. The crude compound was purified by column chromatography silica using $CH_2Cl_2$:MeOH: conc $NH_3$ 70:10:1 to 50:10:1 (v/v/v) yielding the desired product 4 (yield 28%). Products 2 and 3 (from FIG. 4) were used directly and not isolated.

$^1$H-NMR (CDCl3, 400 MHz): δ 3.07-3.21 (m, 10H), 2.68 (t, 2H), 2.08 (bs, 2H), 1.59-1.70 (m, 4H), 1.41-1.46 (m, 31H). $^{13}$C-NMR (CDCl3, 100 MHz): δ 156.04, 155.55, 79.48, 78.88, 46.80, 43.79, 38.76, 37.35, 32.46, 30.9, 28.42. HRMS calculated for $C_{25}H_{50}N_4O_6$ ([M+H]$^+$), 503.38, found 503.3817.

Synthesis of tert-butyl(4-((tert-butoxycarbonyl)(3-((4-nitrophenethyl)amino)propyl)amino)butyl)(3-((tert-butoxycarbonyl)amino)propyl)carbamate (5 from FIG. 4)

A solution of 4-nitrophenylethyl bromide (0.126 g, 0.55 mmol) in DMF (2 mL) was added to a suspension of 4 (from FIG. 4) (0.201 g, 0.5 mmol) and $K_2CO_3$ (0.138 g, 1 mmol) in DMF (5 mL) under $N_2$. The resulting reaction mixture was stirred at 60° C. for 12 h. Solvent was removed under vacuum and the resulting residue was dissolved in methylene chloride, washed with water, dried over anhydrous sodium sulfate, and evaporated to dryness. The crude compound was purified by column chromatography silica using 1% methanol in methylene chloride to give compound 5 (from FIG. 4) as a gummy solid. (Yield=30%). $^1$H NMR (500 MHz, CDCl3): (mixture of rotamers) δ 8.10-8.09 (d, 2H), 7.36 (d, 2H), 3.28-2.58 (m, 20H), 1.80 (bs, 2H), 1.58 (bs, 2H), 1.38-1.36 (m, 27H). $^{13}$C NMR (500 MHz, CDCl3): (mixture of rotamers) δ 156.1, 155.9, 129.8, 123.9, 79.3, 78.7, 78.3, 49.85, 49.83, 49.80, 49.76, 49.72, 47.1, 47.0, 46.94, 46.91, 46.89, 46.86, 46.77, 46.72, 46.67, 46.60, 46.52, 46.46, 46.41, 46.38, 46.33, 46.27, 46.26, 46.23, 46.20, 45.69, 45.66, 44.28, 44.20, 43.88, 43.83, 43.78, 43.52, 43.47, 43.40, 43.38, 43.32, 37.76, 37.68, 37.64, 37.60, 37.56, 37.51, 37.48, 37.38, 34.45, 34.40, 34.15, 28.45; HRMS calculated for $C_{33}H_{57}N_5O_8$ ([M+H]$^+$), 651.4207, found 652.4387.

Synthesis of N1-(3-aminopropyl)-N4-(3-((4-nitrophenethyl)amino)propyl)butane-1,4-diamine (6 from FIG. 4)

A solution of 4M HCl in dioxane (5 mL) was added to a stirring solution of 5 (from FIG. 4) (0.17 g, 0.5 mmol) in $CH_2Cl_2$ (10 mL), under nitrogen, at 25° C. After 2 h, the solution was concentrated in vacuo and co-distilled with toluene (3×5 mL) (poly-HCl salt). This compound was not isolated, but rather used directly in the next step.

Synthesis of 1-(benzyloxy)-N-(3-(1-(benzyloxy)-6-oxo-1,6-dihydropyridine-2-carboxamido)propyl)-N-(4-(1-(benzyloxy)-N-(3-(1-(benzyloxy)-N-(4-nitrophenethyl)-2-oxo-1,2-dihydropyridine-3-carboxamido)propyl)-2-oxo-1,2-dihydropyridine-3-carboxamido)butyl)-6-oxo-1,6-dihydropyridine-2-carboxamide (7 from FIG. 4)

A solution of 1-(benzyloxy)-6-oxo-1,6-dihydropyridine-2-carbonyl chloride (0.789 g, 3 mmol) in methylene chloride (15 mL) was added drop wise to a stirred solution of triethylamine (0.835 mL, 6 mmol), 6 (from FIG. 4) (0.351 g, 1 mmol) and DMAP (0.006 g, 0.05 mmol) in dry methylene chloride (10 mL) at 0° C. The reaction mixture was warmed to room temperature and stirred for 24 h. The reaction mixture was washed with 10% $NaHCO_3$ solution, followed by water. The organic phase was dried over anhydrous $Na_2SO_4$ and was then removed with a rotary evaporator. The crude product was purified through column chromatography over silica gel using 2-4% methanol in dichloromethane eluent producing in 5 (from FIG. 4) as brown foam (yield 56%).

(16H), 3.82-2.06 (m, 25H), 1.84-0.63 (m, 8H); $^{13}$C NMR (600 MHz, CDCl3): (mixture of rotamers) δ 1420.16, 142.14, 139.12, 139.05, 139.0, 138.97, 138.87, 138.82, 138.78, 138.70, 138.66, 138.59, 138.55, 138.50, 133.16, 133.13, 133.06, 130.86, 130.80, 130.72, 130.66, 130.45, 135.41, 135.37, 130.34, 130.32, 130.29, 130.26, 130.23, 129.79, 129.76, 129.73, 129.70, 129.65, 129.62, 129.56, 123.97, 123.92, 123.83, 123.76, 123.74, 123.36, 122.79, 122.65, 122.57, 122.53, 122.52, 122.48, 104.07, 103.62, 103.54, 103.49, 103.40, 103.34, 79.66, 46.97, 46.08, 46.02, 41.99, 40.64, 36.95, 36.93, 36.89, 36.81, 34.61, 33.39, 33.23, 33.11, 26.09, 26.88, 25.52, 25.49, 25.32, 25.18, 25.11, 24.84, 24.80, 24.53, 24.17, 24.13, 23.98; HRMS calculated for $C_{70}H_{69}N_9O_{14}$ ([M+H]$^+$), 1260.5042, found 1260.5038.

Synthesis of N-(4-(N-(3-(N-(4-aminophenethyl)-1-(benzyloxy)-2-oxo-1,2-dihydropyridine-3-carboxamido)propyl)-1-(benzyloxy)-2-oxo-1,2-dihydropyridine-3-carboxamido)butyl)-1-(benzyloxy)-N-(3-(1-(benzyloxy)-6-oxo-1,6-dihydropyridine-2-carboxamido)propyl)-6-oxo-1,6-dihydropyridine-2-carboxamide (8 from FIG. 4)

To a suspension of Raney nickel in (1:1) MeOH: THF (10 mL), 7 (from FIG. 4) (0.2 g, 0.157 mmol) was added and hydrogenated at balloon $H_2$ pressure at room temperature for 3 h. The catalyst was filtered through a celite pad under inert atmosphere. The filtrate was evaporated under reduced pressure to obtain the crude amine. This crude product was used directly in the next step without further workup. For characterization purposes, some of this product was HPLC purified as a cream colored solid.

$^1$H NMR (600 MHz, DMSO-d6): (mixture of rotamers) δ 8.70-8.64 (m, 1H), 7.44-7.33 (m, 27H), 6.93-6.89 (m, 1H), 6.89-6.80 (m, 3H), 6.64-6.62 (m, 4H), 6.31-6.10 (m, 4H), 5.38-5.26 (m, 5H), 5.04-4.99 (m, 3H), 3.60-3.55 (m, 18H), 3.16-3.13 (m, 14H), 1.76-1.21 (m, 10H); 158.18, 158.14, 155.63, 155.30, 155.27, 155.09, 155.06, 155.03, 141.89, 141.63, 141.60, 140.70, 140.59, 140.51, 136.82, 136.77, 136.64, 131.65, 161.41, 131.38, 131.35, 127.49, 127.44, 127.38, 127.29, 126.97, 126.87, 126.27, 126.23, 126.20, 120.31, 120.35, 119.75, 117.81, 115.46, 113.1, 101.62, 100.26, 100.1, 76.16, 76.10, 59.81, 52.71, 45.56, 45.49, 43.71, 43.47, 43.31, 41.3, 39.83, 39.65, 34.51, 34.45, 34.18, 34.11, 31.09, 29.71, 25.62, 24.36, 23.29, 22.73, 22.54, 22.43, 21.75, 21.38, 21.29; HRMS calculated for $C_{70}H_{72}N_9O_{12}$ ([M+H]$^+$), 1230.5300, found 1230.5299.

Synthesis of 4-(11,15-bis(1-hydroxy-2-oxo-1,2-dihydropyridine-3-carbonyl)-1-(1-hydroxy-6-oxo-1,6-dihydropyridin-2-yl)-6-(1-hydroxy-6-oxo-1,6-dihydropyridine-2-carbonyl)-1-oxo-2,6,11,15-tetraazaheptadecan-17-yl)benzenaminium Chloride (9 from FIG. 4)

Crude 8 (from FIG. 4) was dissolved in a 1:1 mixture of acetic acid and concentrated HCl (6 mL) at room temperature and heated to 45-50° C. for 18 h. The reaction progress was monitored by LC-MS. T. The crude product was dried and re-dissolved in water/acetonitrile and purified by HPLC on a preparative C18 column (Waters Symmetry C18 Prep Column, 100 Å, 5 µm, 19 mm×100 mm) at 17.059 mL/min using a gradient of 10-23% MeCN in water (both containing 0.1% TFA) with an initial hold at 10% MeCN for 1.33 mins and then a ramp to 23% MeCN over 20 minutes. The product peak was collected from 6.45-8.26 min and the eluted solution was lyophilized to recover the product as an off white solid. The purified ligand was collected in multiple small batches with an approximate combined yield of 70%.

The purified sample was confirmed by HPLC on an analytical C18 column (Waters Symmetry C18 Prep Column, 100 Å, 5 µm, 4.6 mm×100 mm) at 1 mL/min using a gradient of 10-30% MeCN in water (both containing 0.1% TFA) with an initial hold at 10% MeCN for 1.33 mins and then a ramp to 30% MeCN over 30 minutes followed by a ramp to 95% MeCN over 1 minute and an isocratic hold at 95% MeCN for 5.66 minutes. $^1$H NMR: J1, J2=6 Hz, 1H), 7.08-7.01 (m, 2H), 6.54-6.53 (m, 4H), 6.33-6.32 (m, 3H), 6.18-6.21 (m, 0.5H), 5.74-5.67 (m, 0.5H), 3.65-3.51 (m, 4H), 3.51-3.16 (m, 8H), 3.12-2.70 (m, 11H), 1.91-1.38 (m, 10H); $^{13}$C NMR (500 MHz, CDCl$_3$): (mixture of rotamers) δ 158.8, 158.6, 158.4, 158.1, 157.9, 157.8, 157.77, 157.73, 142.5, 142.49, 142.45, 142.41, 142.32, 142.24, 142.04, 138.10, 138.0, 137.59, 137.51, 130.36, 130.31, 130.18, 130.08, 119.76, 119.45, 117.5, 115.6, 104.3, 102.5, 102.47, 102.41, 50.01, 48.12, 47.9, 46.0, 46.0, 43.7, 42.3, 37.2, 37.0, 36.97, 33.80, 32.65, 32.49, 28.16, 26.90, 26.23, 25.4, 25.4, 25.2, 25.1, 24.4, 24.3, 24.3, 24.2; HRMS calculated for $C_{42}H_{47}N_9O_{12}$ ([M+H]+), 870.3422, found 870.3420.

Synthesis of 1-hydroxy-N-(3-(1-hydroxy-6-oxo-1,6-dihydropyridine-2-carboxamido)propyl)-N-(4-(1-hydroxy-N-(3-(1-hydroxy-N-(4-isothiocyanatophenethyl)-2-oxo-1,2-dihydropyridine-3-carboxamido)propyl)-2-oxo-1,2-dihydropyridine-3-carboxamido)butyl)-6-oxo-1,6-dihydropyridine-2-carboxamide (p-SCN-Bn-HOPO from FIG. 4)

$NEt_3$ (0.0012 g, 0.012 mmol) was added to a solution of 9 from FIG. 4 (0.01 g, 0.011 mmol) in (8:2) acetonitrile and water (1 mL). Next, Di-2-Pyridyl thionocarbonate (0.011 g, 0.05 mmol) was added at room temperature and stirred vigorously for 1 h. The crude reaction solution was directly purified by HPLC on a preparative C18 column (Waters Symmetry C18 Prep Column, 100 Å, 5 µm, 19 mm×100 mm) using a gradient of 5-75% MeCN in water (both containing 0.1% TFA) with an initial hold at 5% MeCN for 1.33 mins and then a ramp to 75% MeCN over 30 minutes. The product peak was collected from 15.01-15.5 min and the eluted solution was lyophilized to recover the product as a white solid. The purified ligand was collected in multiple small batches with an approximate combined yield of 32%.

The purified sample was confirmed by HPLC on an analytical C18 column (Waters Symmetry C18 Prep Column, 100 Å, 5 µm, 4.6 mm×100 mm) at 1 mL/min using a gradient of 5-75% MeCN in water (both containing 0.1% TFA) with an initial hold at 5% MeCN for 1.33 mins and then a ramp to 75% MeCN over 30 minutes followed by a ramp to 95% MeCN over 1 minute and an isocratic hold at 95% MeCN for 5.66 minutes.

$^1$H NMR (500 MHz, CDCl$_3$): (mixture of rotamers) δ 7.37-7.31 (m, 7H), 7.12-7.08 (m, 1H), 6.58-6.52 (m, 4H), 6.34-5.81 (m, 4H), 3.62-3.54 (m, 12H), 3.13-2.83 (m, 11H), 2.01-1.24 (m, 11H); 13C NMR (500 MHz, CDCl3): (mixture of rotamers) δ 161.78, 161.71, 161.54, 161.4, 160.65, 160.61, 157.89, 157.83, 157.78, 157.73, 142.59, 142.48, 142.41, 142.33, 142.31, 142.21, 139.58, 138.49, 138.90, 138.81, 138.17, 138.0, 137.57, 137.50, 134.07, 130.76, 130.74, 130.59, 130.52, 128.89, 128.66, 126.41, 126.32, 119.74, 119.53, 119.43, 104.33, 102.50, 102.39, 49.62, 48.11, 47.96, 46.49, 46.01, 45.70, 37.24, 37.01, 36.96, 34.04, 32.83, 32.71, 28.15, 27.12, 26.85, 26.22, 25.46, 25.26, 25.17, 24.36, 24.18; HRMS calculated for $C_{43}H_{45}N_9O_{12}S$ ([M+H]$^+$), 912.2987, found 912.2987.

Preparation of $^{177}$Lu-HOPO and $^{177}$Lu-DOTA

A 0.05 M HCl solution of $^{177}$Lu was obtained from PerkinElmer (Waltham, Mass.) with greater than 20 Ci/mg. Approximately 2200 Ci (81.4 MBq) of $^{177}$Lu was diluted in 33 µL of 0.2 M NH$_4$OAc (pH 5.5). To this, 25 µL of DMSO was added and split into two reaction vials (25 µL each). HOPO ligand dissolved in DMSO (2.00 mM, 11.4 µL, 22.8 nmol) was added to one reaction vial and DOTA ligand dissolved in DMSO (2.86 mM, 8.02 µL, 22.9 nmol) was added to the other reaction vial. The reactions were reacted without stirring at RT for 10 min, then diluted with 0.9 mL of PBS. The reaction mixture was HPLC or radioTLC analyzed for purity. The specific activity was approximately 53.0 µCi/nmol (1.96 GBq/µmol). Prior to murine tail vein injection, the solution was filtered through a 0.2 µm sterile filter (13 mm diameter, Whatman, GE Healthcare Life Sciences, Buckinghamshire, UK).

Ligand-Antibody Conjugation

Trastuzumab (purchased commercially as Herceptin, Genentech, San Francisco, Calif.) was purified using pre-packed size exclusion chromatography (SEC) columns (Sephadex G-25 M, PD-10 Desalting Columns, 50 kDa, GE Healthcare) and centrifugal filter units with a 50,000 molecular weight cutoff (Amicon Ultra 4 Centrifugal Filtration Units, Millipore Corp., Billerica, Mass.) and phosphate buffered saline (PBS, pH 7.4) to remove α_α-trehalose dihydrate, L-histidine, and polysorbate 20 additives. After purification, the antibody was taken up in PBS at pH 7.4. Subsequently, ~60 µL of antibody solution (~13 nmol) were diluted to 1 mL with PBS at pH 7.4. The pH antibody solution was raised to 8.8-9.0 with 0.1 M Na$_2$CO$_3$ before the slow addition of 5 equivalents of p-SCN-Bn-HOPO or p-SCN-Bn-HOPO in ~12 µL of DMSO. The reaction was incubated at 37° C. for 1 h and shaken at 300 rpm, followed by SEC and centrifugal filtration to purify the ligand-antibody conjugate. The final bioconjugates were stored in PBS pH 7.4 at 4° C. Chelate number was investigated via MALDI-TOF mass spectrometry analysis conducted at the University of Alberta. Samples of DFO-trastuzumab, HOPO-trastuzumab, and unmodified trastuzumab were submitted for analysis and the chelate number was calculated as the difference between the modified and unmodified antibody divided by the mass of the chelator. Samples were analyzed in triplicate and values were calculated from averages. When the triplicate MALD-TOF results were examined, the error was determined to be too large to provide meaningful results. Identical samples gave values that differed by the masses of entire chelates. Chelate number was then determined using an isotopic dilution assay.

The preparation of $^{177}$Lu-HOPO-trastuzumab was similar to that of $^{177}$Lu-HOPO, 300 µCi of the $^{177}$Lu was diluted in 200 µL of 0.2 M NH$_4$OAc (pH 5.5) which contained 6 mg/mL ascorbic acid. The HOPO-trastuzumab (7.24 mg/mL, 6.91 µL) was added to the solution and reacted for 10 min at room temperature without stirring. An aliquot of 50 mM DTPA (50 µL) was added to quench the reaction and chelate any residual or loosely bound $^{177}$Lu. The product mixture was purified by gravity gel size exclusion chromatography (PD 10 column, GE Healthcare) and eluted in PBS with 6 mg/mL ascorbic acid. The eluant was analyzed by radioTLC with ITLC plates and developing in 50 mM DTPA solution. The resulting solution was approximately 4-5 mCi/mg (0.15-0.19 GBq/mg).

Radiolabeling Experiments $^{89}$Zr was received after target processing as $^{89}$Zr-oxalate in 1.0 M oxalic acid. This solution is then neutralized with 1.0 M sodium carbonate to reach pH 6.8-7.2. Both the DFO and HOPO ligands were labeled at various concentrations in water or saline with the neutralized $^{89}$Zr solution at room temperature for varying lengths of time, typically 10-60 min. Reactions were monitored via radio-TLC with different stationary phases depending on the nature of the reaction. $^{89}$Zr-ligand complexes required Varian ITLC-SA strips (Agilent Technologies) whereas $^{89}$Zr-ligand-trastuzumab complexes employed Varian ITLC-SG strips (Agilent Technologies), but both analysis methods used 50 mM EDTA at pH 5 as the mobile phase. $^{89}$Zr complexes remained at the origin, while free $^{89}$Zr was taken up by EDTA in the mobile phase and migrated along the ITLC strip.

Serum Stability Studies $^{89}$Zr-ligand and $^{89}$Zr-ligand-antibody complexes were prepared according to the radiolabeling protocol as described above. For each $^{89}$Zr complex, samples were made consisting of 900 µL human serum and 100 µL of the $^{89}$Zr species and were placed in a heat block at 37° C. with agitation. Samples were monitored using radio-TLC before being added to the serum and then after 1 week of incubation. The stability of the complexes was measured as the percentage of $^{89}$Zr that was retained at the origin of the ITLC strip and therefore still intact.

The following procedure was used for the serum stability studies for the $^{177}$Lu based systems. In triplicate, 50 µL of the diluted $^{177}$Lu-HOPO or $^{177}$Lu-DOTA species was added to 450 µL of human serum (Sigma-Aldrich, St. Louis, Mo.) and incubated at 37° C. on a thermomixer (Eppendorf, Hauppauge, N.Y.). At various time points (0, 1, 3, and 6 d), an aliquot of each was spotted on two ITLC plates, one developed in 50 mM DTPA and one in EtOH (for Lu-DOTA) or 50:50 EtOH in water (for Lu-HOPO). After 6 days, the $^{177}$Lu-DOTA incubated with serum was also diluted with 500 µL of EtOH, vortexed, centrifuged (twice at 12,000 rpm for 5 min each time) at room temperature. The supernatant was filtered through a 0.2 m nylon filter (13 mm, Whatman), centrifuged the filtrate for 5 min at 12,000 rpm at room temperature, and injected the supernatant onto the HPLC.

Similarly, 100 µL of the $^{177}$Lu-HOPO-trastuzumab solution was incubated with 900 µL of human serum (in quadruplicate). At various time points (1, 3, and 6 d), a 100 µL aliquot of the incubation material was added to 10 µL of 50 mM DTPA, vortexed, and spotted onto an ITLC strip. Additionally, a 100 µL aliquot of the starting solution (just PBS with 6 mg/mL ascorbic acid) was added to 10 µL of DTPA, vortexed, spotted onto an ITLC strip. The ITLC strips were developed in 50 mM DTPA and analyzed by radioTLC.

Immunoreactivity Assay

The immunoreactivity of the $^{89}$Zr-DFO-trastuzumab and $^{89}$Zr-HOPO-trastuzumab bioconjugates was determined using specific radioactive cellular-binding assays. To this end, BT474 cells were suspended in microcentrifuge tubes at concentrations of 2.5, 2.0, 1.5, 1.25, 1.0, 0.75, and 0.25×106 cells/mL in 500 µL PBS (pH 7.4). Aliquots of either $^{89}$Zr-DFO-trastuzumab or $^{89}$Zr-HOPO-trastuzumab (50 µL of a stock solution of ~10 µCi in 10 mL of 1% bovine serum albumin in PBS pH 7.4) were added to each tube (n=3; final volume: 550 µL), and the samples were incubated on a mixer for 60 min at room temperature. The treated cells were then pelleted via centrifugation (600 G for 2 min), aspirated, and washed twice with cold PBS before removing the supernatant and counting the activity associated with the cell pellet. The activity data were background-corrected and compared with the total number of counts in appropriate control samples. Immunoreactive fractions were determined by linear regression analysis of a plot of (total/bound) activity against (1/[normalized cell concentration]). No weighting was applied to the data, and data were obtained as n=3.

The immunoreactivity of the $^{177}$Lu based systems was tested using the following procedure. SKOV3 cells ($10×10^6$ cells/0.2 mL cell media) were added to microcentrifuge tubes (four replicates had 0.2 mL/tube and four had 0.1 mL/tube). To each of the 0.2 mL cell suspensions, 20 µL of the $^{177}$Lu-HOPO-trastuzumab (20 nCi, 740 Bq, 3.7 ng, in PBS pH 7.4 with 6 mg/mL ascorbic acid) was added and gently vortexed. To each of the 0.1 mL cell suspensions, L of the $^{177}$Lu-HOPO-trastuzumab (10 nCi, 370 Bq, 1.9 ng, in PBS pH 7.4 with 6 mg/mL ascorbic acid) was added and gently vortexed. Four samples (0.22 mL suspension) were incubated at 4° C. for 60 min (without shaking in an ice bath) and four samples (0.11 mL suspensions) were incubated at 37° C. for 60 min (with shaking at 300 rpm in a thermomixer). After incubation, the samples were centrifuged (600 g, 4° C., 2 min), supernatant removed, and washed three times with ice-cold PBS (1 mL). In each of the washes, the cell pellet was broken-up with gentle vortexing, the samples were centrifuged (600 g, 4° C., 2 min), and the supernatant removed. The supernatants at each step were collected separately and the cell-bound material was measured for the final pellets in the original incubation microcentrifuge tubes. All of the supernatants and cells were counted for 3 min using an automatic gamma counter (2480 Wizard$^2$ 3", Perkin Elmer, Waltham, Mass.). The activity data was automatically background-corrected by the instrument, and the amount of activity (antibody) bound to the cells was compared to activity of five 20 µL aliquots of the $^{177}$Lu-HOPO-trastuzumab solution to obtain the percent activity bound to the cells.

PET Imaging

Imaging can be performed in a temperature-controlled imaging suite with close monitoring of the physiological status of the mice. Small animal PET imaging can be performed on an Inveon PET/CT system. Following intravenous (i.v.) tail vein injection of 200-300 µCi of the $^{89}$Zr-radiolabeled compounds in the desired formulations, mice can be anesthetized with 1-2% isoflurane, placed in a supine position, and immobilized in a custom prepared cradle. Groups of 5 mice r a single injection of the $^{89}$Zr-radiolabeled agent. Animals can be imaged with data collection at selected time points. Standard uptake values (SUVs) can be generated from regions of interest (ROIs) drawn over the organs of interest.

PET imaging experiments were conducted on a microPET Focus 120. Female, athymic nude mice with BT474 xenografts on their right shoulders were administered $^{89}$Zr-HOPO-trastuzumab (9.25-9.99 MBq [250-270 µCi] in 200 µL 0.9% sterile saline) or $^{89}$Zr-DFO-trastuzumab (9.25-9.99 MBq [250-270 µCi] in 200 µL 0.9% sterile saline) via intravenous tail vein injection (t=0). Approximately 5 min prior to the acquisition of PET images, mice were anesthetized by inhalation of 2% isoflurane (Baxter Healthcare, Deerfield, Ill.)/oxygen gas mixture and placed on the scanner bed; anesthesia was maintained using 1% isoflurane/gas mixture. PET data for each mouse were recorded via static scans at various time points (n=4) between 6 h and 9 d. An energy window of 350-700 keV and a coincidence timing window of 6 ns were used. Data were sorted into 2D histograms by Fourier rebinning, and transverse images were reconstructed by filtered back-projection (FBP) into a 128×128×63 (0.72×0.72×1.3 mm3) matrix. The image data were normalized to correct for non-uniformity of response of the PET, dead-time count losses, positron branching ratio, and physical decay to the time of injection, but no attenuation, scatter, or partial-volume averaging correction was applied. The counting rates in the reconstructed images were converted to activity concentrations (percentage injected dose per gram of tissue, % ID/g) by use of a system calibration factor derived from the imaging of a mouse-sized water-equivalent phantom containing 89Zr. Images were analyzed using ASIPro VM software (Concorde Microsystems).

Biodistribution

Acute in vivo biodistribution studies were performed in order to compare the uptake of $^{89}$Zr-HOPO-trastuzumab and $^{89}$Zr-DFO-trastuzumab in BT474 tumor-bearing female, athymic nude mice. Mice were warmed gently with a heat lamp for 5 min before administration of $^{89}$Zr-HOPO-trastuzumab (0.59-0.67 MBq [16-18 µCi] in 200 µL 0.9% sterile saline) or $^{89}$Zr-DFO-trastuzumab (0.67-0.74 MBq [18-20 µCi] in 200 µL 0.9% sterile saline) via intravenous tail vein injection (t=0). Animals (n=4 per group) were euthanized by $CO_2$(g) asphyxiation at 1, 3, 5, 7, 9, and 14 d. After asphyxiation, 14 organs were removed, rinsed in water, dried in air for 5 min, weighed, and assayed for radioactivity on a gamma counter calibrated for $^{89}$Zr. Counts were converted into activity using a calibration curve generated from known standards. Count data were background- and decay-corrected to the time of injection, and the percent injected dose per gram (% ID/g) for each tissue sample was calculated by normalization to the total activity injected.

Hydroxyapatite Stability of $^{177}$Lu-HOPO and $^{177}$Lu-DOTA

Hydroxyapatite gel (1-5 mg, BIO-RAD, Hercules, Calif.) was incubated with 500 µL of 0.05 M tris buffer (pH 7.6) and 1 µL of $^{177}$Lu, $^{177}$Lu-HOPO, or $^{177}$Lu-DOTA solution (approximately 1 µCi each) in quadruplicate for each time point (1, 3, and 6 d) at 37° C. in a thermomixer. Additionally, each day the mixtures were vortexed to ensure proper mixing. At the respective time point, the aliquot was vortexed, centrifuged, vortexed, filtered (0.45 μm, 13 mm, nylon syringe filter, Fisher Scientific, Waltham, Mass.), and the filter washed with 1 mL of 50:50 EtOH in water. The filter (bound to hydroxyapatite), reaction tube, and filtrate (bound to the chelator) were counted separately on a gamma counter to determine the amount of activity in each.

EDTA Challenge of $^{177}$Lu-HOPO and $^{177}$Lu-DOTA

50 μL of $^{177}$Lu-HOPO solution (0.94 μCi/μL; 0.0088 mM), 50 μL of EDTA solution (pH adjusted to 8, 7, 6, or 5 and 0.9 mM), and 50 μL of NH$_4$OAc (pH adjusted to 8, 7, 6, or 5 and 0.5 mM) were added together. The solutions (triplicates of each pH) were incubated at 37° C. over 6 d in a thermomixer and radioTLC analyzed using C-18 TLC plates (Millipore, Billerica, Mass.) developed with 50 mM DTPA at 1 h, 1 d, 3 d, and 6 d.

Metal Ion Challenge of $^{177}$Lu-HOPO and $^{177}$Lu-DOTA $^{177}$Lu-HOPO or $^{177}$Lu-DOTA solution, PBS and a metal cation solution ($Cu^{2+}$, $Fe^{3+}$, $Ga^{3+}$, or $Gd^{3+}$ at 10 times the metal:ligand ratio) in equal volumes were incubated. Additionally, $^{177}$Lu-HOPO or $^{177}$Lu-DOTA solution at twice as much DME HG media without fetal calf serum and with penicillin and streptomycin were incubated (ratio of Metal:Ligand for $Ca^{2+}$, $Fe^{3+}$, $Mg^{2+}$, $K^+$, and $Na^+$ were 115.6, 0.015, 52.0, 340, and 9980, respectively). The incubations were performed at 37° C. in a thermomixer over the course of 6 d and analyzed by radioTLC using C-18 TLC plates developed with 50 mM DTPA at 1, 3, and 6 d.

What is claimed is:

1. A composition comprising:
an oxygen-bearing ligand comprising at least 8 coordination oxygens;
a radiolabel associated with the oxygen-bearing ligand; and
a spacer between the oxygen-bearing ligand and a conjugation functionality;
wherein the conjugation functionality comprises a moiety for association of the oxygen-bearing ligand with a targeting agent; and
wherein the oxygen-bearing ligand, the spacer, and the conjugation functionality together comprise

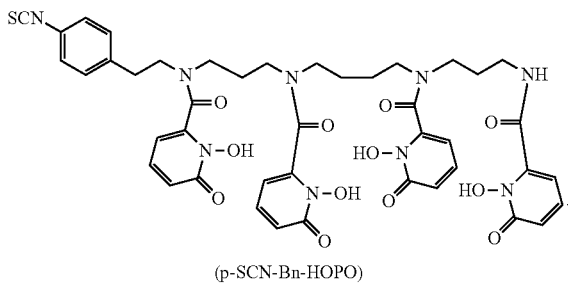

(p-SCN-Bn-HOPO)

2. The composition of claim 1, wherein the composition comprises the targeting agent and wherein the targeting agent is an antibody.

3. The composition of claim 2, wherein the antibody is a member selected from the group consisting of trastuzumab, rituximab, gemtuzumab ozogamicin, alemtuzumab, ibritumomab tiuxetan, tositumomab, cetuximab, bevacizumab, panitumomab, J591, B43.13, AR9.6, 3F8, 8H9, huA33, and 5B1.

4. The composition of claim 2, wherein the composition comprises $^{177}$Lu and/or $^{89}$Zr.

5. A method for detecting and/or analyzing tumor cells, the method comprising:
administering a quantity of the composition of claim 1 to a subject, wherein a portion of the quantity localizes at the tumor cells; and
imaging the composition accumulated in a region of the subject within a time period no longer than 336 hours from the administering of the quantity of the composition.

6. The method of claim 5, wherein the tumor cells are cells that express at least one marker of at least one of prostate cancer, lung cancer, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, Wilm's tumor, or combinations thereof.

7. The method of claim 5, wherein administering comprises injecting the quantity of the composition to the subject.

8. The method of claim 5, wherein the imaging is performed via positron emission tomography (PET) imaging.

9. The method of claim 5, wherein the composition comprises at least one europium(III) ion.

10. The method of claim 9, wherein imaging the composition comprises
directing light to excite at least one group in the oxygen-bearing ligand of the composition; and
detecting light emitted from the at least one europium(III) and/or other lanthanide ion.

11. The method of claim 10, wherein the directed light has a wavelength from 300 nm to 400 nm.

12. The method of claim 10, wherein the detected light comprises light in the visible and/or near infrared range.

13. The composition of claim 1, wherein the radiolabel is selected from the group consisting of $^{89}$Zr, $^{44}$Sc, $^{47}$Sc, $^{68}$Ga, $^{177}$Lu, $^{227}$Th, $^{166}$Ho, $^{90}$Y, $^{153}$Sm, $^{149}$Pm, $^{161}$Tb, $^{169}$Er, $^{175}$Yb, $^{161}$Ho, $^{167}$Tm, $^{142}$Pr, $^{143}$Pr, $^{145}$Pr $^{149}$Pr, $^{150}$Eu, $^{159}$Gd, $^{165}$Dy, $^{176m}$Lu, $^{179}$Lu, $^{142}$La, $^{150}$Pm, $^{156}$Eu, $^{157}$Eu, and $^{225}$Ac.

14. The composition of claim 1, wherein the composition comprises a plurality of radiolabels.

15. A method for detecting tumor cells, analyzing tumor cells, or both detecting and analyzing tumor cells, the method comprising:
injecting a quantity of the composition of claim 2 to a subject, wherein a portion of the quantity localizes at the tumor cells; and
imaging the composition accumulated in a region of the subject within a time period no longer than 336 hours from the administering of the quantity of the composition.

16. The method of claim 15, wherein the antibody is a member selected from the group consisting of trastuzumab, rituximab, gemtuzumab ozogamicin, alemtuzumab, ibritumomab tiuxetan, tositumomab, cetuximab, bevacizumab, panitumomab, J591, B43.13, AR9.6, 3F8, 8H9, huA33, and 5B1.

17. The method of claim 15, wherein the radiolabel is selected from the group consisting of $^{89}$Zr, $^{44}$Sc, $^{47}$Sc, $^{68}$Ga, $^{177}$Lu, $^{227}$Th, $^{166}$Ho, $^{90}$Y, $^{153}$Sm, $^{149}$Pm, $^{161}$Tb, $^{169}$Er, $^{175}$Yb, $^{161}$Ho, $^{167}$Tm, $^{142}$Pr, $^{143}$Pr, $^{145}$Pr, $^{149}$Pr, $^{150}$Eu, $^{159}$Gd, $^{165}$Dy, $^{176m}$Lu, $^{179}$Lu, $^{142}$La, $^{150}$Pm, $^{156}$Eu, $^{157}$Eu, and $^{225}$Ac.

18. The method of claim 15, wherein the tumor cells are cells that express at least one marker of at least one of prostate cancer, lung cancer, adenocarcinoma, adenoma, adrenal cancer, basal cell carcinoma, bone cancer, brain cancer, breast cancer, bronchi cancer, cervical dysplasia, colon cancer, epidermoid carcinoma, Ewing's sarcoma, gallbladder cancer, gallstone tumor, giant cell tumor, glioblastoma multiforma, head cancer, hyperplasia, hyperplastic corneal nerve tumor, in situ carcinoma, intestinal ganglioneuroma, islet cell tumor, Kaposi's sarcoma, kidney cancer, larynx cancer, leiomyoma tumor, liver cancer, malignant carcinoid, malignant hypercalcemia, malignant melanomas, marfanoid habitus tumor, medullary carcinoma, metastatic skin carcinoma, mucosal neuromas, mycosis fungoide, neck cancer, neural tissue cancer, neuroblastoma, osteogenic sarcoma, osteosarcoma, ovarian tumor, pancreas cancer, parathyroid cancer, pheochromocytoma, primary brain tumor, rectum cancer, renal cell tumor, retinoblastoma, rhabdomyosarcoma, seminoma, skin cancer, small-cell lung tumor, soft tissue sarcoma, squamous cell carcinoma, stomach cancer, thyroid cancer, topical skin lesion, veticulum cell sarcoma, Wilm's tumor, or combinations thereof.

19. The method of claim 18, wherein the antibody is a member selected from the group consisting of trastuzumab, rituximab, gemtuzumab ozogamicin, alemtuzumab, ibritumomab tiuxetan, tositumomab, cetuximab, bevacizumab, panitumomab, J591, B43.13, AR9.6, 3F8, 8H9, huA33, and 5B1.

20. The method of claim 19, wherein the radiolabel is selected from the group consisting of $^{89}$Zr, $^{44}$Sc, $^{47}$Sc, $^{68}$Ga, $^{177}$Lu, $^{227}$Th, $^{166}$Ho, $^{90}$Y, $^{153}$Sm, $^{149}$Pm, $^{161}$Tb, $^{169}$Er, $^{175}$Yb, $^{161}$Ho, $^{167}$Tm, $^{142}$Pr, $^{143}$Pr, $^{145}$Pr, $^{149}$Pr, $^{150}$Eu $^{159}$Gd, $^{165}$Dy, $^{176m}$Lu, $^{179}$Lu, $^{142}$La, $^{150}$Pm, $^{156}$Eu, $^{157}$Eu, and $^{225}$Ac.

21. The method of claim 15, wherein the imaging is performed via positron emission tomography (PET) imaging.

22. The method of claim 15, wherein
the composition comprises at least one europium(III) ion; and
wherein imaging the composition comprises
directing light has a wavelength from 300 nm to 400 nm to excite at least one group in the oxygen-bearing ligand of the composition; and
detecting visible light, near infrared light, or both, emitted from the at least one europium(III) ion.

* * * * *